United States Patent
Khanna et al.

(10) Patent No.: US 8,623,897 B2
(45) Date of Patent: Jan. 7, 2014

(54) METHODS AND COMPOSITIONS FOR TREATMENT OF DIABETES AND DYSLIPIDEMIA

(75) Inventors: Ish Khanna, Alpharetta, GA (US); Sivaram Pillarisetti, Norcross, GA (US)

(73) Assignee: Kareus Therapeutics, SA (CH)

( * ) Notice: Subject to any disclaimer, the term of this patent is extended or adjusted under 35 U.S.C. 154(b) by 15 days.

(21) Appl. No.: 13/236,807

(22) Filed: Sep. 20, 2011

(65) Prior Publication Data

US 2012/0071528 A1 Mar. 22, 2012

Related U.S. Application Data

(60) Provisional application No. 61/384,446, filed on Sep. 20, 2010.

(51) Int. Cl.
*A61K 31/41* (2006.01)
*C07C 61/12* (2006.01)

(52) U.S. Cl.
USPC ............ 514/381; 514/572; 562/500; 560/118

(58) Field of Classification Search
USPC ................... 514/381, 572; 562/500; 560/118
See application file for complete search history.

(56) References Cited

U.S. PATENT DOCUMENTS

| | | | |
|---|---|---|---|
| 3,773,946 A | 11/1973 | Creger | |
| 4,634,795 A | 1/1987 | Bar-Tana | |
| 4,689,344 A | 8/1987 | Bar-Tana | |
| 4,711,896 A | 12/1987 | Bar-Tana et al. | |
| 5,648,387 A | 7/1997 | Bisgaier et al. | |
| 5,750,569 A | 5/1998 | Bisgaier et al. | |
| 5,756,544 A | 5/1998 | Bisgaier et al. | |
| 5,783,600 A | 7/1998 | Bisgaier et al. | |
| 5,942,622 A | 8/1999 | Didierlaurent et al. | |
| 6,197,779 B1 | 3/2001 | Andries et al. | |
| 6,284,903 B1 | 9/2001 | Bar-Tana | |
| 6,387,897 B1 | 5/2002 | Snutch | |
| 6,440,986 B2 | 8/2002 | Andries et al. | |
| 6,440,996 B1 | 8/2002 | Kozikowski et al. | |
| 6,540,795 B2 | 4/2003 | Wood et al. | |
| 6,544,304 B2 | 4/2003 | Wood et al. | |
| 6,544,305 B2 | 4/2003 | Wood et al. | |
| 6,547,840 B2 | 4/2003 | Wood et al. | |
| 6,562,084 B2 | 5/2003 | Wood et al. | |
| 6,605,621 B1 | 8/2003 | Kozikowski et al. | |
| 6,699,910 B2 | 3/2004 | Dasseux et al. | |
| 6,903,213 B2 | 6/2005 | Andries et al. | |
| 6,905,525 B2 | 6/2005 | Wood et al. | |
| 7,119,221 B2 | 10/2006 | Dasseux et al. | |
| 7,335,689 B2 | 2/2008 | Dasseux et al. | |
| 7,335,799 B2 | 2/2008 | Dasseux et al. | |
| 7,405,226 B2 | 7/2008 | Dasseux et al. | |
| 7,576,130 B2 | 8/2009 | Dasseux et al. | |
| 7,812,199 B2 | 10/2010 | Dasseux et al. | |
| 7,838,554 B2 | 11/2010 | Dasseux et al. | |
| 8,026,248 B2 | 9/2011 | Andries et al. | |
| 2004/0082641 A1 | 4/2004 | Rytved et al. | |
| 2005/0192305 A1 | 9/2005 | Andries et al. | |
| 2008/0249166 A1 | 10/2008 | Dasseux et al. | |
| 2009/0253764 A1 | 10/2009 | Moinet et al. | |
| 2010/0032621 A1 | 2/2010 | Itano et al. | |
| 2010/0113599 A1 | 5/2010 | Bar-Tana | |
| 2010/0222534 A1 | 9/2010 | Adlem et al. | |

FOREIGN PATENT DOCUMENTS

| | | |
|---|---|---|
| DE | 198 37 620 A1 | 2/1999 |
| DE | 100 10 430 A1 | 9/2001 |
| EP | 1 130 469 A1 | 9/2001 |
| EP | 0 945 443 B1 | 2/2003 |
| WO | WO 96/30328 A1 | 10/1996 |
| WO | WO 00/20390 A1 | 4/2000 |
| WO | WO 02/079313 A1 | 10/2002 |
| WO | WO 2004/067489 A2 | 8/2004 |
| WO | WO 2005/068410 A1 | 7/2005 |
| WO | WO 2008/120424 A1 | 10/2008 |
| WO | WO 2009/039937 A1 | 4/2009 |

OTHER PUBLICATIONS

Petrov et al. CAS: 60: 72671, 1964.*
Ventura et al. CAS: 151:317448, 2008.*
Mail Stop PCT, Attn: ISA/US, Commissioner for Patents, PCT Notification of Transmittal of the International Search Report and the Written Opinion of the International Searching Authority, International Search Report, complete Jan. 17, 2012, mailed Feb. 2, 2012, and Written Opinion, mailed Feb. 2, 2012, PCT International Application No. PCT/US11/52318, Applicant—Kareus Therapeutics, SA.
Za'Tara et al. AMPK activation by long chain fatty acyl analogs, Biochemical pharmacology, 2008, vol. 76, pp. 1263-1275, p. 1266, col. 1, para 4 to col2, para 1, para 3; p. 1267, Fig 1.
PCT Internatonal Preliminary Report on Patentability in corresponding PCT Paten Application No. PCT/US2011/052318; 2011.
PCT Written Opinion of the International Searching Authority in corresponding PCT Paten Application No. PCT/US2011/052318; 2011.
PCT International Search Report in corresponding PCT Paten Application No. PCT/US2011/052318; 2001.

* cited by examiner

*Primary Examiner* — Rei-tsang Shiao
(74) *Attorney, Agent, or Firm* — Nelson Mullins Riley & Scarborough LLP

(57) ABSTRACT

The invention is directed to novel compounds of Formula I:

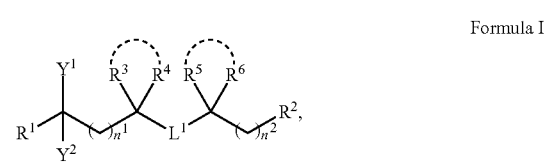

Formula I as well as its stereoisomers and/or pharmaceutically acceptable salts, for the treatment of diabetes and diabetes associated dyslipidemia.

12 Claims, No Drawings

METHODS AND COMPOSITIONS FOR TREATMENT OF DIABETES AND DYSLIPIDEMIA

This application is a non-provisional application and claims priority to U.S. Provisional Patent Application Ser. No. 61/384,446, filed Sep. 20, 2010, which is incorporated by reference herein in its entirety.

BACKGROUND OF THE INVENTION

The present invention relates to methods and compositions for the treatment of insulin resistance, diabetes and/or diabetes-associated dyslipidemia and cardiovascular disease. More specifically, the present invention relates to compositions of select cycloalkyl aliphatic carboxylic acids and derivatives for the treatment of insulin resistance, diabetes and diabetes-associated dyslipidemia.

SUMMARY OF THE INVENTION

In one aspect, the present invention is directed to novel compounds of Formula I:

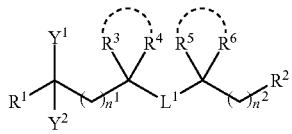

Formula I its stereoisomers and/or pharmaceutically acceptable salts for the treatment of diabetes and diabetes-associated dyslipidemia, wherein:
$R^1$ is selected from a group consisting of hydroxy, alkoxy, amine, alkyl, haloalkyl, $NHSO_2R$, or NHCOR wherein R is selected from alkyl or cycloalkyl, NHR' wherein R' is alkyl or cycloalkyl optionally substituted by hydroxy or alkoxy; and $n^1$ and $n^2$ are independently selected from 0, 1, and 2. At least one of $R^3$ and $R^4$ and/or $R^5$ and $R^6$ form a cyclic ring of 3-8 carbon atoms optionally containing alkyl groups, hetero atoms, or functional groups such as O, N, $SO_2$. Additionally, when $R^3$ and $R^4$ or $R^5$ and $R^6$ do not form a cyclic ring, then they may be independently selected from hydrogen, alkyl, branched alkyl, and cycloalkyl, $L_1$ is a linear aliphatic chain optionally containing from 4 to 16 carbon atoms. The chain may optionally be substituted one or more times by alkyl, branched alkyl, cycloalkyl, or aryl, $R^2$ is independently selected from hydrogen, alkoxy, hydroxy, alkyl, haloalkyl, cycloalkyl, heterocycloalkyl, heteroaryl, cyano, or $COR^7$, wherein $R^7$ is selected from hydroxy, alkyl, alkoxy, or amine, NHR'. $NHSO_2R$, or NHCOR. $Y^1$ is oxygen or hydrogen. $Y^2$ is optional, wherein when $Y^2$ is present, $Y^1$ and $Y^2$ are hydrogen. When $Y^2$ is not present, $Y^1$ is a carbonyl group.

In another aspect, the present invention is directed to a compound of Formula II

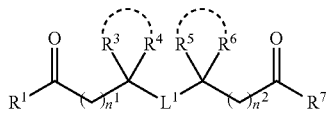

Formula II its stereoisomers and/or pharmaceutically acceptable salts for the treatment of diabetes and diabetes-associated dyslipidemia, wherein $R^1$ and $R^7$ are independently selected from a group consisting of hydroxy, alkoxy, alkyl, amine. NHR' wherein R' is alkyl or cycloalkyl optionally substituted by hydroxy or alkoxy. $NHSO_2R$ or NHCOR, wherein R is selected from alkyl or cycloalkyl and $n^1$ and $n^2$ are independently selected from 0, 1, and 2. At least one of $R^3$ and $R^4$ and/or $R^5$ and $R^6$ form a cyclic ring of 3-8 carbon atoms optionally containing alkyl groups, hetero atoms, or functional groups such as O, N, $SO_2$. Additionally, when $R^3$ and $R^4$ or $R^5$ and $R^6$ do not form a cyclic ring, then they may be independently selected from hydrogen, alkyl, branched alkyl, and cycloalkyl. $L^1$ is independently a linear aliphatic chain optionally containing from 6 to 16 carbon-atoms and $L^1$ may optionally be substituted one or more times by alkyl, branched alkyl, cycloalkyl, or aryl.

In yet another aspect, the invention is directed to novel compounds of Formula I, its stereoisomers, tautomers and/or its pharmaceutically acceptable salt thereof as AMPK activators.

In a different aspect, the invention is directed to novel compounds of Formula I, its stereoisomers, tautomers and/or its pharmaceutically acceptable salt thereof as inhibitors of lipid synthesis In another aspect, the invention is directed to a method for the treatment of diabetes, insulin resistance, dyslipidemia, obesity and cardiovascular disease in a subject, which comprises administering to the subject a therapeutically effective amount of a compound of formula (I), its stereoisomers and/or its pharmaceutically acceptable salt thereof.

DETAILED DESCRIPTION OF THE INVENTION

Reference will now be made in detail to the embodiments of the invention, one or more examples of which are set forth below. Each example is provided by way of explanation of the invention, not a limitation of the invention. In fact, it will be apparent to those skilled in the art that various modifications can be made in the present invention without departing from the scope or spirit of the invention. For instance, features illustrated or described as part of one embodiment can be used on another embodiment to yield a still further embodiment. Thus it is intended that the present invention cover such modifications and variations as come within the scope of the appended claims and their equivalents. Other objects, features, and aspects of the present invention are disclosed in, or are obvious from, the following detailed description.

In one aspect, the present invention is directed to novel compounds of Formula I:

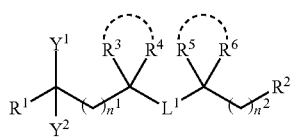

Formula I its stereoisomers and/or pharmaceutically acceptable salts for the treatment of diabetes and diabetes-associated dyslipidemia, wherein
$R^1$ is selected from a group consisting of hydroxy, alkoxy, amine, alkyl, haloalkyl. $NHSO_2R$, or NHCOR wherein R is selected from alkyl or cycloalkyl. NHR' wherein R' is alkyl or cycloalkyl optionally substituted by hydroxy or alkoxy; and $n^1$ and $n^2$ are independently selected from 0, 1, and 2. At least one of $R^3$ and $R^4$ and/or $R^5$ and $R^6$ form a cyclic ring of 3-8 carbon atoms optionally containing alkyl groups, hetero atoms, or functional groups such as O, N, $SO_2$. Additionally, if $R^3$ and $R^4$ or $R^5$ and $R^6$ do not form a cyclic ring, then they may be independently selected from hydrogen, alkyl, branched alkyl, and cycloalkyl. $L_1$ is a linear aliphatic chain optionally containing from 4 to 16 carbon atoms. The chain may optionally be substituted one or more times by alkyl, branched alkyl, cycloalkyl, or aryl. $R^2$ is independently selected from hydrogen, alkoxy, hydroxy, alkyl, haloalkyl, cycloalkyl, heterocycloalkyl, heteroaryl, cyano, or $COR^7$, wherein $R^7$ is selected from hydroxy, alkyl, alkoxy, or amine, NHR'. $NHSO_2R$, or NHCOR. $Y^1$ is oxygen or hydrogen. $Y^2$ is optional, wherein when $Y^2$ is present, $Y^1$ and $Y^2$ are hydrogen. When $Y^2$ is not present, $Y^1$ is a carbonyl group In another aspect, the present invention is directed to a compound of Formula II

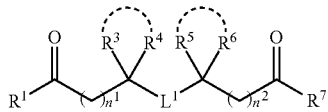

Formula II its stereoisomers and/or pharmaceutically acceptable salts for the treatment of diabetes and diabetes-associated dyslipidemia, wherein $R^1$ and $R^7$ are independently selected from a group consisting of hydroxy, alkoxy, alkyl, amine, NHR' wherein R' is alkyl or cycloalkyl optionally substituted by hydroxy or alkoxy, $NHSO_2R$ or NHCOR, wherein R is selected from alkyl or cycloalkyl and $n^1$ and $n^2$ are independently selected from 0, 1, and 2. At least one of $R^3$ and $R^4$ and/or $R^5$ and $R^6$ form a cyclic ring of 3-8 carbon atoms optionally containing alkyl groups, hetero atoms, or functional groups such as O, N, $SO_2$. Additionally, when $R^3$ and $R^4$ or $R^5$ and $R^6$ do not form a cyclic ring, then they may be independently selected from hydrogen, alkyl, branched alkyl, and cycloalkyl. $L^1$ is independently a linear aliphatic chain optionally containing from 6 to 16 carbon-atoms and $L^1$ may optionally be substituted one or more times by alkyl, branched alkyl, cycloalkyl, or aryl.

In another aspect, the present invention is directed to a compound of Formula III

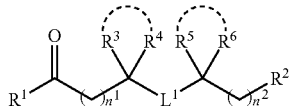

Formula III its stereoisomers and/or pharmaceutically acceptable salts for the treatment of diabetes and diabetes-associated dyslipidemia, wherein $R^1$ is selected from a group consisting of hydroxy, alkoxy, amine, alkyl, haloalkyl. NHR' wherein R' is alkyl or cycloalkyl optionally substituted by hydroxy or alkoxy, $NHSO_2R$ or NHCOR, wherein R is selected from alkyl or cycloalkyl; and $n^1$ and $n^2$ are independently selected from 0, 1, and 2. At least one of $R^3$ and $R^4$ and/or $R^5$ and $R^6$ form a cyclic ring of 3-8 carbon atoms optionally containing alkyl groups, hetero atoms, or functional groups such as O, N, $SO_2$. Additionally, when $R^3$ and $R^4$ or $R^5$ and $R^6$ do not form a cyclic ring, then they may be independently selected from hydrogen, alkyl, branched alkyl, and cycloalkyl. $L^1$ is a linear aliphatic chain optionally containing from 4 to 16 carbon-atoms and $L^1$ may optionally be substituted one or more times by alkyl, branched alkyl, cycloalkyl, or aryl. $R^2$ is independently selected from hydrogen, alkoxy, hydroxy, alkyl, haloalkyl, cycloalkyl, heterocycloalkyl, heteroaryl, cyano or $COR^7$; wherein $R^7$ is selected from a group consisting of hydroxy, alkyl, alkoxy, amine. NHR', or $NHSO_2R$.

In another embodiment of present invention, the compound of present invention is selected from one or more of:

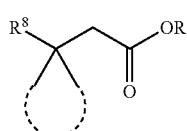

$R^8$ = alkyl, or Ph
R = H or alkyl

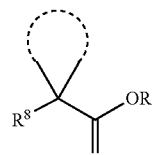

$R^8$ = alkyl, or Ph
R = H or alkyl

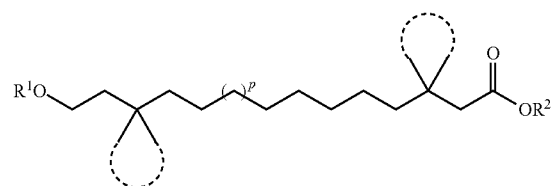

$R^1$, $R^2$ = H or alkyl
p = 0-4

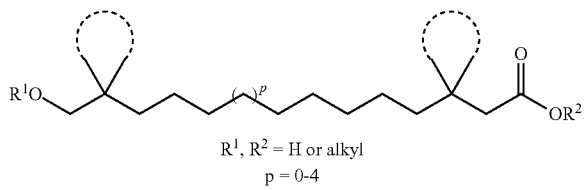

$R^1$, $R^2$ = H or alkyl
p = 0-4

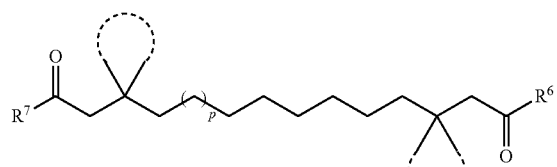

$R^6$, $R^7$ = OH, or alkoxy, amine, $NHSO_2R$, NHR'
p = 0-4

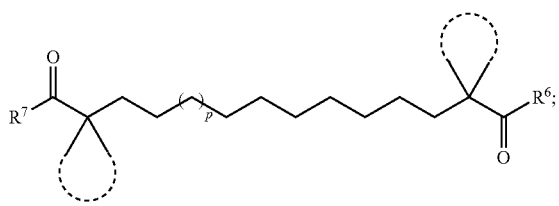

$R^6$, $R^7$ = OH, alkoxy, alkyl amine $NHSO_2R$, NHR'
p = 0-4

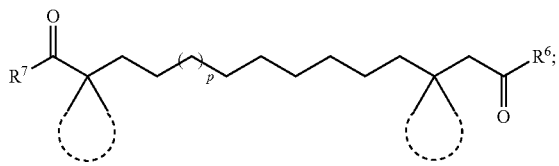

$R^6$, $R^7$ = OH, alkoxy, alkyl amine, $NHSO_2R$, NHR'
p = 0-4

-continued

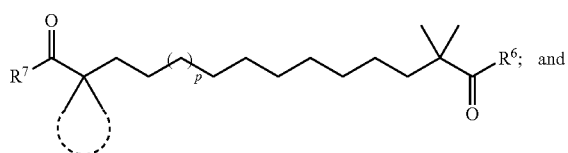

R$^6$, R$^7$ = OH, alkoxy, alkyl amine, NHSO$_2$R, NHR'
p = 0-4

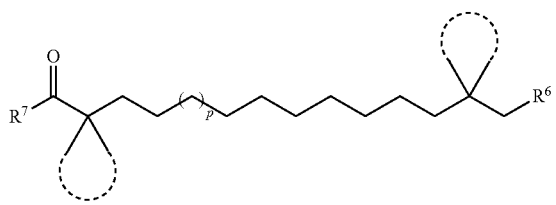

R$^6$, R$^7$ = OH, alkoxy, alkyl, haloalkyl amine, NHSO$_2$R, NHR', hetroaryl
p = 0-4 their stereoisomers, pharmaceutically acceptable salts, tautomers, and mixtures thereof.

In another embodiment of present invention, the compound of present invention is selected from one or more of:

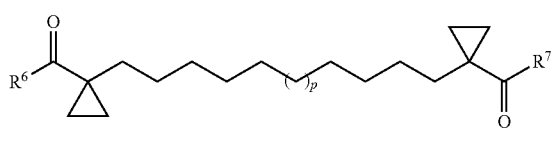

R$^6$, R$^7$ = OH, alkoxy, amine, NHSO$_2$R
p = 1-3

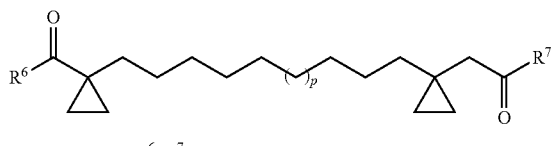

R$^6$, R$^7$ = OH, alkoxy, amine, NHSO$_2$R
p = 1-3

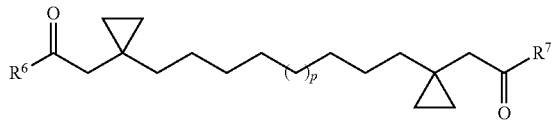

R$^6$, R$^7$ = OH, alkoxy, amine, NHSO$_2$R
p = 1-3

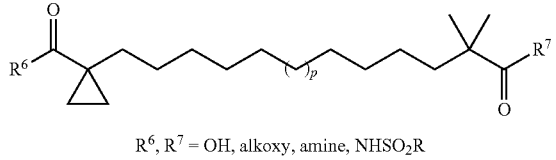

R$^6$, R$^7$ = OH, alkoxy, amine, NHSO$_2$R
p = 1-3

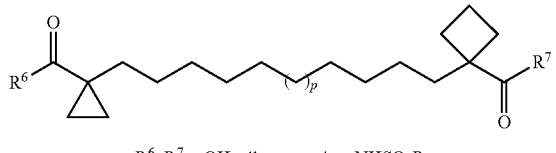

R$^6$, R$^7$ = OH, alkoxy, amine, NHSO$_2$R
p = 1-3

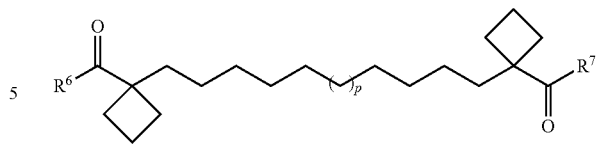

R$^6$, R$^7$ = OH, alkoxy, amine, NHSO$_2$R
p = 1-3

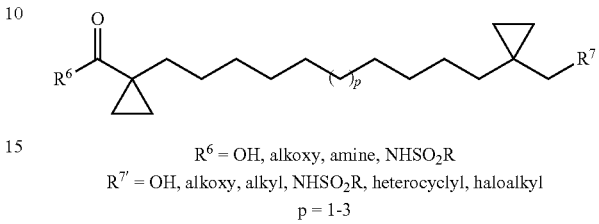

R$^6$ = OH, alkoxy, amine, NHSO$_2$R
R$^{7'}$ = OH, alkoxy, alkyl, NHSO$_2$R, heterocyclyl, haloalkyl
p = 1-3

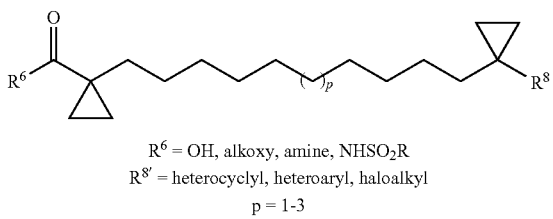

R$^6$ = OH, alkoxy, amine, NHSO$_2$R
R$^{8'}$ = heterocyclyl, heteroaryl, haloalkyl
p = 1-3

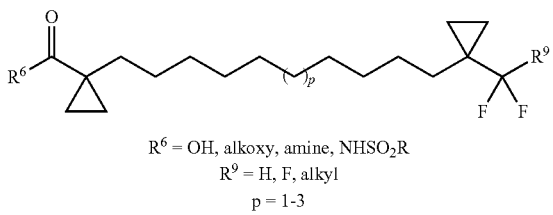

R$^6$ = OH, alkoxy, amine, NHSO$_2$R
R$^9$ = H, F, alkyl
p = 1-3

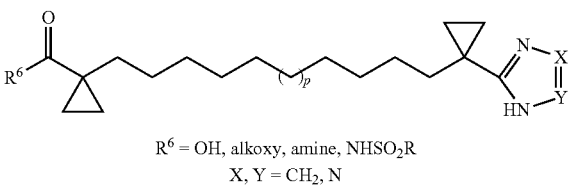

R$^6$ = OH, alkoxy, amine, NHSO$_2$R
X, Y = CH$_2$, N
p = 1-3

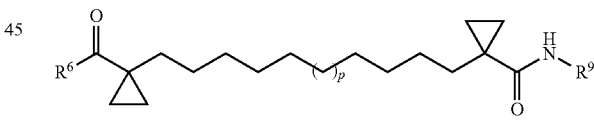

R$^6$ = OH, alkoxy, amine, NHSO$_2$R
R$^9$ = H, alkyl, cycloalkyl
p = 1-3

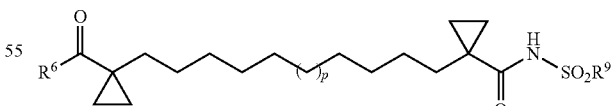

R$^6$ = OH, alkoxy, amine, NHSO$_2$R
R$^9$ = alkyl, cycloalkyl
p = 1-3 their stereoisomers, pharmaceutically acceptable salts, tautomers, and mixtures thereof.

In another embodiment of present invention, the compound of present invention is selected from one or more of:

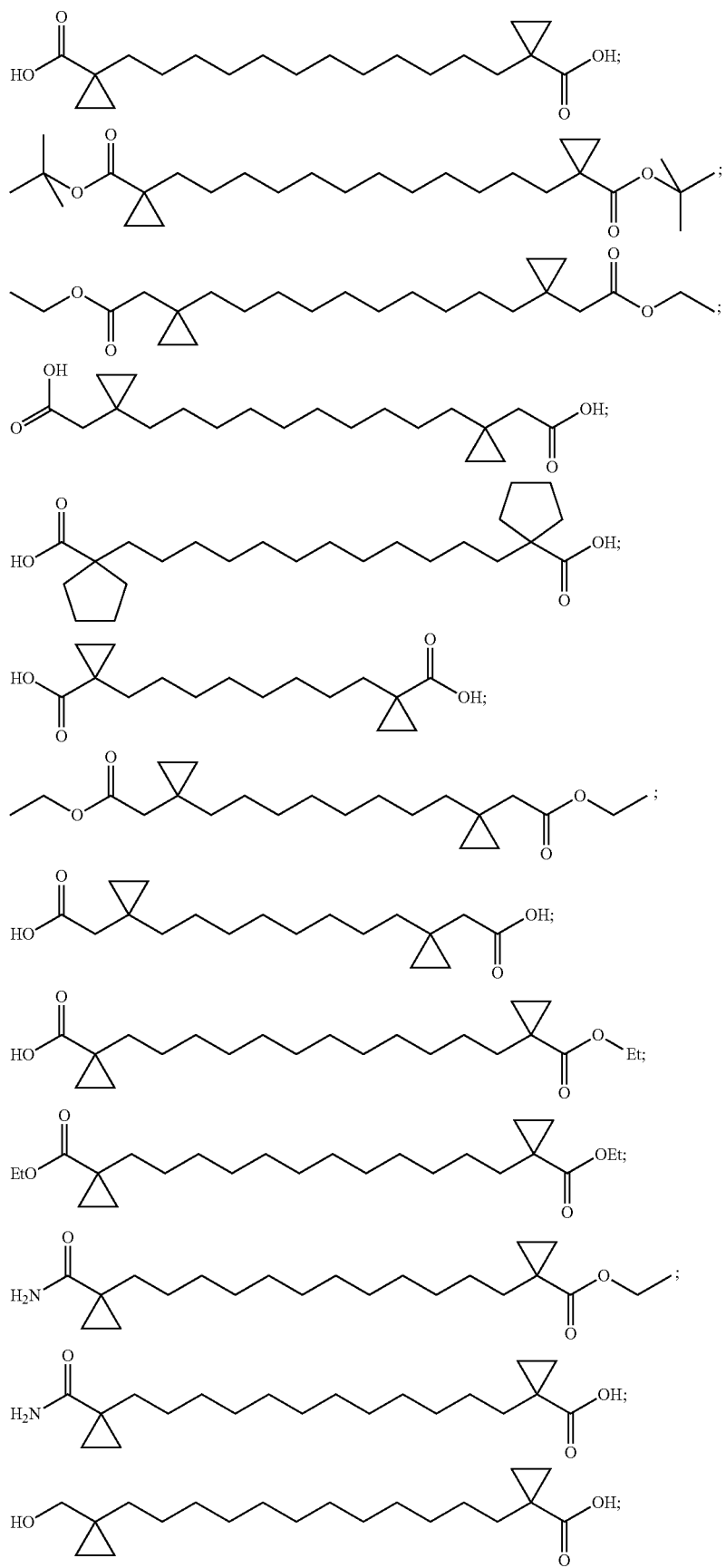

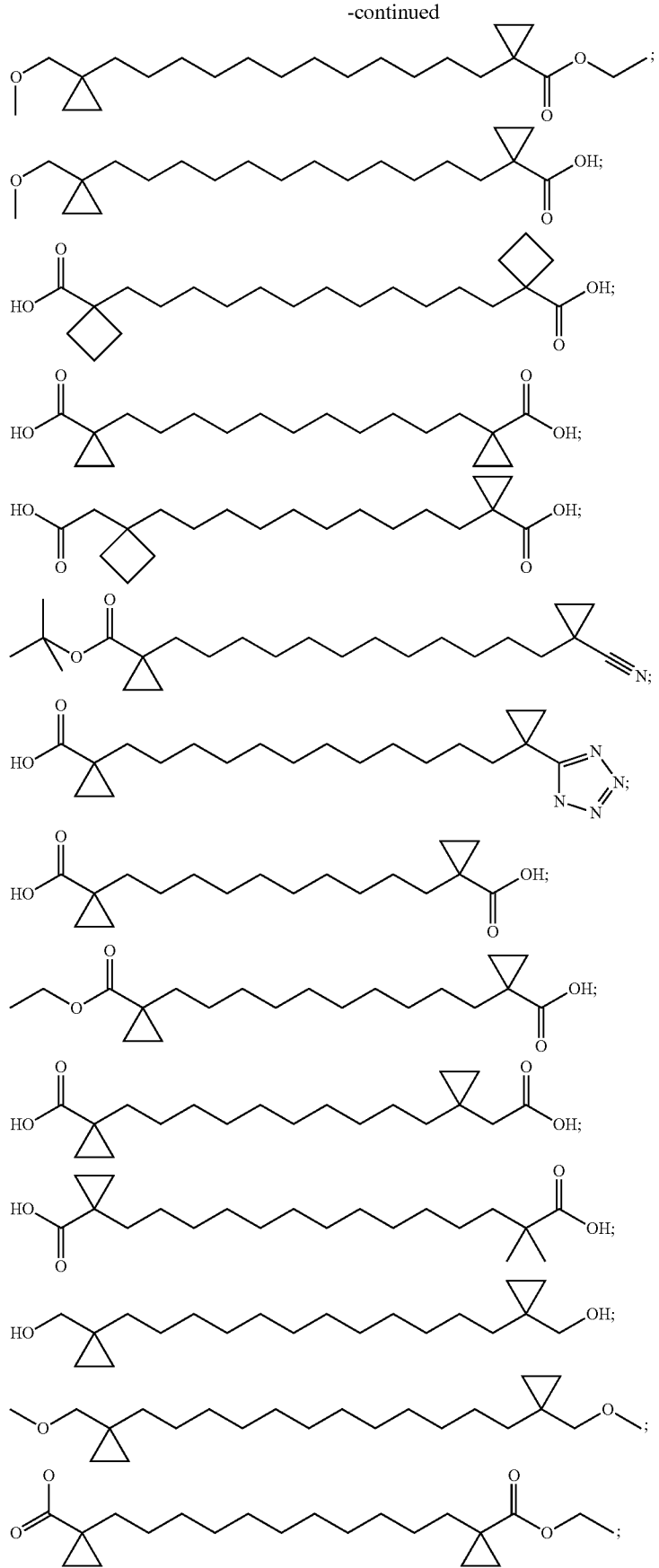

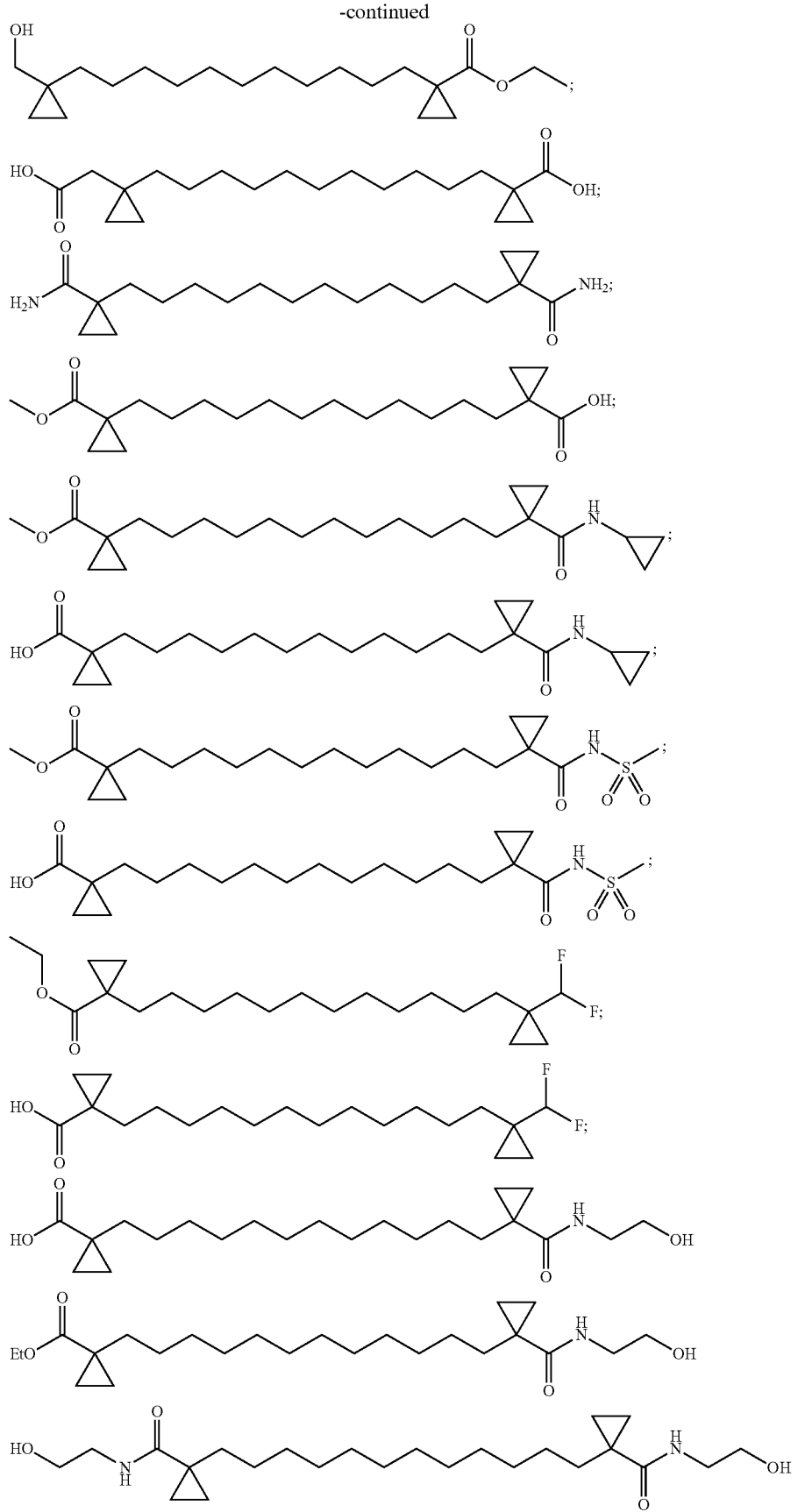

their stereoisomers, pharmaceutically acceptable salts, tautomers, and mixtures thereof.

In one embodiment, the invention is directed to novel compounds of Formula (I), their stereoisomers, tautomers and/or their pharmaceutically acceptable salts as AMPK activators In another embodiment, the invention is directed to novel compounds of Formula (I), their stereoisomers, tautomers and/or pharmaceutically acceptable salts as inhibitors of lipid synthesis.

In another embodiment, the invention is directed to a method for the treatment of diabetes, insulin resistance, dyslipidemia, obesity or cardiovascular disease in a subject, which comprises administering to the subject a therapeutically effective amount of a compound of formula (I), its stereoisomers and/or pharmaceutically acceptable salts thereof.

In another embodiment of present invention, the compounds of Formula I, II or III may optionally be combined with one or more anti-diabetic or dyslipidemia drugs such as metformin, DDP-IV inhibitor, sulfonylurea, SGLT-2 inhibitors statins, alpha glucosidase inhibitors, and insulin.

In an embodiment of present invention, metformin combines with mono- or dicarboxylic fatty acid of Formula I, II or III to form salts suitable for oral delivery—

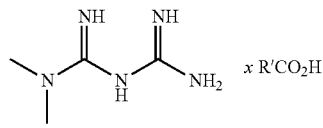

wherein R'CO$_2$H is a fatty acid of present invention of Formula I, II or III and x is the molar ratio of fatty acid in metformin combination and may range from about 0.5 to about 3.

In another embodiment, the present invention describes a pharmaceutical composition containing compounds of the present invention and one or more pharmaceutically acceptable excipients.

In yet another embodiment, the present invention describes a method of preventing or treating insulin resistance and diabetes in a subject. The method involves administering to a subject an effective amount of compound(s) of the present invention or a composition thereof.

In another embodiment, the effective amount of a compound of the present invention is delivered orally, sublingually or intravenously. Other administration means known in the art are also contemplated as useful in accordance with the present invention.

As used herein, the following terms are defined as:

'Halogen or Halo' means fluorine, chlorine, bromine or iodine.

'Alkyl' group means linear or branched alkyl groups. Exemplary alkyl groups include methyl, ethyl, n-propyl, iso-propyl, n-butyl, iso-butyl, t-butyl, n-pentyl, iso-pentyl, hexyl, heptyl, octyl and the like. Unless otherwise specified, an alkyl group typically has from about 1 to about 10 carbon atoms.

'Cycloalkyl' group means a cyclic alkyl group which may be mono or bicyclic. Exemplary cycloalkyl groups include cyclopropyl, cyclobutyl, cyclopentyl, cyclohexyl, cycloheptyl, cyclooctyl and the like. Unless otherwise specified, a cycloalkyl group typically has from about 3 to about 10 carbon atoms.

'Alkoxy' means an —O (alkyl) group, where alkyl is as defined above. Exemplary alkyl groups include methoxy, ethoxy, propoxy, butoxy, iso-propoxy, iso-butoxy, and the like. Unless otherwise specified, an alkoxy group typically has from 1 to about 10 carbon atoms.

'Amine' refers to a primary, secondary, or tertiary amino group. The secondary and tertiary amine may contain alkyl, cycloalkyl or aryl substitutions. Some examples of amines include NH$_2$, NHMe, NMe$_2$ NH(cyclopropyl). Unless otherwise specified, the alkyl or cycloalkyl group on an amine typically has from 1 to about 8 carbon atoms.

'Aryl' means an optionally substituted monocyclic or polycyclic aromatic ring system of about 6 to about 14 carbon atoms. Exemplary aryl groups include phenyl, naphthyl, and the like. Unless otherwise specified, an aryl group typically has from 6 to about 14 carbon atoms.

'Heteroaryl' means an aromatic monocyclic or polycyclic ring system of about 4 to about 10 carbon atoms, having at least one heteroatom or hetero group selected from —O—, —N—, —S—, —SO$_2$, or —CO. Exemplary heteroaryl groups include one or more of pyrazinyl, isothiazolyl, oxazolyl, pyrazolyl, pyrrolyl, tetrazolyl, imidazolyl, triazolyl, pyridazinyl, thienopyrimidyl, furanyl, indolyl, isoindolyl, benzo[1,3]dioxolyl, 1,3-benzoxathiole, pyrrolidine 2,4-dione, quinazolinyl, pyridyl, thiophenyl and the like. Unless otherwise specified, a heteroaryl group typically has from 4 to about 10 carbon atoms.

'5- to 6-member heteroaryl' is an aromatic monocyclic ring system of 5 or 6 ring atoms, having at least one heteroatom or hetero group selected from —O—, —N—, —S—, —SO$_2$, or —CO. Exemplary '5- to 6-member heteroaryl' groups include one or more of pyrazinyl, isothiazolyl, oxazolyl, pyrazolyl, pyrrolyl, pyridazinyl, pyridyl, thienopyrimidyl, tetrazolyl, imidazolyl, triazolyl, furanyl and the like.

'Heterocyclyl' means a non-aromatic saturated monocyclic or polycyclic ring system of 3 to about 10 members having at least one heteroatom or hetero group selected from —O—, —N—, —S—, —SO$_2$, or —CO. Exemplary heterocyclyl groups include one or more of pyrrolidinyl, piperidinyl, piperazinyl, morpholinyl, thiomorpholinyl, thiomorpholine 1,1-dioxide, oxetane, thiazolidinyl, 1,3-dioxolanyl, 1,4-dioxanyl and the like. Unless otherwise specified, a heterocyclyl group typically has from 3 to about 10 carbon atoms.

'Optionally substituted' means that substitution is optional and, therefore, it is possible for the designated atom or molecule to be unsubstituted. In the event a substitution is desired, then such substitution means that any number of hydrogens on the designated atom is replaced with a selection from the indicated group, provided that the normal valence of the designated atom is not exceeded, and that the substitution results in a stable compound. For example in Formula I when a substituent is keto (i.e., =O), then 2 hydrogens on the atom are replaced.

'Salts' refers to any acid or base salt, pharmaceutically acceptable solvates, or any complex of the compound that, when administered to a recipient, is capable of providing (directly or indirectly) a compound as described herein. It should be appreciated, however, that salts that are not pharmaceutically acceptable also lie within the scope of the invention. The preparation of salts can be carried out using known methods.

For example, pharmaceutically acceptable salts of compounds contemplated herein as being useful may be synthesized by conventional chemical methods using a parent compound containing a base or an acid functionality. Generally, such salts may be prepared, for example, by making free acid or base forms of the compounds and reacting with a stoichiometric quantity of the appropriate base or acid in water or in an organic solvent, or in a mixture of the two. Generally, non-aqueous media such as one or more of solvents such as ether, ethyl acetate, ethanol, isopropanol or acetonitrile may be utilized. Examples of acid addition salts include one or more of mineral acid addition salts such as hydrochloride, hydrobromide, hydroiodide, sulphate, phosphate, and organic acid addition salts such as one or more of acetate, maleate, fumarate, citrate, oxalate, succinate, tartrate, malate, mandelate, methanesulphonate and p-toluenesulphonate. Examples of base addition salts include one or more of inorganic salts such as sodium, potassium, calcium, ammonium, magnesium, and lithium salts, and organic base salts such as one or more of ethylenediamine, ethanolamine, N,N-dialkylethanolamine, triethanolamine, and basic amino acid salts.

Contemplated derivatives are those that may improve dissolution or increase the bioavailability of the compounds of this invention when such compounds are administered to a subject (e.g., by making an orally administered compound more easily absorbed. Compounds of formula I may be amorphous, semi-crystalline, or crystalline and may either be given as parent compounds, its salts, and/or in solvated form. The solvate may be part of crystalline lattice or superficially associated. It is intended that all of these forms should be within the scope of the present invention. Methods of solvation are generally known within the art. Suitable solvates are pharmaceutically acceptable solvates. In one embodiment, the solvate is a hydrate.

For ease of reference, the present invention will be described in terms of administration to human subjects. It will be understood, however, that such descriptions are not limited to administration to humans, but will also include administration to other animals unless explicitly stated otherwise.

In one embodiment compounds of Formula I are useful for the treatment of diabetes, insulin resistance, hyperlipidemia, coronary heart disease, atherosclerosis, diabetes, and obesity. The compounds of Formula I may influence one or more lipid parameters such as increasing the HDL levels, lowering plasma levels of LDL, lowering plasma glucose, or lowering triglycerides.

Compounds of formula I, their pharmaceutically acceptable salts, and/or solvates thereof can, therefore, be used in the prevention and/or treatment of a disease or condition discussed above. Pharmaceutical compositions containing a therapeutically effective quantity of a compound of formula I, its pharmaceutically acceptable salts, and/or solvates thereof, together with pharmaceutically acceptable excipients, are an additional aspect of the present invention.

The therapeutically effective quantity of compounds of formula I, their pharmaceutically acceptable salts and/or solvates that must be administered, and the dosage for treating a pathological state with said compounds will depend on numerous factors, including age, the state of the patient, the severity of the disease, the route and frequency of administration, the modulator compound to be used, etc.

As used herein, "therapeutically effective amount" means the dose or amount of a compound of the present invention administered to a subject and the frequency of administration to give some therapeutic response. The dose or effective amount to be administered to a subject and the frequency of administration to the subject can be readily determined by one of ordinary skill in the art by the use of known techniques and by observing results obtained under analogous circumstances. In determining the effective amount or dose, a number of factors are considered by the attending diagnostician, including but not limited to, the potency and duration of action of the compounds used; the nature and severity of the illness to be treated as well as on the sex, age, weight, general health and individual responsiveness of the subject to be treated, and other relevant circumstances.

The phrase "therapeutically-effective" indicates the capability of an agent or combination to prevent, or improve on the severity of, the disorder, while avoiding adverse side effects. The therapeutically effective compositions of the present invention may include compounds of present invention at doses of from about 50 to about 3000 mg.

The compounds described herein are typically administered in admixture with one or more pharmaceutically acceptable excipients or carriers in the form of a pharmaceutical composition. A "composition" may contain one compound or a mixture of compounds. A "pharmaceutical composition" is any composition useful or potentially useful in producing physiological response in a subject to which such pharmaceutical composition is administered.

The term "pharmaceutically acceptable," with respect to an excipient, is used to define non-toxic substances generally suitable for use in human or animal pharmaceutical products. The pharmaceutical composition may be in the forms normally employed, such as tablets, capsules, powders, syrups, solutions, suspensions, and the like. The pharmaceutical composition may contain flavorants, sweeteners, etc., in suitable solid or liquid carriers or diluents, or in suitable sterile media to form injectable solutions or suspensions. Such compositions typically contain from about 0.1 to about 50%, in some embodiments from about 1 to about 20%, by weight of active compound, the remainder of the composition being pharmaceutically acceptable carriers, diluents or solvents.

Suitable pharmaceutically acceptable carriers include solid fillers or diluents and sterile aqueous or organic solutions. The active ingredient may be present in such pharmaceutical compositions in the amounts sufficient to provide the desired dosage in the range as described above. Thus, for oral administration, the active ingredient may be combined with a suitable solid or liquid carrier or diluent to form capsules, tablets, powders, syrups, solutions, suspensions and the like. For parenteral administration, the active ingredient can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. Aqueous solutions with the active ingredient dissolved in polyhydroxylated castor oil may also be used for injectable solutions. The injectable solutions prepared in this manner can then be administered intravenously, intraperitoneally, subcutaneously, or intramuscularly, with intramuscular administration being preferred in humans.

The following examples describe exemplary embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples.

The following outlines general synthesis of compounds of the invention. The suggested methodologies are not intended to be limiting. The variations of these synthetic methodologies or methodologies reported in literature can be adopted to synthesize molecules within the scope of invention.

Scheme A—General Synthesis of Compounds of Formula I

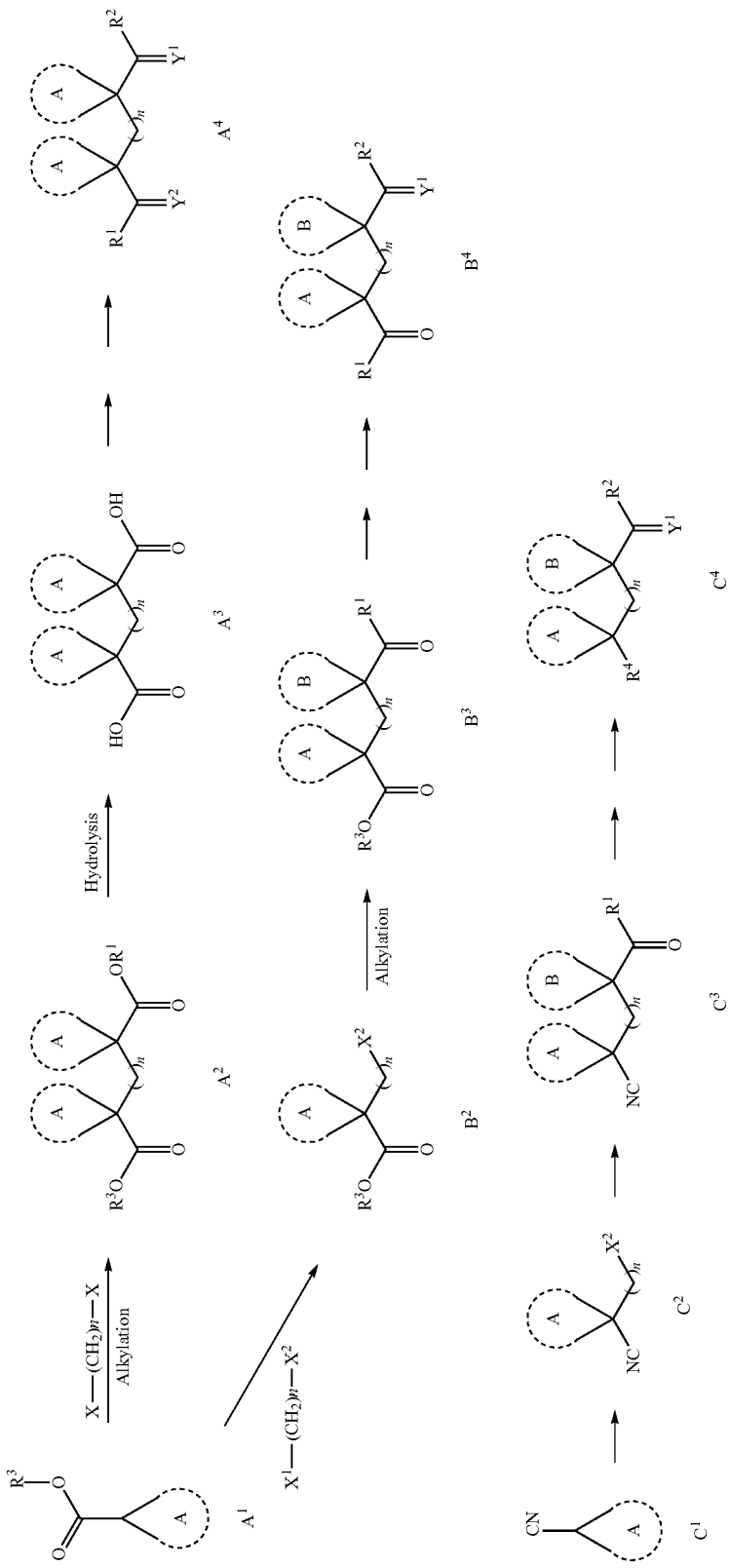

Scheme A outlines a generic synthesis of compounds of Formula I. The symmetrical compounds such as formula A2 and A3 are synthesized by quenching the carbanion generated from cycloalkyl carboxylic acid or its ester with alkyl dihalide. Using conditions known in literature, selective functional group transformations of carboxyl acid, ester gives alcohol, amides, or esters that may be further manipulated to give ether, haloalkyl, amines, ketones, etc (A4).

The unsymmetrical compounds ($B^3$, $B^4$) are synthesized using sequential anion generation followed by alkylation steps to give $B^2$ and $B^3$. Functional group manipulations of carboxyl acid, ester as discussed above gives alcohol, amides, esters that may be further manipulated selectively to give ether, haloalkyl, amines, ketones etc. ($B^4$).

Similarly, the cycloalkyl (or branched alkyl) nitrile can be used as starting points to synthesize $C^2$ and $C^3$. The selective manipulation of cyano group can give easy access to heteroaryl systems or be hydrolyzed to acids or amides and further elaborated per need to give $C^4$.

The functional carboxylic acid group(s) in $A^3/A^4/B^3/B^4/C^3/C^4$ may be homologated using Arndt-Eistert synthesis or other methodologies known in literature. The selective functional groups transformations are used further to give target compounds of Formula I.

EXAMPLES

An embodiment of the present invention provides preparation of the novel compounds of formula (I) using the procedures given in the following examples. Those skilled in the art will understand that known variations of the conditions and processes of the following preparative procedures can be used to prepare these compounds. Moreover, by utilizing the procedures described in detail, one of ordinary skill in the art can prepare additional compounds of the present invention claimed herein.

The following acronyms, abbreviations, terms and definitions are used throughout the reaction scheme and experimental section:

THF (tetrahydrofuran)
TBME (tert-butyl methyl ether)
MeOH (methanol)
Ether (diethyl ether)
EtOAc (ethyl acetate)
CDI (Carbonyldiimidazole)
DCM (Dichloromethane)
DMF (N,N-dimethylformamide),
DMSO (dimethyl sulfoxide)
DIEA [(N,N-diisopropylethylamine) (Hünig's base)]
DMAP (4-Dimethylaminopyridine)
DBU (1,8-Diazabicyclo[5.4.0]undec-7-ene)
DMPU [1,3-Dimethyl-3,4,5,6-tetrahydro-2(1H)-pyrimidinone]
LiHMDS (lithium hexamethyldisilazine)
TMS (tetramethylsilane)
TFA (trifluoracetic acid)
TLC (thin layer chromatography)
LCMS (liquid chromatographic mass spectroscopy)
MS (mass spectroscopy) giving molecular ion
NMR (nuclear magnetic resonance)
The chemical shifts values are expressed in ppm related to tetramethylsilane as internal standard.
br (broad),
apt (apparent),
s (singlet),
d (doublet),
t (triplet),
q (quartet),
dd (doublet of doublets),
m (multiplet).
HPLC (high performance liquid chromatography)
Mp/mp (melting point)
aq (aqueous)
All temperatures are in degrees Celsius (° C.) unless otherwise noted.
Abbreviations and acronyms used in biological screens include:
DMEM (Dulbecco's Modified Eagle's Medium)
FCS (fetal calf serum)
PBS (phosphate buffered saline)
BCA—bicinchoninic acid Example 1

Synthesis of 2,15-Dicycloproryl-hexadecanedioic acid

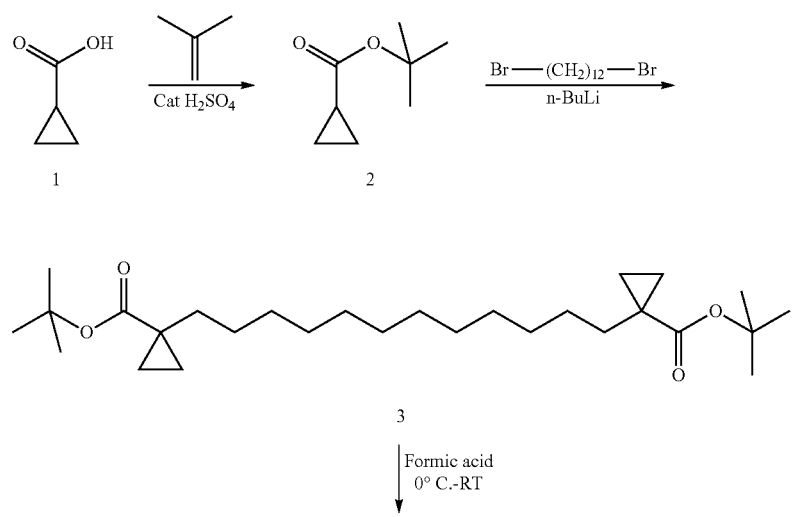

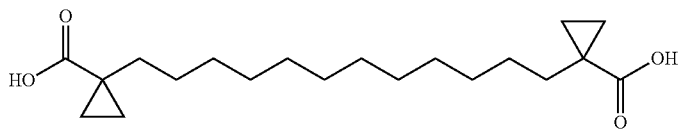

Step 1—To a cooled (−78° C.) sealed tube was added isobutylene (800 mL), cyclopropane carboxylic acid (18.4 mL, 0.23 mol), t-butanol (2.0 mL) and catalytic amount of sulphuric acid (1.0 mL). The cooled bath was removed and the reaction mixture stirred at room temperature over a period of 72 hours. The sealed tube was re-cooled (−78° C.), opened to atmosphere and excess isobutylene evaporated under a stream of nitrogen while allowing the reaction mixture to attain room temperature. The resulting mixture was diluted with ether (500 mL), washed with saturated NaHCO$_3$ solution (300 mL×3), water (300 mL), brine (300 mL), dried over anhydrous sodium sulphate, and evaporated under reduced pressure to give a pale, yellow liquid which was purified by fractional distillation under reduced pressure (120° C., 30 mm Hg) to give product as a colorless liquid 20.0 g (60%).

$^1$H NMR (CDCl$_3$, δ (ppm): 0.78-0.81 (m, 2H), 0.89-0.94 (m, 2H), 1.42 (s, 9H), 1.45-1.54 (m, 1H).

Step 2—A solution of n-butyl lithium in hexane (1.4M, 107 mL, 0.15 mol) was added dropwise to a solution of freshly distilled diisopropylamine (19.6 mL, 0.14 mol) in dry THF (160 mL) at −60° C. under a nitrogen atmosphere. The reaction mixture was slowly warmed to −20° C. and stirred for 30 min. The reaction mixture was re-cooled to −60° C. and cyclopropanecarboxylic acid tert-butyl ester (20 g, 0.14 mol) was added dropwise over a period of 15 min. The reaction mixture was slowly warmed to −20° C. and stirred for 30 min. To the re-cooled (−60° C.) reaction mixture was added drop wise a solution of 1,12-dibromododecane (15.15 g, 0.04 mol) in dry THF (20 mL) and DMPU (2.8 mL, 0.02 mol). Then, the temperature was allowed to reach room temperature and was stirred at the same temperature over a period of 16 h. The resulting reaction mixture was quenched with saturated NH$_4$Cl (150 mL) at 0° C. and extracted with ether (200 mL×3). The organic phases were combined, dried over anhydrous Na$_2$SO$_4$ and the volatiles were evaporated under reduced pressure to obtain a pale, yellow liquid which was filtered through a silica gel (230-400) column (1.5% ethyl acetate in pet ether) to yield 15.0 g (crude) colorless oil. The compound was taken to the next step without further purification or characterization.

Step 3—Formic acid (75 mL, 5 vol) was added dropwise with vigorous stirring to the compound 3 (15.0 g, 0.03 mol) at 0° C. Then ice bath was removed and the reaction mixture was stirred at room temperature over a period of 16 hours. The resulting reaction mixture was diluted with toluene (50 mL) and evaporated azeotropically to remove formic acid. The azeotropic process was repeated three times. The residue obtained upon azeotropic evaporation was washed with diisopropylether (50 mL×3) to give a product as a white solid (3.5 g). The product was further purified by hot ethyl acetate wash to afford a white solid (2.5 g) (20%) having a mp of 135-140° C.;.

$^1$H NMR (DMSO-d6; δ (ppm): 0.67 (bs, 4H), 0.99-1.02 (m, 4H), 1.23 (bs, 16H), 1.40-1.43 (m, 8H), 12.00 (bs, 2H); $^{13}$C NMR (DMSO-d6, δ ppm): 15.11, 23.20, 27.75, 29.52, 29.74, 33.85 and 176.69.

Example 2

Preparation of 2,15-dicyclopropyl-hexadecanedioic acid di-tert-butyl ester

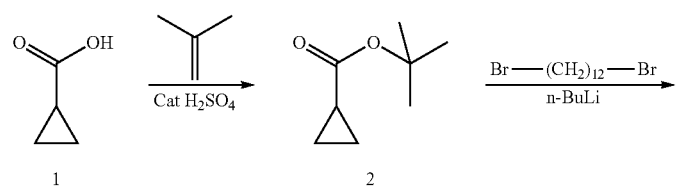

1                                                               2

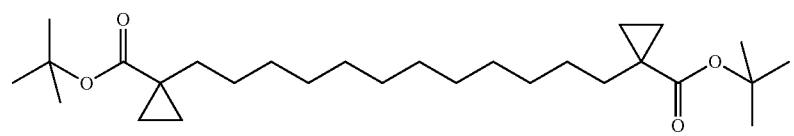

3

The compound was prepared following synthetic procedure described in Example 1.

Example 3

Preparation of {1-[10-(1-Ethoxycarbonylmethyl-cyclopropyl)-decyl]-cyclopropyl}-acetic acid ethyl ester

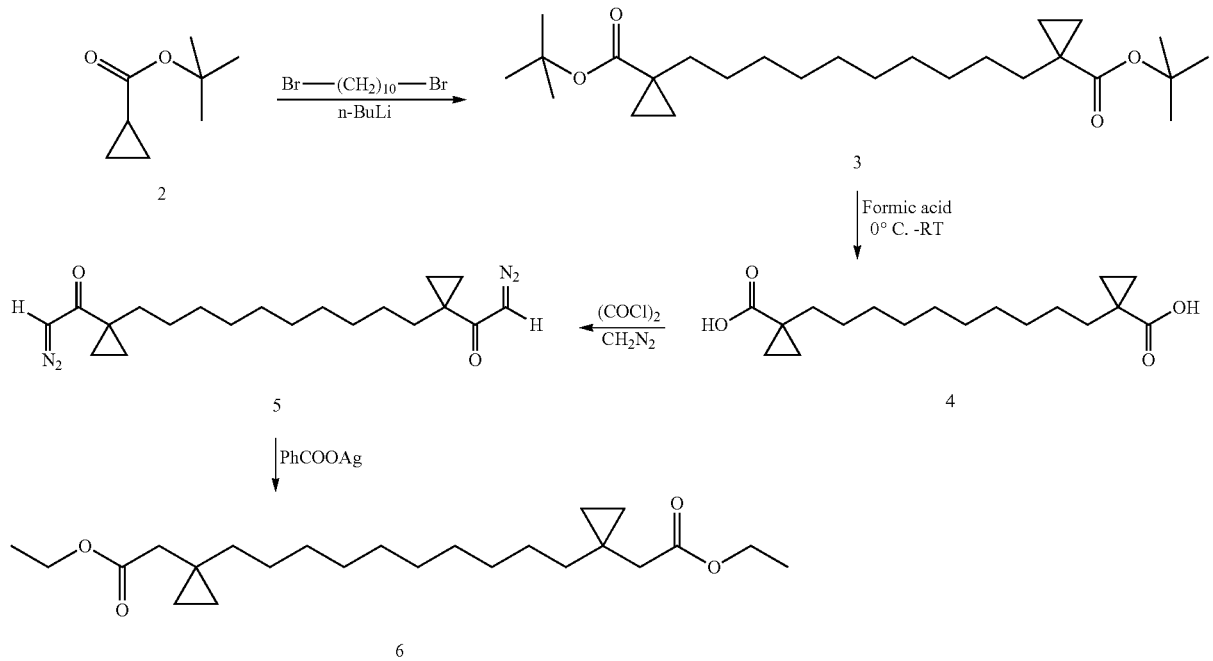

Step 1—A solution of n-butyl lithium in hexane (1.4M, 426 mL, 0.59 mol) was added dropwise to a solution of freshly distilled diisopropylamine (78.7 mL, 0.55 mol) in dry THF (560 mL) at −60° C. under a nitrogen atmosphere. The reaction mixture was slowly warmed to −20° C. and stirred for 30 min. The reaction mixture was re-cooled to −60° C. and cyclopropanecarboxylic acid tert-butyl ester (80 g, 0.55 mol) was added dropwise over a period of 30 min. The reaction mixture was slowly warmed to −20° C. and stirred for 30 min. To the re-cooled (−60° C.) reaction mixture was added drop wise 1,10-dibromododecane (42.1 g, 0.18 mol) in dry THF (56 mL) and DMPU (11.2 mL, 0.09 mol). Then, the temperature was allowed to reach room temperature and stirred at room temperature over a period of 16 hours. The resulting reaction mixture was quenched with saturated NH$_4$Cl (1.0 L) at 0° C. and extracted with ether (600 mL×3). The organic phases were combined, dried over anhydrous Na$_2$SO$_4$ and volatiles were removed under reduced pressure to yield a pale, yellow liquid which was filtered through a silica gel (230-400) column (1.5% ethyl acetate in pet ether) to yield 60.0 g crude (25%) colorless oil. The compound was taken to the next step without further purification or characterization.

Step 2—Formic acid (300 mL, 5 vol) was added dropwise with vigorous stirring to compound 3 (60.0 g, 0.14 mol) at 0° C. Then, the ice bath was removed and the reaction mixture was stirred at room temperature over a period of 16 hours. The resulting reaction mixture was diluted with toluene (200 mL) and evaporated azeotropically to remove formic acid. The azeotropic process was repeated three times. The residue obtained after azeotropic solvent removal was washed with diisopropylether (200 mL×3) to give product as white solid 19 g (43. %).

$^1$H NMR (DMSO-d6, δ ppm): 0.69 (bs, 4H), 0.99-1.02 (m, 4H), 1.23 (bs, 12H), 1.40-1.43 (m, 8H), 12.00 (bs, 2H).

Step 3—To a suspension of acid 4 (3.0 g, 0.01 mol) in dichloromethane (30 mL) was added oxalyl chloride (2.7 mL, 0.02 mol) and a catalytic amount of DMF (0.06 mL) at ice temperature. Then, the ice bath was removed and the reaction mixture was stirred at room temperature over a period of 1 hour. The crude product obtained upon evaporation of the volatiles was diluted with diethyl ether (20 mL), cooled to 0° C. and added to a solution of diazomethane (4.0 g, 0.09 mol) in ether (200 mL) at the same temperature. Then, the mixture was allowed to reach room temperature and was stirred at room temperature over a period of 16 hours. Excess of diazomethane was removed with a stream of nitrogen. The crude product obtained upon evaporation of the ether was diluted with ethyl acetate (200 mL), washed with water (200 mL) and brine (200 mL), and dried over sodium sulphate. The crude product obtained upon evaporation of ethyl acetate was purified by flash column chromatography to give product as a yellow solid (2.3 g) (67%).

$^1$H NMR (DMSO-d6, δ (ppm): 0.70 (bs, 4H), 1.00-1.03 (m, 4H), 1.24-1.34 (m, 16H), 1.46-1.51 (m, 4H), 6.17 (s, 2H).

Step 4—To a solution of diazo compound 5 (7.0 g, 19.5 mmol) in ethanol (50 mL) was added a freshly prepared solution of silver benzoate (3.5 g, 15.6 mmol) in triethylamine (10.0 mL) drop wise at reflux temperature. Then, the reaction mixture was refluxed over a period of 6 hours, allowed to cool room temperature and filtered.

The crude product obtained upon evaporation of the ether was diluted with ethyl acetate (500 mL), washed with 10% sodium bicarbonate (100 mL×2), water (100 mL), and brine (100 mL) and dried over sodium sulphate. The crude product obtained upon evaporation of ethyl acetate was purified by flash column chromatography to give a product as a pale, yellow oil (1.51 g) (19%).

¹H NMR (DMSO-d6, δ ppm): 0.34-0.38 (m, 4H), 0.42-0.45 (m, 4H), 1.22-1.33 (m, 26H), 2.34 (s, 4H), 4.14 (q, J=7.2 Hz, 4H).

Example 4

Synthesis of {1-[10-(1-carboxymethyl-cyclopropyl)-decyl]-cyclopropyl}-acetic acid

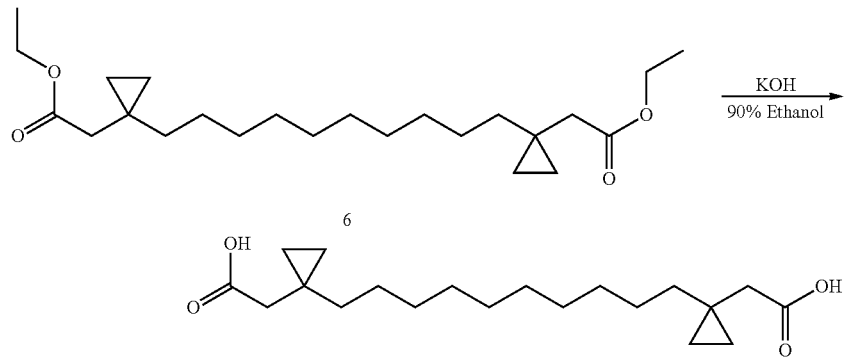

To a solution of KOH (2.7 g, 49.3 mmol) in 90% ethanol (50 mL) was added ester 6 (1.16 g, 2.90 mmol) at 80° C. and stirred at the same temperature over a period of 8.5 hours. The crude product obtained upon evaporation of the solvent was diluted with water (10 mL), acidified to pH=2 (1N HCl) and extracted with ethyl acetate (100 mL×2). The organic layer was dried over sodium sulphate and concentrated. The residue obtained was washed with n-hexane (50 mL×2) and dried under high vacuum to give product as an off-white solid (890 mg) (89%).

¹H NMR (DMSO-d6, δ ppm): 0.28 (bs, 4H), 0.36 (bs, 4H), 1.23-1.28 (m, 21H), 2.15 (s, 4H), 11.96 (bs, 2H). 13C NMR (DMSO-d6, δ ppm): 12.02, 17.50, 26.54, 29.51, 29.56, 29.72, 36.53 and 173.80

Example 5

Synthesis of 2,2,15,15-Dicyclopentyl-hexadecanedioic acid

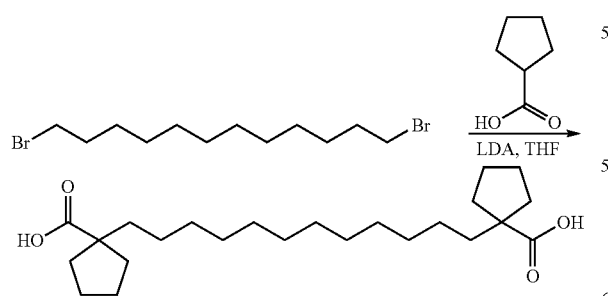

Cyclopentanecarboxylic acid (2.6 mL, 24.3 mmol) was added to a stirred solution of LDA (5.33 eq, generated by adding n-butyl lithium in hexane (1.6M, 35.0 mL, 48.7 mmol) to a solution of diisopropylamine (7.0 mL, 48.7 mmol) in THF at −78° C. under a nitrogen atmosphere) at −30° C. The reaction mixture was slowly warmed to room temperature and stirred for 3 hours. The reaction mixture was recooled to −10° C., followed by the rapid addition of 1,12-dibromododecane (3.0 g, 9.14 mmol) in THF (3.0 mL). The reaction mixture was slowly warmed to room temperature and stirred over a period of 16 hours.

The reaction mixture was quenched with a 12% HCl solution at 0° C. and extracted with benzene (2×25 mL). The organic layer was washed with water and brine solution, then dried over anhydrous Na₂SO₄ and evaporated under reduced pressure to obtain a crude product. The crude was purified by titrating with hexane at −70° C., filtered, and dried under vacuum to obtain product as an off-white solid (1.7 g) (47.22%) having a mp of 117-118° C.

¹H NMR (DMSO-d6, δ (ppm): 1.22 (bs, 20H), 1.32-1.40 (m, 4H), 1.49-1.53 (bs, 12H), 1.95-2.03 (m, 4H), 11.99 (bs, 2H).

Example 6

Synthesis of 2,11-Dicyclopropyl-dodecanedioic acid

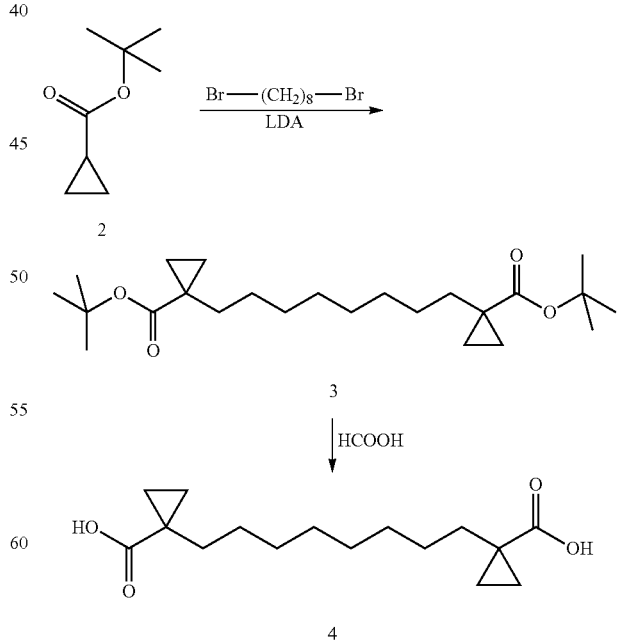

Step 1—A solution of n-butyl lithium in hexane (1.4M, 16.9 mL, 0.09 mol) was added drop wise to a solution of freshly distilled diisopropylamine (3.1 mL, 0.02 mol) in dry THF (20 mL) at −60° C. under a nitrogen atmosphere. The reaction mixture was slowly warmed to −20° C. and stirred for 30 min. The reaction mixture was re-cooled to −60° C. and cyclopropanecarboxylic acid tert-butyl ester (3.1 g, 0.02 mol) was added drop wise over a period of 10 min. The reaction mixture was slowly warmed to −20° C. and stirred for 30 min. To the re-cooled (−60° C.) above reaction mixture was added drop wise 1,8-dibromoctane (2.0 g, 7.0 mmol) in dry THF (5 mL) and DMPU (0.46 mL, 3.2 mmol). Then, the temperature was allowed to reach room temperature and stirred at the same temperature over a period of 16 hours. The resulting reaction mixture was quenched with saturated NH$_4$Cl (50 mL) at 0° C. and the reaction mixture extracted with ether (50 mL×3). The organic phases were combined, dried over anhydrous Na$_2$SO$_4$ and volatiles evaporated under reduced pressure to yield a pale, yellow liquid which was filtered through a silica gel (230-400) column (1.5% ethyl acetate in pet ether) to yield 1.96 g of a crude (70%) colorless oil. The compound was taken to the next step without further purification or characterization.

Step 2—Formic acid (6.0 mL, 10 vol) was added drop wise with vigorous stirring to the compound 3 (600 mg, 0.14 mol) at 0° C. Then, the ice bath was removed and the reaction mixture was stirred at room temperature over a period of 16 hours. The resulting reaction mixture was diluted with toluene (20 mL), followed by azeotropic distillation to remove formic acid. The azeotropic process was repeated three times. The residue obtained upon azeotropic evaporation was washed with diisopropylether (20 mL×3) to give a product as a white solid (110 mg) (26%).

$^1$H NMR (DMSO-d6, δ (ppm): 0.63-0.67 (m, 4H), 0.98-1.02 (m, 4H), 1.22 (bs, 8H), 1.40-1.43 (m, 8H), 12.00 (bs, 2H).

Example 7

Synthesis of 1-[8-(1-carboxymethyl-cyclopropyl)-octyl]-cyclopropyl}-acetic acid diethyl ester

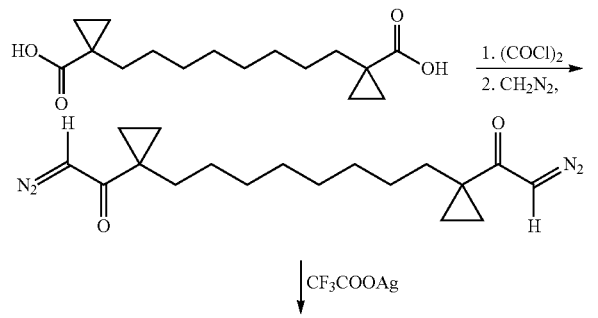

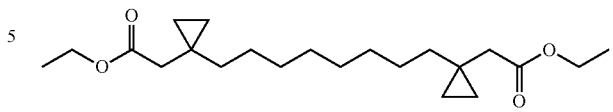

Step 1—To a suspension of product 4 of Example 6 (1.0 g, 3.54 mmol) in dichloromethane (10 mL) was added oxalyl chloride (1.0 mL, 10.6 mmol) and one drop of DMF at ice temperature. The reaction mixture was stirred at room temperature over a period of 1 hour. The crude product obtained upon evaporation of the volatiles was diluted with diethyl ether (20 mL) and cooled to 0° C. To the crude product was added a solution of diazomethane in ether (40 mL) at the same temperature. Then, the mixture was stirred at room temperature over a period of 12 hours. Excess diazomethane was removed with a stream of nitrogen. The crude product obtained upon evaporation of the ether was diluted with ethyl acetate (200 mL), washed with water (50 mL) and brine (50 mL), then dried over sodium sulphate. The crude product obtained upon evaporation of ethyl acetate was purified by flash column chromatography to give a product as a yellow solid (0.8 g) (68%).

$^1$H NMR (DMSO-d6, δ ppm): 0.69-0.73 (m, 4H), 0.99-1.03 (m, 4H), 1.17-1.13 (m, 12H), 1.40-1.51 (m, 4H), 6.17 (s, 2H).

Step 2: To a solution of diazo compound from Step 1 (0.8 g, 2.4 mmol) in ethanol (20 mL) was added a solution of silver triflate (300 mg, 1.35 mmol) in triethyl amine (1.5 mL) in a drop wise fashion at reflux temperature. The reaction mixture was refluxed for 6 hours, allowed to cool to room temperature, and filtered. The crude product obtained upon evaporation of the ethanol was diluted with ethyl acetate (200 mL), washed with 10% sodium bicarbonate (50 mL) and water (50 mL), and dried over sodium sulphate. The crude product obtained upon evaporation of ethyl acetate was purified by flash column chromatography to give a product as a yellow oil (0.2 g) (22%).

$^1$H NMR (DMSO-d6, δ ppm): 0.34-0.38 (m, 4H), 0.41-1.45 (m, 4H), 1.15-1.14 (m, 22H), 2.23 (s, 4H), 4.11-4.18 (m, 2H).

Example 8

Synthesis of {1-[8-(1-carboxymethyl-cyclopropyl)-octyl]-cyclopropyl}-acetic acid

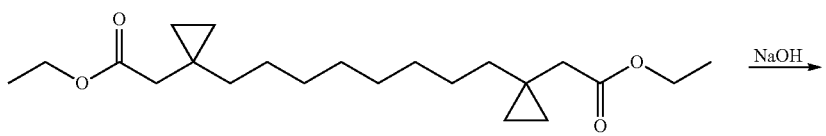

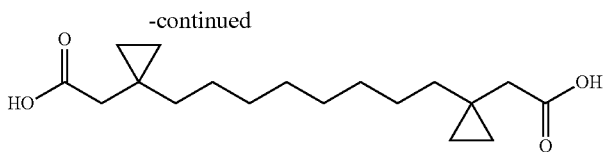

To a solution of KOH (0.5 g, 9.16 mmol) in 90% ethanol (10 mL) was added the product of Example 7 (0.2 g, 0.54 mmol) at 80° C. and stirred at same temperature over a period of 8.5 hours. The crude product obtained upon evaporation of the solvent was diluted with water (5 mL), acidified to pH=2 N HCl), extracted with ethyl acetate (500 mL×2), dried over sodium sulphate, and concentrated. The residue obtained was washed with n-hexane (10 mL×2) and dried under high vacuum to give a product as an off-white solid (115 mg) (68%) having a mp of 100.6-101.3° C.

$^1$H NMR (DMSO-d6, δ (ppm): 0.26-0.29 (m, 4H), 0.34-0.37 (m, 4H), 1.22-1.27 (m, 16H), 2.12 (m, 4H), 11.95 (bs, 2H).

Example 9

Synthesis of (2,15-Dicyclopropyl-hexadecanedioic acid monoethyl ester

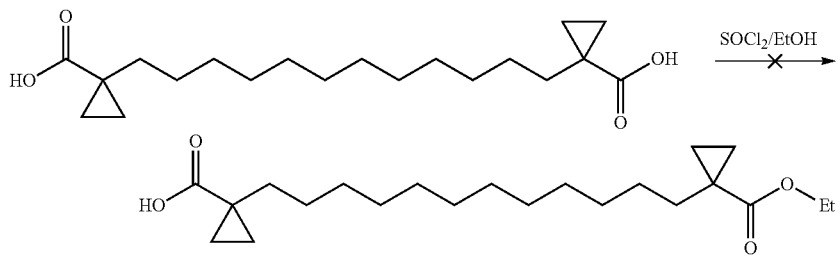

To a suspension of product of Example 1 (2.0 g, 5.9 mmol) in ethanol (20 mL) was added thionyl chloride (1.65 mL, 0.02 mol) in a dropwise fashion at ice temperature. The ice bath was removed and reaction mixture stirred at ambient temperature over a period of 16 h. The reaction mixture was filtered to remove unreacted starting material (0.6 gm) and residue obtained upon evaporation of the filtrate was purified by silica gel column chromatography (5% ethyl acetate in petroleum ether) to give product as a pale yellow liquid 100 mg. The pale yellow liquid solidified as an off-white solid upon storage; mp 36.9-38.2° C.

$^1$H NMR (300 MHz, DMSO-$d_6$) δ (ppm): 0.63-0.72 (m, 4H), 0.99-1.04 (m, 4H), 1.15 (t, J=7.2 Hz, 3H), 1.23 (bs, 16H), 1.40-1.46 (m, 8H), 4.02 (q, J=7.2 Hz, 2H), 11.99 (bs, 1H); MS 365.0 (M–H)

Example 10

Synthesis of 2,15-Dicyclopropyl-hexadecanedoic acid diethyl ester

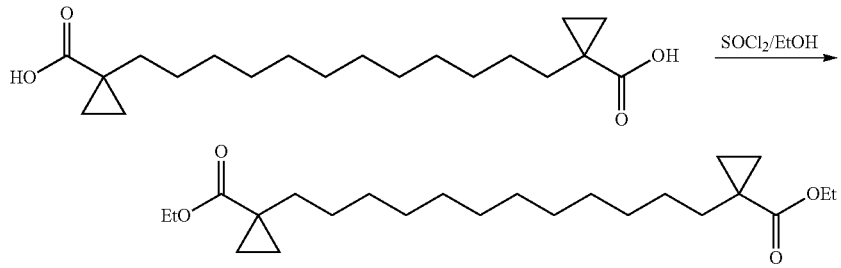

To a suspension of product of Example 1 (1.0 g, 2.9 mmol) in ethanol (10 mL) was added thionyl chloride (0.86 mL, 11.8 mmol) drop wise at ice temperature. The ice bath was removed and reaction mixture stirred at 80° C. over a period of 16 h. The crude product obtained upon evaporation of the volatiles was diluted with ethyl acetate (200 mL), washed with water (50 mL×3) and dried over sodium sulphate. The crude product obtained upon evaporation of the solvent was purified through silica gel (230-400) column (4% ethyl acetate in petroleum ether) to give product as pale yellow liquid 0.25 g (21.5%).

$^1$H NMR (300 MHz, DMSO-$d_6$) δ (ppm): 0.66-0.71 (m, 4H), 1.01-1.05 (m, 4H), 1.15 (t, J=7.2 Hz, 6H), 1.23 (bs, 16H), 1.36-1.49 (m, 8H), 4.02 (q, J=7.2 Hz, 2H). $^{13}$C NMR (75 MHz, DMSO-$d_6$) δ (ppm): 14.50, 15.32, 23.62, 27.62, 29.39, 29.46, 29.57, 33.57, 60.32 and 174.69. MS–395.0 (M+H)

Example 11

Synthesis of 1-[12-(1-Carbamoyl-cyclopropyl)-dodecyl]-cyclopropanecarboxylic acid ethyl ester

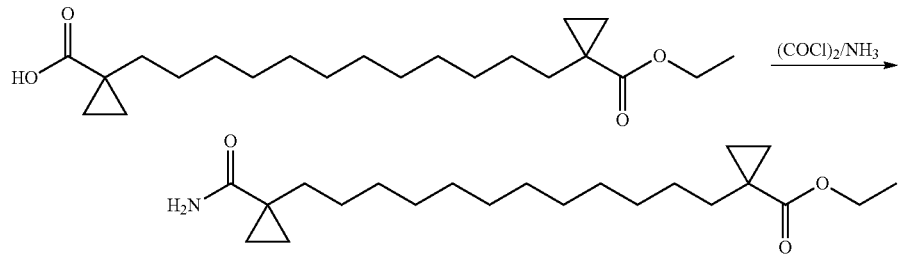

To a solution of product of Example 9 (1.5 g, 4.09 mmol) in dichloromethane (15 mL) was added oxalyl chloride (0.68 mL, 8.1 mmol) and catalytic amount of DMF (0.015 mL) at ice temperature. The ice bath was removed and reaction mixture stirred at room temperature over a period of 1 h. The crude product obtained upon evaporation of the solvent was diluted with DCM (10 mL), cooled to ice bath temperature and added ammoniated DCM (100 mL) drop wise fashion. Then reaction mixture was slowly allowed to reach room temperature and stirred for 2 h. The resulting reaction mass was diluted with ethyl acetate (250 mL), washed with water (100 mL×2) and dried over sodium sulphate. The residue obtained upon evaporation of the volatiles was purified by silica gel (230-400) column (40% ethyl acetate in petroleum ether) to give product as yellow oil 0.84 g (56%). The pale yellow oil solidified as off-white solid upon storage. mp: 49.5-51.2.2° C.

$^1$H NMR (300 MHz, DMSO-$d_6$) δ (ppm): 0.46 (bs, 2H), 0.70-0.71 (bs, 2H), 0.87 (bs, 2H), 1.02-1.03 (bs, 2H), 1.48 (t, J=6.9 Hz, 3H), 1.23 (bs, 16H), 1.30-1.44 (m, 8H), 4.01 (q, J=6.9 Hz, 2H), 6.79 (bs, 1H, $D_2O$ exchangeable 1H), 6.99 (bs, $^1$H, $D_2O$ exchangeable $^1$H). $^{13}$C NMR (75 MHz, DMSO-$d_6$) δ (ppm): 13.77, 24.70, 27.79, 29.52, 29.63, 34.36 and 175.92. MS: 366 (M+H)

Example 12

Synthesis of (1-[12-(1-Carbamoyl-cyclopropyl)-dodecyl]-cyclopropanecarboxylic acid

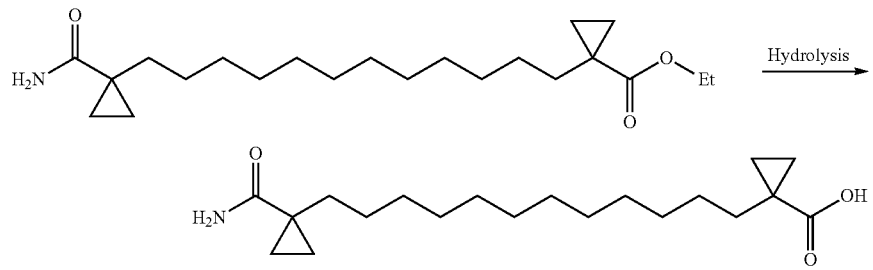

To a solution of KOH (0.9 g, 16.0 mmol) in 90% ethanol (25 mL) was added product of Example 11 (0.7 g, 1.9 mmol) at 80° C. and stirred at same temperature for 8.5 h. The crude product obtained upon evaporation of the solvent was diluted with water (2.0 mL), acidified to pH=2 (1N HCl), and extracted with ethyl acetate (100 mL×2). The organic layer was dried over sodium sulphate and concentrated. The residue obtained was washed with n-hexane (20.0 mL×2) and dried under high vacuum to give product as white solid 470 mg (73%); mp: 116.6-118.1° C.

$^1$H NMR (300 MHz, DMSO-d$_6$) δ (ppm): 0.45-0.48 (m, 2H), 0.63-0.67 (m, 2H), 0.86-0.89 (m, 2H), 0.99-1.02 (m, 2H), 1.30 (bs, 18H), 1.32-1.46 (m, 6H), 6.78 (bs, 1H, —CONH$_2$; D$_2$O exchangeable), 6.98 (bs, 1H, —CONH$_2$; D2O exchangeable), 11.99 (s, 1H, —COOH, exchangeable $^1$H). $^{13}$C NMR (75 MHz, DMSO-d$_6$) δ (ppm): 13.83, 15.11, 23.30, 24.66, 27.75, 27.84, 29.53, 29.66, 29.74, 33.85, 34.35, 175.93 and 176.69. MS-338.0 (M+H)

Example 13

Synthesis of 1-[12-(1-Hydroxymethyl-cyclopropyl)-dodecyl]-cyclopropanecarboxylic acid

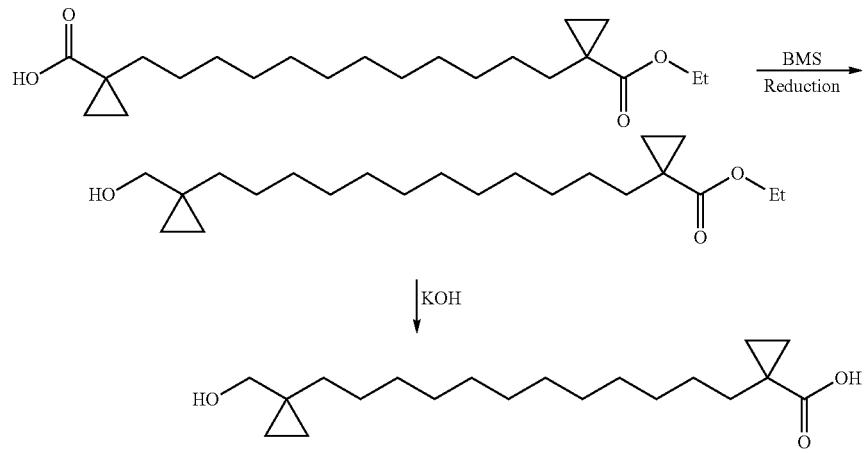

Step 1: To a solution of product of Example 9 (0.5 g, 1.3 mmol) in dry THF (10 mL, 20 vol) was added boranedimethyl sulfide (0.64 mL, 6.8 mmol) at ice bath temperature. After 10 min, ice bath was removed and the reaction mixture stirred at room temperature over a period of 16 h. The resulting reaction mixture was quenched with saturated ammonium chloride (20 mL) at ice bath temperature and extracted with ethyl acetate (50 mL×3). The combined organic layer was washed with water (50 mL×3), brine (50 mL) and dried over sodium sulphate. The residue obtained upon evaporation of the volatiles was purified by silica gel (230-400) column (15% ethyl acetate in petroleum ether) to give product as yellow oil 0.3 g (62%).

$^1$H NMR (300 MHz, DMSO-d$_6$) δ (ppm): 0.14-0.18 (m, 2H), 0.22-0.30 (m, 2H), 0.68-0.82 (m, 2H), 1.01-1.07 (m, 2H), 1.10-1.48 (m, 27H), 3.19 (d, J=5.7 Hz, 2H), 3.96-4.05 (m, 2H), 4.37 (t, J=5.7 Hz, 1H)

Step 2: To a solution of KOH (0.4 g, 4.5 mmol) in 90% ethanol (15 mL) was added ester of step 1 (0.3 g, 0.8 mmol) at 80° C. and stirred at same temperature over a period of 8.5 h. The crude product obtained upon evaporation of the solvent was diluted with water (3.0 mL), acidified to pH=2 (1N HCl), and extracted with ethyl acetate (100 mL×2). The organic layer was dried over sodium sulphate and concentrated. The residue obtained was washed with n-hexane (10.0 mL×2) and dried under high vacuum to give product as white solid 240 mg (88%). mp −73.6-75.3° C.

$^1$H NMR (300 MHz, DMSO-d$_6$) δ (ppm): 0.15-0.18 (m, 2H), 0.27-0.30 (m, 2H), 0.63-0.67 (m, 2H), 0.99-1.02 (m, 2H), 1.15-1.28 (m, 20H), 1.35-1.40 (m, 4H), 3.19 (d, J=5.1 Hz, 2H), 4.37 (t, J=5.4 Hz, 1H, —OH; D$_2$O exchangeable 1H), 11.99 (s, 1H, —COOH; D$_2$O exchangeable).

$^{13}$C NMR (75 MHz, DMSO-d$_6$) δ (ppm): 9.88, 15.10, 22.19, 23.29, 26.61, 27.75, 29.54, 29.64, 29.76, 29.96, 33.86, 34.33, 66.05, 176.66. MS 323.0 (M−H)

Example 14

Preparation of 1-[12-(1-Methoxymethyl-cyclopropyl)-dodecyl]-cyclopropanecarboxylic acid ethyl ester

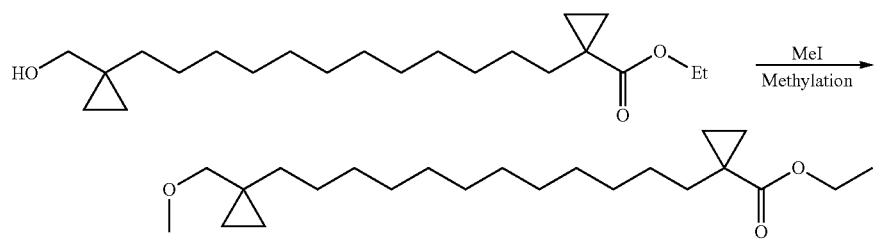

To a solution of product of Step 1, Example 13 (0.4 g, 1.1 mmol) in dry DMF (2 mL) was added 60% sodium hydride (45 mg, 1.1 mmol) at ice bath temperature under nitrogen atmosphere. Methyl iodide (0.14 mL, 2.2 mmol) was added drop wise at ice bath temperature. After 10 min ice bath was removed and allowed to stir at room temperature over a period of 2 h. The resulting reaction mixture was quenched with ice water and diluted with ethyl acetate (200 mL). The ethyl acetate layer was washed with water (50 mL, ×2), brine (50 mL) and dried over sodium sulphate. The crude product obtained upon evaporation of the solvent was purified by chromatography (10% ethyl acetate in petroleum ether) to give product as pale yellow oil 400 mg (96%).

$^1$H NMR (300 MHz, DMSO-$d_6$) δ (ppm): 0.20-0.32 (m, 4H), 0.68-0.72 (m, 2H), 1.01-1.04 (m, 2H), 1.12-1.46 (m, 27H), 3.11 (s, 2H), 3.21 (s, 3H), 3.98-4.05 (m, 2H).

Example 15

Preparation of 1-[12-(1-Methoxymethyl-cyclopropyl)-dodecyl]-cyclopropanecarboxylic acid

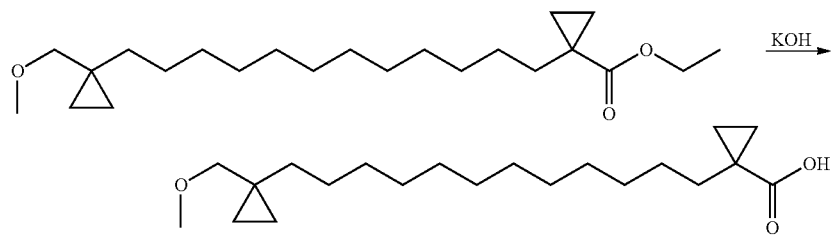

To a solution of KOH (0.5 g, 9.1 mmol) in 90% ethanol (20 mL) was added product of Example 14 (0.4 g, 1.0 mmol) at 80° C. and stirred at same temperature over for 8.5 h. The crude product obtained upon evaporation of the solvent was diluted with water (5.0 mL), acidified to pH=2 (1N HCl), and extracted with ethyl acetate (50 mL×2). The organic layer was dried over sodium sulphate and concentrated. The residue obtained was washed with n-hexane (10.0 mL×2) and dried under high vacuum to give product as white solid 350 mg (94%). mp. 36.4-37.6° C.

$^1$H NMR (300 MHz, DMSO-$d_6$) δ (ppm): 0.22-0.32 (m, 4H), 0.63-0.66 (m, 2H), 0.99-1.02 (m, 2H), 1.23-1.27 (m, 20H), 1.40 (bs, 4H), 3.11 (s, 2H), 3.21 (s, 3H), 11.99 (bs, 1H, —COOH; D2O exchangeable). $^{13}$C NMR (75 MHz, DMSO-$d_6$) δ (ppm): 10.23, 15.09, 19.89, 23.29, 26.57, 27.75, 29.52, 29.58, 29.76, 29.85, 33.87, 34.50, 58.29, 77.45, 176.65. MS 337.0 (M–H)

Example 16

Synthesis of 2,15-Cyclobutyl-hexadecanedioic acid

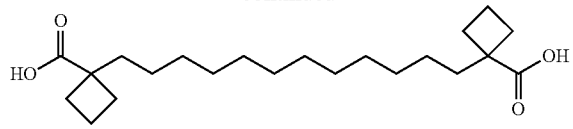

A solution of n-butyl lithium in hexane (1.4M, 46 mL, 0.06 mol) was added drop wise to a solution of freshly distilled diisopropylamine (10.0 mL, 0.06 mol) in dry THF (50 mL) at −60° C. under nitrogen atmosphere. The reaction mixture was slowly warmed to −20° C. and stirred for 30 min. The reaction mixture was re-cooled to −60° C. and cyclobutane carboxylic acid (3.2 g, 0.03 mol) added drop wise over a period 10 min. Reaction mixture was slowly warmed to −20° C. and stirred for 30 min. To the re-cooled (−60° C.) reaction mixture was added drop wise 1,12-dibromododecane (4.0 g, 0.01 mol) in dry THF (4 mL). Then the temperature was allowed to reach room temperature and stirred at same temperature over a period of 16 h. The resulting reaction mixture was quenched with saturated NH4Cl (100 mL) at 0° C. and the reaction mixture was extracted with ethyl acetate (100 mL×3). The organic phases were combined, dried over anhydrous Na2SO4 and volatiles were evaporated under reduced pressure to yield a pale yellow liquid which was purified through silica gel (230-400) column (8% ethyl acetate in petroleum ether) to give product as a white solid 160 mg (3.6%). mp: 99.8-100.3° C.

$^1$H NMR (300 MHz, DMSO-$d_6$) δ (ppm): 1.11-1.14 (m, 4H), 1.23 (m, 16H), 1.64-1.66 (m, 4H), 1.69-1.84 (m, 8H), 2.22-2.30 (m, 4H), 12.03 (s, 2H, —COOH; D$_2$O exchangeable). $^{13}$C NMR (75 MHz, DMSO-$d_6$) δ (ppm): 15.49, 24.93, 29.44, 29.46, 29.49, 29.77, 29.98, 38.01, 47.41, 178.41. MS: 365.0 (M–H)

Example 17

Synthesis of 2,14-Dicyclopropyl-pentadecanedioic acid

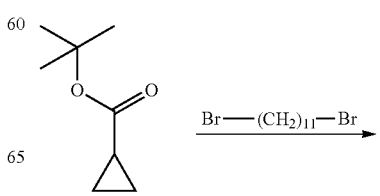

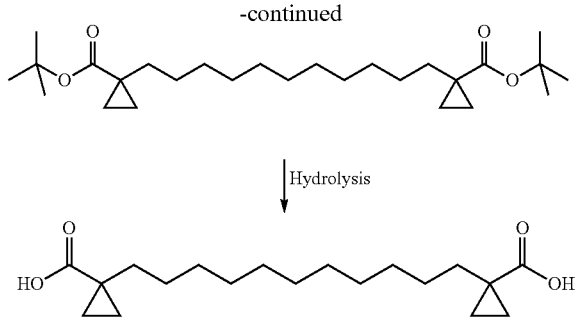

Step 1: A solution of n-butyl lithium in hexane (1.6M, 114 mL, 0.18 mol) was added drop wise to a solution of freshly distilled diisopropylamine (26.4 mL, 0.17 mol) in dry THF (180 mL) at −60° C. under nitrogen atmosphere. The reaction mixture was slowly warmed to −20° C. and stirred for 30 min. The reaction mixture was re-cooled to −60° C. and cyclopropanecarboxylic acid tert-butyl ester (24.4 g, 0.17 mol) added drop wise over a period 30 min. Reaction mixture was slowly warmed to −20° C. and stirred for 30 min. To the re-cooled (−60° C.) reaction mixture was added drop wise 1,11-dibromoundecane (18.0 g, 0.05 mol) in dry THF (18 mL) and DMPU (3.6 g, 0.02 mol). Then the temperature was allowed to reach room temperature and stirred at same temperature over a period of 16 h. The resulting reaction mixture was quenched with saturated NH4Cl (500 mL) at 0° C. and the reaction mixture was extracted with ethyl acetate (300 mL×2). The organic phases were combined, dried over anhydrous Na$_2$SO$_4$ and volatiles were evaporated under reduced pressure to yield a pale yellow liquid which was filtered through silica gel (230-400) column (1.5% ethyl acetate in petroleum ether) to give 24 g (96%) crude product as colorless oil. The product obtained was taken to next step without characterization.

Step 2: Formic acid (240 mL, 10 vol) was added drop wise with vigorous stirring to the compound of Step 1 (24.0 g, 0.05 mol) at 0° C. Then ice bath was removed and reaction mixture stirred at room temperature over a period of 16 h. The resulting reaction mixture was diluted with toluene (200 mL) and evaporated azeotropically to remove formic acid. The azeotropic evaporation was repeated three times. The residue obtained upon azeotropic evaporation was washed with diisopropylether (100 mL×3) to give product as white solid 5.0 g (28%). mp: 114.7-117.7° C.

$^1$H NMR (300 MHz, DMSO-d$_6$) δ (ppm): 0.63-0.67 (m, 4H), 0.99-1.23 (m, 4H), 1.23 (s, 14H), 1.40 (bs, 8H), 12.00 (bs, 2H, —COOH, D$_2$O exchangeable).

$^{13}$C NMR (75 MHz, DMSO-d$_6$) δ (ppm): 15.10, 23.30, 27.75, 29.51, 29.74, 33.85, 176.68. MS: 323.0 (M−H).

Example 18

Synthesis of 1-[10-(1-Carboxymethyl-cyclobutyl)-decyl]-cyclopropanecarboxylic acid

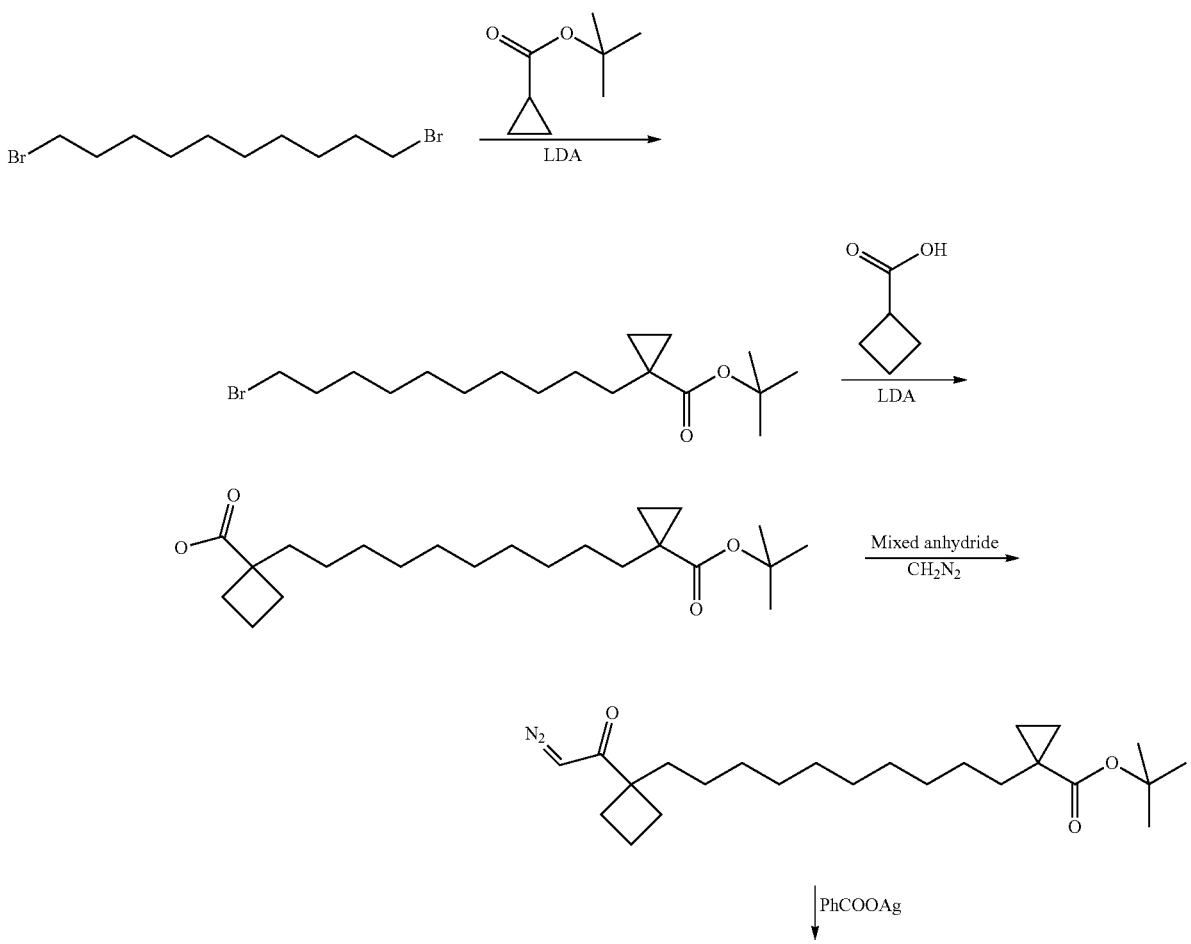

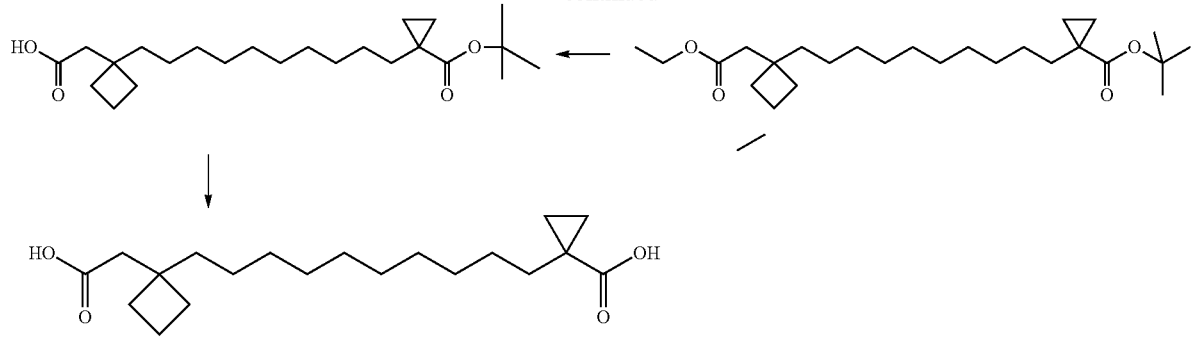

Step 1: A solution of n-butyl lithium in hexane (1.4M, 45.75 mL, 0.07 mol) was added drop wise to a solution of freshly distilled diisopropylamine (10.2 mL, 0.06 mol) in dry THF (200 mL) at −60° C. under nitrogen atmosphere. The reaction mixture was slowly warmed to −20° C. and stirred for 30 min. The reaction mixture was re-cooled to −60° C. and cyclopropanecarboxylic acid tert-butyl ester (9.48 g, 0.06 mol) added drop wise over a period 30 min. Reaction mixture was slowly warmed to −20° C. and stirred for 30 min. To the re-cooled (−60° C.) reaction mixture was added drop wise 1,10-dibromodecane (20.0 g, 0.06 mol) in dry THF (20 mL) and DMPU (1.79 g, 0.01 mol). Then the temperature was allowed to reach room temperature and stirred at same temperature over a period of 16 h The resulting reaction mixture was quenched with saturated NH$_4$Cl (500 mL) at 0° C. and the reaction mixture was extracted with ethyl acetate (300 mL×3). The organic phases were combined, dried over anhydrous Na$_2$SO$_4$ and volatiles were evaporated under reduced pressure to yield a pale yellow liquid which was purified through silica gel (230-400) column (0.5% ethyl acetate in petroleum ether) to give product as colorless oil 8.0 g (33%).

$^1$H NMR (300 MHz, DMSO-d$_6$) δ (ppm): 0.62-0.64 (m, 2H), 0.94-0.98 (m, 2H), 1.25 (bs, 12H), 1.37 (s, 9H), 1.39-1.43 (m, 4H), 1.73-1.80 (m, 2H), 3.52 (t, J=6.6 Hz, 2H).

Step 2: A solution of n-butyl lithium in hexane (1.4M, 84.2 mL, 0.11 mol) was added drop wise to a solution of freshly distilled diisopropylamine (18.4 mL, 0.11 mol) in dry THF (100 mL) at −78° C. under nitrogen atmosphere. The reaction mixture was slowly warmed to −30° C. and stirred for 30 min. To the reaction mixture cyclobutaric acid (5.88 g, 0.05 mol) added drop wise over a period 30 min. Reaction mixture was slowly warmed to room temperature and stirred for 3 h To the re-cooled (−10° C.) reaction mixture was added drop wise product of Step 1 (8.0 g, 0.02 mol) in dry THF (6.6 mL). Then the temperature was allowed to reach room temperature and stirred at same temperature over a period of 16 h. The resulting reaction mixture was quenched with saturated NH$_4$Cl (200 mL) at 0° C. and the reaction mixture was extracted with ethyl acetate (500 mL). The organic phases were combined, dried over anhydrous Na$_2$SO$_4$ and volatiles were evaporated under reduced pressure to yield a pale yellow liquid which was purified through silica gel (230-400) column (1% ethyl acetate in petroleum ether) to give product as colorless pale yellow oil 2.0 g (23%).

$^1$H NMR (300 MHz, DMSO-d$_6$) δ (ppm): 0.62-0.68 (m, 2H), 0.91-1.01 (m, 2H), 1.10-1.25 (m, 2H), 1.37-1.39 (bs, 13H), 1.42-1.45 (bs, 12H), 1.64-1.69 (m, 2H), 1.73-1.84 (m, 4H), 2.41-2.30 (m, 2H), 12.03 (bs, 1H).

Step 3: To a suspension of product of Step 2 (2.0 g, 5.2 mmol) in dry THF (20 mL) was added triethyl amine (0.73 mL, 5.2 mmol) at ice temperature. After 15 min ethyl chloroformate (0.5 mL, 5.2 mmol) was added and the reaction mixture was stirred at same temperature over a period of 15 min. The resultant reaction mixture cooled to 0° C. and a solution of diazomethane (2.2 g, 0.05 mol) in ether (250 mL) was added. Then the mixture was allowed to reach room temperature and stirred over a period of 16 h. Excess of diazomethane was removed with steam of nitrogen, the crude product obtained upon evaporation of the ether was diluted with ethyl acetate (500 mL), washed with water (100 mL×2), brine (100 mL) and dried over sodium sulphate. The crude product obtained upon evaporation of ethyl acetate was purified by flash column chromatography (4% ethyl acetate in petroleum ether) to give product as yellow liquid 0.51 g (24%).

$^1$H NMR (300 MHz, DMSO-d$_6$) δ (ppm): 0.55-0.63 (m, 2H), 1.08-1.12 (m, 2H), 1.26 (m, 15H), 1.43-1.48 (m, 12H), 1.64-1.69 (m, 2H), 1.72-1.91 (m, 4H), 2.34-2.38 (m, 2H), 5.21 (s, 1H).

Step 4: To a solution of diazo compound from Step 3 (0.51 g, 1.2 mmol) in ethanol (20 mL) was added a freshly prepared solution of silver benzoate (0.22 g, 0.9 mmol) in triethyl amine (1.0 mL) in a drop wise fashion at reflux temperature. Then the reaction mixture was refluxed over a period of 16 h, allowed to cool room temperature and filtered. The crude product obtained upon evaporation of the ethanol was diluted with ethyl acetate (200 mL), washed with 10% sodium bicarbonate (50 mL), water (50 mL), brine (50 mL) and dried over sodium sulphate. The crude product obtained upon evaporation of ethyl acetate was purified by flash column chromatography (2% ethyl acetate in petroleum ether) to give product 0.128 g (35%) as pale yellow oil.

$^1$H NMR (300 MHz, DMSO-d$_6$) δ (ppm): 0.62-0.68 (m, 2H), 0.97-0.99 (m, 2H), 1.14-1.39 (m, 17H), 1.43-1.46 (m, 15H), 1.70-1.90 (m, 6H), 2.37 (s, 2H), 4.03 (q, J=7.2 Hz, 2H).

Step 5: To a solution of KOH (0.2 g, 3.5 mmol) in 90% ethanol (10 mL) was added product of Step 4 (0.18 g, 0.4 mmol) at 80° C. and stirred at same temperature over a period of 8.5 h. The crude product obtained upon evaporation of the solvent was diluted with water (2.0 mL), acidified to pH=2 (1N HCl), and extracted with ethyl acetate (50 mL×2). The organic layer was dried over sodium sulphate and concentrated. The residue obtained 150 mg (89%) was taken to next step without further purification and characterization.

Step 6: Formic acid (1.5 mL, 10 vol) was added drop wise with vigorous stirring to the product of Step 5 (0.15 g, 0.3 mmol) at 0° C. Then ice bath was removed and reaction mixture stirred at room temperature over a period of 16 h. The resulting reaction mixture was diluted with toluene (4 mL) and evaporated azeotropically to remove formic acid. The azeotropic evaporation was repeated three times. The residue obtained upon azeotropic evaporation was washed with diisopropylether (5 mL×3) to give product as Off-white solid 120 mg (83%). mp: 62.0° C.-63.9° C.

$^1$H NMR (300 MHz, DMSO-d$_6$) δ (ppm): 0.63-0.67 (m, 2H), 1.00-1.09 (m, 2H), 1.23 (bs, 14H), 1.40-1.49 (m, 6H), 1.71-1.89 (m, 6H), 2.30 (s, 2H), 11.93-12.09 (bs, 2H, COOH exchangeable $^1$H). $^1$H NMR (300 MHz, DMSO-d$_6$-D$_2$O) δ (ppm): 0.63-0.67 (m, 2H), 0.99-1.01 (m, 2H), 1.23 (bs, 14H), 1.40-1.48 (m, 6H), 170-1.88 (m, 6H), 2.30 (s, 2H).

Example 19

Preparation of 1-[12-(1-Cyano-cyclopropyl)-dodecyl]-cyclopropanecarboxylic acid $^1$H NMR (300 MHz, DMSO-d$_6$) δ (ppm): 1.55-1.61 (m, 2H), 1.08-1.12 (m, 2H), 1.35 (bs, 13H), 1.49 (bs, 16H), 1.64-1.89 (m, 2H), 3.42 (t, J=6.9 Hz, 2H).

Step 2: A solution of n-butyl lithium in hexane (1.4M, 58.7 mL, 0.08 mol) was added drop wise to a solution of freshly distilled diisopropylamine (11.8 mL, 0.07 mol) in dry THF (100 mL) at −60° C. under nitrogen atmosphere. The reaction mixture was slowly warmed to −20° C. and stirred for 30 min. The reaction mixture was re-cooled to −78° C. and cyclopropane carbonitrile (5.17 g, 0.07 mol) added drop wise over a period 30 min and stirred at same temperature over a period of 1 h. To the reaction mixture was added drop wise product of Step 1 (10.0 g, 0.02 mol) in dry THF (40 mL) and DMPU (1.6 g, 0.01 mol). After 2 h stirring at −78° C. the reaction mixture was slowly allowed to reach room temperature and continued stirring over a period of 16 h. The resulting reaction mixture

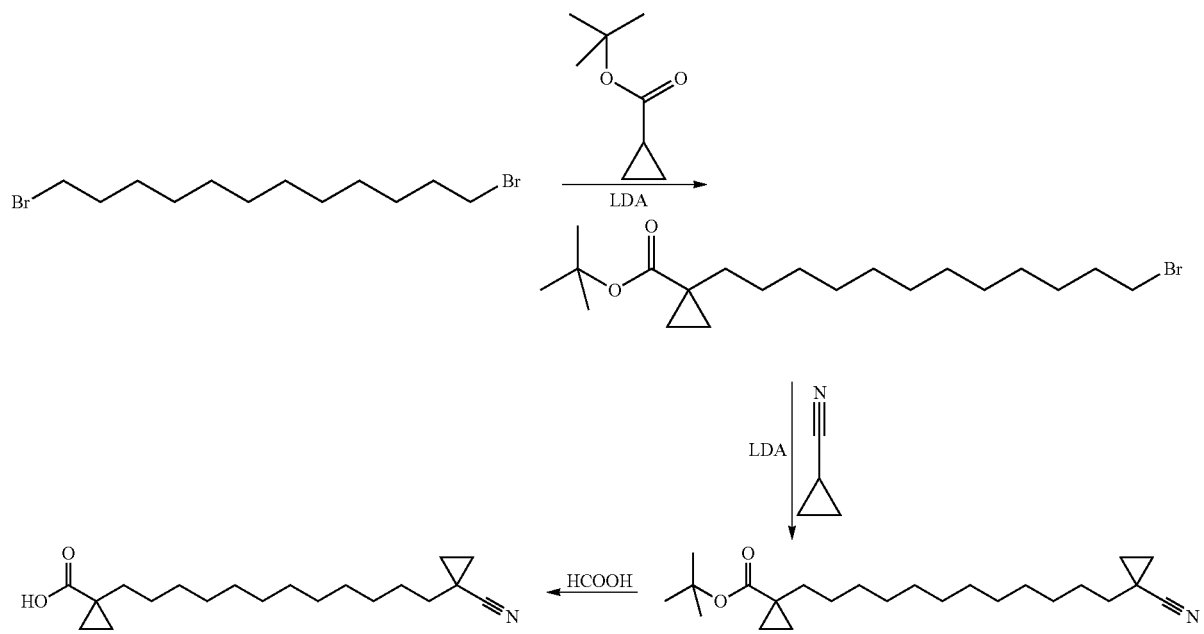

Step 1: A solution of n-butyl lithium in hexane (1.4M, 95.7 mL, 0.13 mol) was added drop wise to a solution of freshly distilled diisopropylamine (18.75 mL, 0.12 mol) in dry THF (400 mL) at −60° C. under nitrogen atmosphere. The reaction mixture was slowly warmed to −20° C. and stirred for 30 min. The reaction mixture was re-cooled to −60° C. and cyclopropanecarboxylic acid tert-butyl ester (17.34 g, 0.12 mol) added drop wise over a period 30 min. Reaction mixture was slowly warmed to −20° C. and stirred for 30 min. To the re-cooled (−60° C.) reaction mixture was added drop wise 1,12-dibromododecane (40.0 g, 0.12 mol) in dry THF (40 mL) and DMPU (3.12 g, 0.02 mol). Then the temperature was allowed to reach room temperature and stirred at same temperature over a period of 16 h. The resulting reaction mixture was quenched with saturated NH$_4$Cl (500 mL) at 0° C. and the reaction mixture was extracted with ethyl acetate (400 mL×3). The organic phases were combined, dried over anhydrous Na$_2$SO$_4$ and volatiles were evaporated under reduced pressure to yield a pale yellow liquid which was purified through silica gel (230-400) column (0.5% ethyl acetate in petroleum ether) to give product as pale yellow liquid 14.0 g (29%).

was quenched with saturated NH$_4$Cl (250 mL) at 0° C. and the reaction mixture was extracted with ethyl acetate (300 mL×2). The organic phases were combined, dried over anhydrous Na$_2$SO$_4$ and volatiles were evaporated under reduced pressure to yield a pale yellow liquid which was purified through silica gel (230-400) column (0.5% ethyl acetate in petroleum ether) to give product as pale yellow liquid 2.0 g (20%). The crude product so obtained was used in next step without further purification.

Step 3: Formic acid (20 mL, 10 vol) was added drop wise with vigorous stirring to the product of Step 2 (2.0 g, 5.3 mmol) at 0° C. Then ice bath was removed and reaction mixture stirred at room temperature over a period of 16 h. The resulting reaction mixture was diluted with toluene (20 mL) and evaporated azeotropically to remove formic acid. The azeotropic evaporation was repeated three times. The residue obtained upon azeotropic evaporation was purified through silica gel column chromatography (7% ethyl acetate in petroleum ether) to give product as Off-white solid 620 mg (36%). mp: 44.4° C.-46.9° C.

$^1$H NMR (300 MHz, DMSO-d$_6$) δ (ppm): 0.64-0.68 (m, 2H), 0.84-1.86 (m, 2H), 1.00-1.02 (m, 2H), 1.12-1.16 (m, 2H), 1.24 (bs, 16H), 1.40-1.43 (m, 8H), 11.99 (bs, 1H, COOH exchangeable $^1$H). MS 318 (M−H)

Example 20

Synthesis of 1-{12-[1-(1H-Tetrazol-5-yl)-cyclopropyl]-dodecyl}-cyclopropanecarboxylic acid

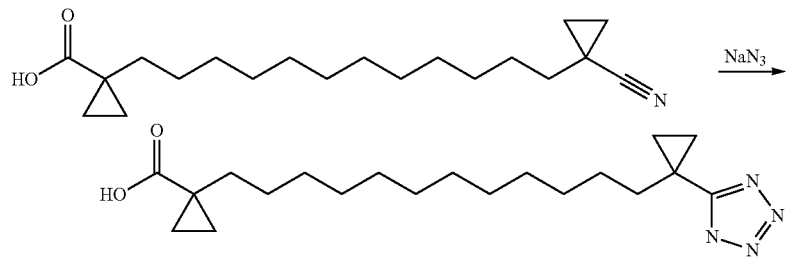

To a solution of Step 3 product of Example 19 (0.38 g, 1.8 mmol) in nitrobenzene (4 mL) were added sodium azide (0.46 g, 7.1 mmol) and triethyl amine hydrochloride (0.98 g, 7.1 mmol) at room temperature. The reaction mixture was allowed to stir at 130° C. over a period of 24 h. The reaction mixture was diluted with diethyl ether (50 mL) and extracted with 2% NaOH solution (50 mL×2). The combined aqueous layer was acidified to $P^H$=5 (1N HCl), extracted with ethyl acetate (50 mL×2), dried over sodium sulphate. The residue obtained upon evaporation of the solvent was purified through silica gel (230-400) column (50% ethyl acetate in petroleum ether) to give product as Off-white solid 120 mg (27%). mp −133.2° C.-135.0° C.

$^1$H NMR (300 MHz, DMSO-d$_6$) δ (ppm): 0.63-0.67 (m, 2H), 0.99-1.02 (m, 4H), 1.08-1.15 (m, 2H), 1.22 (bs, 18H), 1.40 (bs, 4H), 1.70-1.75 (m, 2H), 11.97-12.14 (bs, 1H, COOH exchangeable $^1$H). $^1$H NMR (300 MHz, DMSO-d$_6$-D$_2$O) δ (ppm): 0.64-0.68 (m, 0.99-1.06 (m, 6H), 1.16 (bs, 18), 1.30-1.36 (bs, 4H), 1.66-1.71 (m, 2H). $^{13}$C NMR (75 MHz, DMSO-d$_6$) δ (ppm): 15.12, 15.43, 16.41, 23.32, 27.26, 27.75, 29.40, 29.48, 29.72, 33.83, 35.38, 160.48, and 176.71. MS: 361.5 (M−H)

Example 21

Preparation of 2,13-dicyclopropyll-tetradecanedioic acid

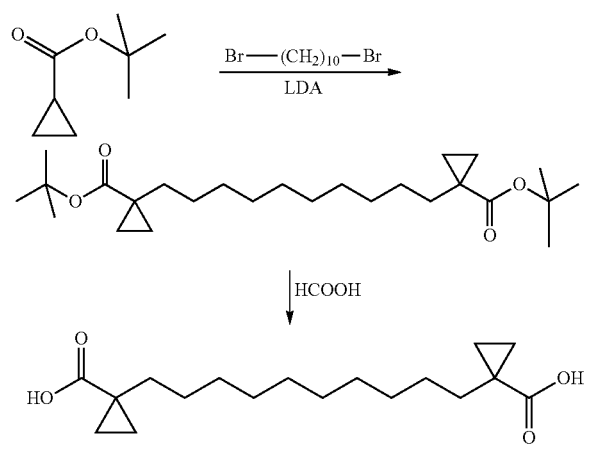

Step 1: A solution of n-butyl lithium in hexane (1.4M, 22.8 mL, 0.32 mol) was added drop wise to a solution of freshly distilled diisopropylamine (46.0 mL, 0.30 mol) in dry THF (300 mL) at −60° C. under nitrogen atmosphere. The reaction mixture was slowly warmed to −20° C. and stirred for 30 min. The reaction mixture was re-cooled to −60° C. and cyclopropanecarboxylic acid tert-butyl ester (42.6 g, 0.30 mol) added drop wise over a period 30 min. Reaction mixture was slowly warmed to −20° C. and stirred for 30 min. To the re-cooled (−60° C.) reaction mixture was added drop wise 1,10-dibromodecane (30.0 g, 0.10 mol) in dry THF (30 mL) and DMPU (6.4 g, 0.05 mol). Then the temperature was allowed to reach room temperature and stirred at same temperature over a period of 16 h. The resulting reaction mixture was quenched with saturated NH$_4$Cl (500 mL) at 0° C. and the reaction mixture was extracted with ethyl acetate (300 mL×3). The organic phases were combined, dried over anhydrous Na$_2$SO$_4$ and volatiles were evaporated under reduced pressure to yield a pale yellow liquid which was filtered through silica gel (230-400) column (1.5% ethyl acetate in petroleum ether) to give 28 g (66%) crude product as colorless oil. The product obtained was taken to next step without characterization.

Step 2: Formic acid (140 mL, 5 vol) was added drop wise with vigorous stirring to the product of Step 1 (28.0 g, 0.06 mol) at 0° C. Then ice bath was removed and reaction mixture stirred at room temperature over a period of 16 h. The resulting reaction mixture was diluted with toluene (100 mL) and evaporated azeotropically to remove formic acid. The azeotropic evaporation was repeated three times. The residue obtained upon azeotropic evaporation was washed with diisopropylether (100 mL×3) to give product as white solid TO g (34%). mp: 142.5° C.-144.3° C.

$^1$H NMR (300 MHz, DMSO-d$_6$) δ (ppm): 0.63-0.67 (m, 4H), 0.98-0.10 (m, 4H), 0.14-0.17 (m, 12H), 1.40 (bs, 8H), 11.98 (s, 2H). $^{13}$C NMR (75 MHz, DMSO-d$_6$) δ (ppm): 15.09, 23.29, 27.74, 29.51, 29.74, 33.85 and 176.68. MS: 309 (M−H)

Example 22

Synthesis of 2,13-dicyclopropyll-tetradecanedioic acid monoethyl ester

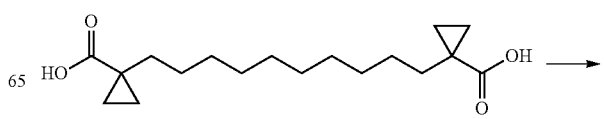

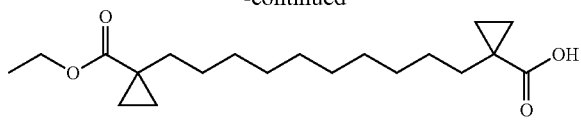

To a suspension of product from Example 21 (7.0 g, 0.02 mol) in ethanol (70 mL) was added thionyl chloride (1.65 mL, 0.02 mol) drop wise at ice temperature. Ice bath was removed and reaction mixture stirred at ambient temperature over a period of 16 h. Filtered the reaction mixture to remove un reacted starting material (2.1 g) and residue obtained upon evaporation of the filtrate was purified by column chromatography (5% ethyl acetate in petroleum ether) to give product as a pale yellow liquid 1.0 g (13.1%).

$^1$H NMR (300 MHz, DMSO-$d_6$) δ (ppm): 0.63-0.72 (m, 4H), 0.98-1.04 (m, 4H), 1.09 (t, J=6.9 Hz, 3H), 1.23 (bs, 12H), 1.40-1.48 (m, 8H), 4.02 (q, J=6.9 Hz, 2H), 11.99 (bs, 1H). MS: 337 (M−H)

Example 23

Synthesis of 1-[10-(1-Carboxymethyl-cyclopropyl)-decyl]-cyclopropanecarboxylic acid

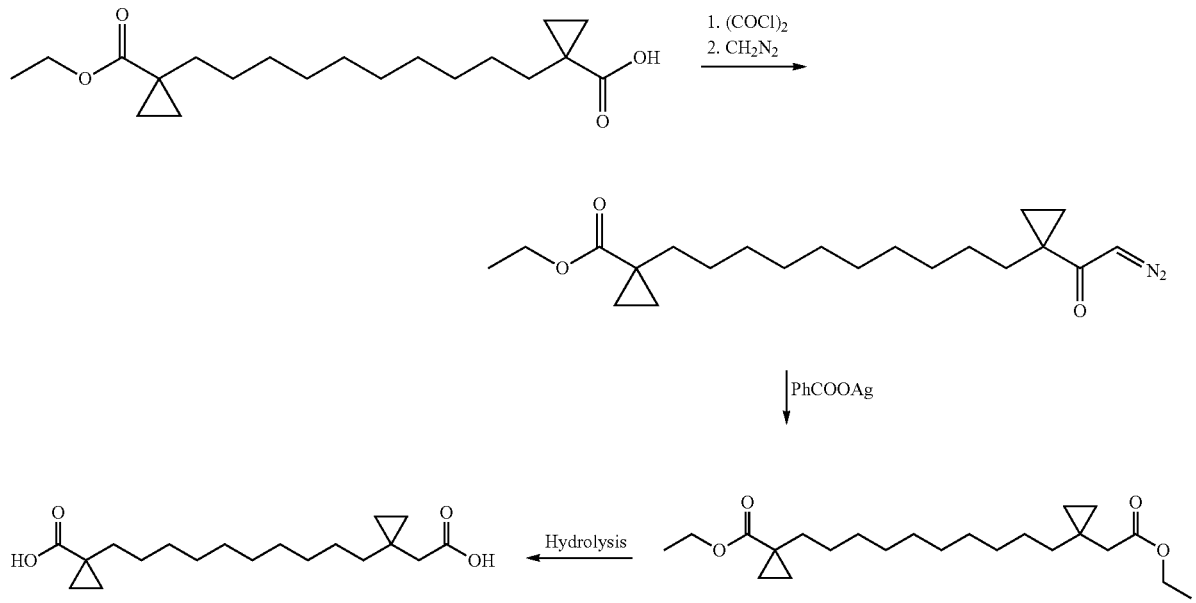

Step 1: To a suspension of acid product of Example 22 (1.0 g, 2.9 mmol) in dichloromethane (15 mL) was added oxalyl chloride (0.37 mL, 4.3 mmol) and catalytic amount of DMF (0.01 mL) at ice temperature. Then ice bath was removed and reaction mixture was stirred at room temperature over a period of 1 h. The crude product obtained upon evaporation of the volatiles was diluted with diethyl ether (5.0 mL), cooled to 0° C. and a solution of diazomethane (1.24 g, 0.03 mol) in ether (100 mL) added. Then the mixture was allowed to reach room temperature and stirred over a period of 16 h. Excess of diazomethane was removed with steam of nitrogen, the crude product obtained upon evaporation of the ether was diluted with ethyl acetate (200 mL), washed with water (100 mL), brine (100 mL), dried over sodium sulphate. The crude product obtained upon evaporation of ethyl acetate was purified by flash column chromatography to give product as a yellow liquid 0.7 g (65%).

$^1$H NMR (300 MHz, DMSO-$d_6$) δ (ppm): 0.69-0.72 (m, 4H), 1.00-1.05 (m, 4H), 1.15 (t, J=7.2 Hz, 3H), 1.23 (bs, 12H), 1.32-1.35 (m, 4H), 1.44-1.51 (m, 4H), 4.02 (q, J=7.2 Hz, 2H), 6.17 (s, 1H). LC-MS: 363.5 (M+H)

Step 2: To a solution of diazo compound of Step 1 (0.7 g, 1.9 mmol) in ethanol (20 mL) was added a freshly prepared solution of silver benzoate (0.35 g, 1.5 mmol) in triethyl amine (3.0 mL) in a drop wise fashion at reflux temperature. Then the reaction mixture was refluxed over a period of 6 h, allowed to cool room temperature and filtered. The crude product obtained upon evaporation of the ether was diluted with ethyl acetate (200 mL), washed with 10% sodium bicarbonate (50 mL), water (50 mL), brine (50 mL) and dried over sodium sulphate. The crude product obtained upon evaporation of ethyl acetate was purified by flash column chromatography (4% ethyl acetate in petroleum ether) to give product 0.35 g (47.9%) as pale yellow oil.

$^1$H NMR (300 MHz, DMSO-$d_6$) δ (ppm): 0.27-0.30 (m, 2H), 0.36-0.39 (m, 2H), 0.69-0.72 (m, 2H), 1.01-1.05 (m, 2H), 1.12-1.20 (m, 6H), 1.23-1.26 (m, 16H), 1.36-1.47 (m, 4H), 2.20 (s, 2H), 3.98-4.08 (m, 4H). MS: 381.7 (M+H)

Step 3: To a solution of KOH (0.86 g, 15.4 mmol) in 90% ethanol (10 mL) was added product of Step 2 (0.35 g, 0.91 mmol) at 80° C. and stirred at same temperature over a period of 8.5 h. The crude product obtained upon evaporation of the solvent was diluted with water (2.0 mL), acidified to pH=2 (1N HCl), and extracted with ethyl acetate (50 mL×2), The organic layer was dried over sodium sulphate and concentrated. The residue obtained was washed with n-hexane (10.0 mL×2) and dried under high vacuum to give product as a white solid 250 mg (83%). mp: 71.9° C.-74.3° C.

$^1$H NMR (300 MHz, DMSO-$d_6$) δ (ppm): 0.26-0.29 (m, 2H), 0.34-0.37 (m, 2H), 0.63-0.66 (m, 2H), 0.99-1.02 (m, 2H), 1.22 (bs, 12H), 1.27 (bs, 4H), 1.40 (bs, 4H), 2.12 (s, 2H), 11.97 (bs, 2H). $^{13}$C NMR (75 MHz, DMSO-d$_6$) δ (ppm): 12.01, 15.10, 17.50, 23.30, 26.53, 27.74, 29.50, 29.55, 29.72, 29.74, 33.85, 36.52, 173.80 and 176.68. MS: 323.5 (M−H)

Example 24

Synthesis of 1-(13-Carboxy-13-methyl-tetradecyl)cyclopropane carboxylic acid

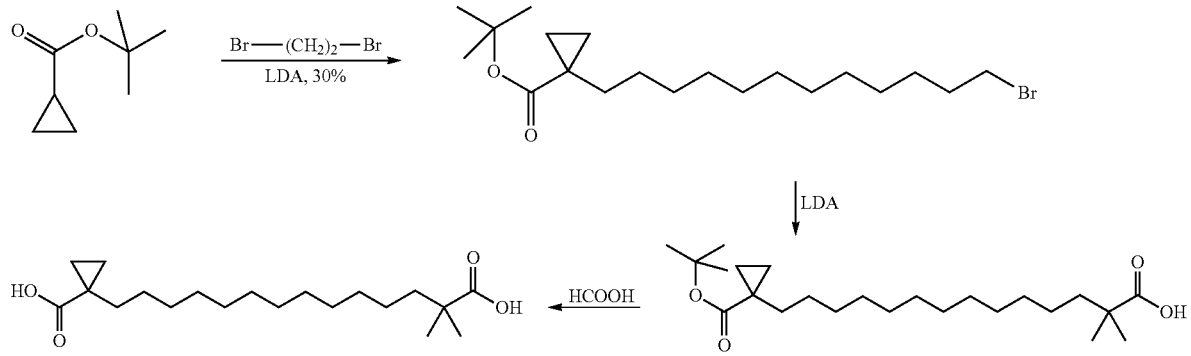

Step 1: A solution of n-butyl lithium in hexane (1.4M, 41.8 mL, 0.06 mol) was added drop wise to a solution of freshly distilled diisopropylamine (9.3 mL, 0.06 mol) in dry THF (200 mL) at −60° C. under nitrogen atmosphere. The reaction mixture was slowly warmed to −20° C. and stirred for 30 min. The reaction mixture was re cooled to −60° C. and cyclopropanecarboxylic acid tert-butyl ester (8.67 g, 0.06 mol) added drop wise over a period 30 min. Reaction mixture was slowly warmed to −20° C. and stirred for 30 min. To the re-cooled (−60° C.) reaction mixture was added drop wise 1,12-dibromododecane (20.0 g, 0.06 mol) in dry THF (20 mL) and DMPU (1.56 g, 0.01 mol). Then the temperature was allowed to reach room temperature and stirred at same temperature over a period of 16 h. The resulting reaction mixture was quenched with saturated NH$_4$Cl (500 mL) at 0° C. and extracted with ethyl acetate (300 mL×3). The organic phases were combined, dried over anhydrous Na$_2$SO$_4$ and volatiles were evaporated under reduced pressure to yield a pale yellow liquid which was filtered through silica gel (230-400) column (0.5% ethyl acetate in petroleum ether) to give 2.5 g (10.6%) product as a yellow color viscous oil.

$^1$H NMR (300 MHz, DMSO-d6) δ (ppm): 0.63-0.66 (m, 2H), 0.94-0.98 (m, 2H), 1.24 (bs, 17H), 1.33-1.39 (m, 12H), 1.73-1.83 (m, 2H), 3.33-3.54 (m, 2H).

Step 2: A solution of n-butyl lithium in hexane (1.4M, 19.42 mL, 0.02 mol) was added drop wise to a solution of freshly distilled diisopropylamine (4.19 mL, 0.02 mol) in dry THF (30 mL) at −60° C. under nitrogen atmosphere. The reaction mixture was slowly warmed to −20° C. and stirred for 30 min. The reaction mixture was re-cooled to −60° C. and isobutyric acid (0.05 mL, 0.01 mol) added drop wise over a period 30 min. Reaction mixture was slowly warmed to −20° C. and stirred for 30 min. To the re-cooled (−60° C.) reaction mixture was added drop wise bromo intermediate of Step 1 (2.0 g, 0.005 mol) in dry THF (5.0 mL). Then the temperature was allowed to reach room temperature and stirred at same temperature over a period of 16 h. The resulting reaction mixture was quenched with saturated NH$_4$Cl (300 mL) at 0° C. and extracted with ethyl acetate (100 mL×3). The organic phases were combined, dried over anhydrous Na$_2$SO$_4$ and volatiles were evaporated under reduced pressure to give pale yellow liquid which was filtered through silica gel (230-400) column (2.0% ethyl acetate in petroleum ether) to give 1.3 g crude (64%) colorless oil. The compound was taken to next step without further purification and characterization.

Step 3: Formic acid (6.5 mL, 5 vol) was added drop wise with vigorous stirring to the compound 4 (1.3 g, 0.003 mol) at 0° C. Then ice bath was removed and reaction mixture stirred at room temperature over a period of 16 h. The resulting reaction mixture was diluted with toluene (10 mL) and evaporated azeotropically to remove formic acid. The azeotropic evaporation was repeated two times. The residue obtained upon azeotropic evaporation was washed with 10% dichloromethane in hexane (20 mL×3) to give product as an off-solid 350 mg (31%). mp: 85.6-86.7° C.

$^1$H NMR (300 MHz, DMSO-d$_6$) δ (ppm): 0.63-0.66 (m, 2H), 0.99-1.02 (m, 2H), 1.06 (s, 6H), 1.23 (bs, 18H), 1.40-1.44 (m, 6H), 12.00 (bs, 2H). $^{13}$C NMR (75 MHz, DMSO-d$_6$) δ (ppm): 15.09, 23.31, 24.94, 25.47, 27.75, 29.50, 29.74, 30.04, 33.86, 41.66, 176.68 and 179.27. MS−339.0 (M−H)

Example 25

Synthesis of {1-[12-(1-Hydroxymethyl-cyclopropyl)-dodecyl]-cyclopropyl}-methanol

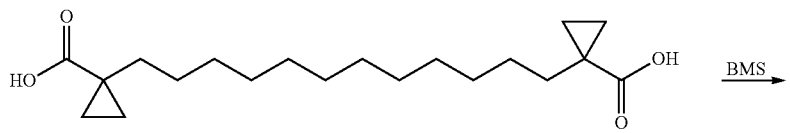

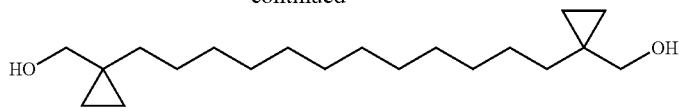

To a solution of product of Example 1 (2.0 g, 5.9 mmol) in dry THF (20 mL, 10 vol) was added boranedimethyl sulfide (5.61 mL, 59.1 mmol) at ice bath temperature. After 10 min ice bath was removed and the reaction mixture was stirred at room temperature for 5 h. The resulting reaction mixture was quenched with saturated ammonium chloride (100 mL) at ice bath temperature and extracted with ethyl acetate (100 mL×3). The combined organic layer was washed with water (100 mL), brine (100 mL) and dried over sodium sulphate. The residue obtained upon evaporation of the volatiles was washed with ratio (0.5:9.5) of dichloromethane: petroleum ether to give product as an off-white solid 1.5 g (81.9%). mp: 63.2-64.6° C.

$^1$H NMR (300 MHz, DMSO-$d_6$) δ (ppm): 0.15-0.18 (m, 4H), 0.27-0.30 (m, 4H), 1.23 (bs, 16H), 1.28 (bs, 8H), 3.19 (d, J=5.7 Hz, 4H), 4.37 (t, J=5.7 Hz, 2H, —OH, Exchangeable proton). $^1$H NMR (300 MHz, DMSO-$d_6$-$D_2$O) δ (ppm): 0.13-0.16 (m, 4H), 0.24-0.28 (m, 4H), 1.20 (bs, 16H), 1.25 (bs, 8H), 3.16 (s, 4H). $^{13}$C NMR (75 MHz, DMSO-$d_6$) δ (ppm): 9.86, 22.16, 26.63, 29.60, 29.68, 30.00, 34.37 and 66.04.

Example 26

Synthesis of 1,16-Dimethoxy-2,15-dicyclopropyl-hexadecane

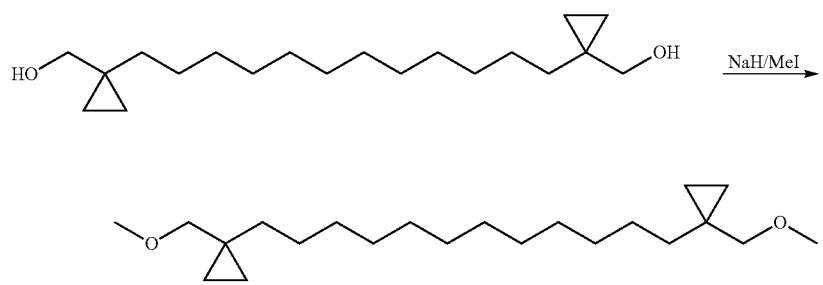

To a solution of product of Example 25 (1.0 g, 3.2 mmol) in dry DMF was added 60% sodium hydride (0.38 g, 9.6 mmol) at ice bath temperature in three portions in intervals of 5 min under nitrogen atmosphere. Methyl iodide (1.19 mL, 19.3 mmol) added drop wise at ice bath temperature. After 10 min ice bath was removed and allowed to stir at room temperature over a period of 2 h. The resulting reaction mixture was quenched with ice water and diluted with ethyl acetate (300 mL). The ethyl acetate layer was washed with water (100 mL×2) and dried over sodium sulphate. The crude product obtained upon evaporation of the solvent was purified by chromatography (3% ethyl acetate in petroleum ether) to give product as pale yellow oil 600 mg (55%).

$^1$H NMR (300 MHz, CDCl3) δ (ppm): 0.31-0.39 (m, 8H), 1.27 (bs, 18H), 1.35 (bs, 8H), 3.19 (s, 4H), 3.35 (s, 6H). $^{13}$C NMR (75 MHz, CDCl3) δ (ppm): 10.05, 19.76, 26.59, 29.67, 29.72, 29.97, 34.39, 58.62 and 78.25.

Example 27

Synthesis of 1,1'-undecane-1,11-diyldicyclopropanecarbonitrile

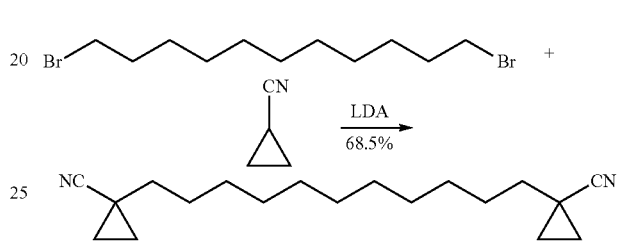

A solution of n-butyl lithium in hexane (1.8M, 297 mL, 0.53 mol) was added drop wise to a solution of freshly distilled diisopropylamine (78.3 mL, 0.50 mol) in dry THF (400 mL) at −60° C. under nitrogen atmosphere. The reaction mixture was slowly warmed to −20° C. and stirred for 30 min. The reaction mixture was re-cooled to −78° C., DMPU (8.16 g, 0.06 mol) was added drop wise and stirred for 15 min. Then cyclopropane carbonitrile (34.17 g, 0.50 mol) was added drop wise over a period 30 min and stirred for 1 h. To the reaction mixture was added drop wise 1,11-dibromoundecane (40.0 g, 0.12 mol) in dry THF (40 mL) and continued stirring at −78° C. for 2 h. The reaction mixture was slowly allowed to reach room temperature and continued stirring over a period of 16 h. The resulting reaction mixture was quenched with saturated NH$_4$Cl (1.0 L) at 0° C. and the reaction mixture was extracted with ethyl acetate (600 mL×2). The organic phases were combined, dried over anhydrous Na$_2$SO$_4$ and volatiles were evaporated under reduced pressure to yield a pale yellow liquid which was purified through silica gel (230-400) column (5% ethyl acetate in petroleum ether) to give product as a pale yellow liquid 25 g (68.5%).

¹H NMR (300 MHz, DMSO-d₆) δ (ppm): 0.84-0.85 (m, 4H), 1.07-1.14 (m, 4H), 1.23-1.25 (bs, 14H), 1.42 (bs, 8H). MS: 287 (M+H), 304 (M+NH₄)

Example 28

Synthesis of 2,14-Dicyclopropyl-pentadecanedioic acid monoethyl ester

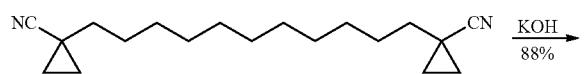

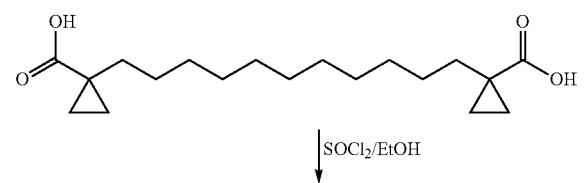

Step 1: To a solution of product of Example 27 (15.0 g, 0.052 mol) in ethanol (150 mL) was added water (75 mL), potassium hydroxide (88 g, 1.57 mol) and the reaction mass was stirred at 140° C. over a period of 72 h. The crude product obtained upon evaporation of the solvent was diluted with water (150.0 mL), acidified to pH=2 (6N HCl) to obtain pale yellow precipitate. The solid obtained upon filtration was washed with diisopropyl ether (50 mL×2) and dried to give product as pale yellow solid 15 g (88.33%); identical to product of Example 17.

¹H NMR (300 MHz, DMSO-d₆) δ (ppm): 0.63-0.70 (m, 4H), 0.92-0.98 (m, 4H), 1.21 (s, 14H), 1.38 (bs, 8H), 11.96 (bs, 2H). MS: 323 (M−H)

Step 2: To a suspension of product of Step 1 (15.0 g, 0.04 mol) in ethanol (150 mL) was added thionyl chloride (3.38 mL, 0.04 mol) drop wise at ice temperature. Ice bath was removed and reaction mixture stirred at 25° C. over a period of 16 h. The crude product obtained upon evaporation of the volatiles was purified through silica gel (230-400) column (5% ethyl acetate in petroleum ether) to give product as an orange liquid 4.0 g (24.5%) and recovered starting material (6.0 g, 40%).

¹H NMR (300 MHz, DMSO-d₆) δ (ppm): 0.63-0.73 (m, 4H), 0.99-1.02 (m, 4H), 1.13 (t, J=6.9 Hz, 3H), 1.22 (bs, 14H), 1.38-1.42 (m, 8H), 4.01 (q, J=6.9 Hz, 2H), 11.98 (bs, 1H, —COOH Exchangeable 1H). MS: 351 (M−H)

Example 29

1-[11-(1-Hydroxymethyl-cyclopropyl)-undecyl]-cyclopropane carboxylic acid ethyl ester

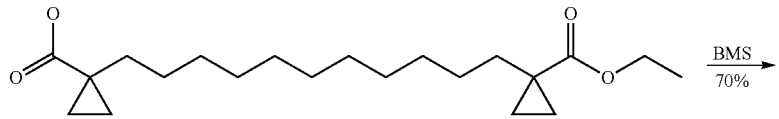

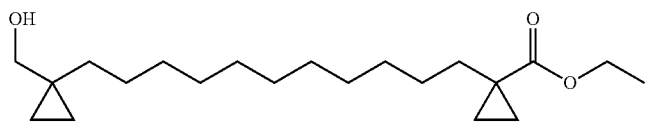

To a solution of product of Example 28 (4.0 g, 1.3 mol) in dry THF (40 mL) was added boranedimethyl sulfide (5.3 mL, 0.056 mol) at ice bath temperature. After 10 min, ice bath was removed and the reaction mixture stirred at room temperature over a period of 5 h. The resulting reaction mixture was quenched with saturated ammonium chloride (100 mL) at ice bath temperature and extracted with ethyl acetate (200 mL×3). The combined organic layer was washed with water (100 mL), brine (100 mL) and dried over sodium sulphate. The residue obtained upon evaporation of the volatiles was purified by silica gel (230-400) column (10% ethyl acetate in petroleum ether) to give product as orange oil 2.7 g (70%).

¹H NMR (300 MHz, DMSO-d₆) δ (ppm): 0.14-0.17 (m, 2H), 0.26-0.29 (m, 2H), 0.68-0.71 (m, 2H), 1.00-1.04 (m, 2H), 1.14 (t, J=7.2 Hz, 3H), 1.22-1.27 (m, 18H), 1.34-1.38 (m, 4H), 3.18 (d, J=5.7 Hz, 2H), 4.01 (q, J=7.2 Hz, 2H), 4.36 (t, J=5.7 Hz, 1H). MS: 321 (M−H₂O).

-continued

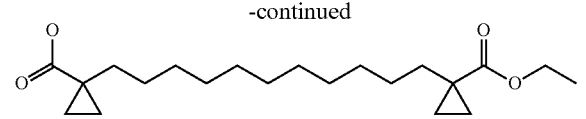

Example 30

Synthesis of 1-[11-(1-Carboxymethyl-cyclopropyl)-undecyl]-cyclopropanecarboxylic acid

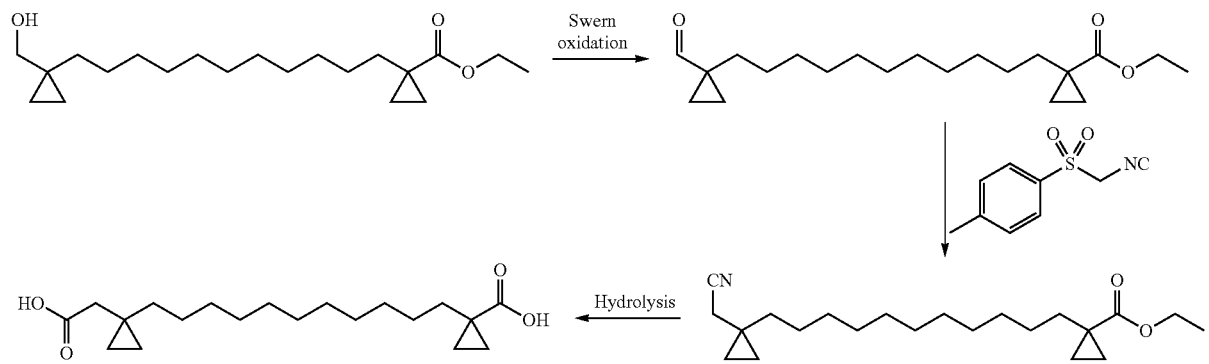

Step 1: A solution of dichloromethane (15 mL) and oxalyl chloride (1.5 mL, 0.017 mol) in a 50 mL flask was cooled in a dry ice-acetone bath (−78° C.). A solution of dimethyl sulfoxide (2.5 mL, 0.035 mol) dissolved in dichloromethane (7 mL) was added to the stirred oxalyl chloride solution at −70° C. The reaction mixture was stirred for 5 minutes, and a solution of product of Example 29 (2.7 g, 7.9 mmol) in dichloromethane (5 mL) was added drop wise over a period of 5 minutes. Stirring was continued for an additional 45 min at −70° C. and triethylamine (7.3 mL, 0.08 mol) was added. The reaction mixture was stirred for 5 min and then allowed to warm to room temperature. After 1 hour, water (200 mL) was added and the aqueous layer was extracted with additional dichloromethane (500 mL). The organic layer was combined, washed with brine (200 mL) and dried over anhydrous sodium sulphate. The crude product obtained upon evaporation of the solvent was purified by silica gel column (2.0% ethyl acetate in petroleum ether) to give product as a yellow liquid 2.2 g (82%).

$^1$H NMR (300 MHz, DMSO-$d_6$) δ (ppm): 0.69-0.71 (m, 2H), 0.92-0.94 (m, 2H), 1.00-1.03 (m, 2H), 1.10-1.12 (m, 2H), 1.13 (t, J=7.2 Hz, 3H), 1.22-1.48 (m, 22H), 4.01 (q, J=7.2 Hz, 2H), 8.56 (s, 1H). MS: 337 (M+H)

Step 2: To a mixture of potassium-t-butoxide (3.0 g, 27.4 mmol) and toluenesulphonylmethyl isocyanide (2.7 g, 13.7 mmol) in 1,2-dimethoxyethane (20 mL) was added a solution of product of Step 1 (2.2 g, 6.5 mmol) in 1,2-dimethoxyethane (5 mL) at −60° C. and continued stirring at same temperature for 10 min. Then reaction mixture was allowed to reach room temperature and continued stirring for 1 h. To the reaction mixture methanol (25 mL) was added and refluxed for 15 min. The residue obtained upon evaporation of volatiles was dissolved in 4% acetic acid (50 mL), extracted with dichloromethane (100 mL×3). The combined organic layers were washed with 10% NaHCO$_3$ (20 mL), dried (Na$_2$SO$_4$) and concentrated to give crude product as orange liquid. The crude product was purified by silica gel column (5.0% ethyl acetate in petroleum ether) to give crude product as yellow liquid 1.6 g (70%) that was used in next reaction without further purification.

Step 3: To a solution of product of Step 2 (1.3 g, 3.7 mmol) in ethanol (12 mL) was added water (6 mL), potassium hydroxide (6.2 g, 112.2 mmol) and the reaction mass was stirred at 140° C. over a period of 16 h. The crude product obtained upon evaporation of the solvent was diluted with water (10 mL), acidified to pH=2 (6N HCl) and extracted with ethyl acetate (100 mL×3). The crude product obtained upon evaporation of the solvent was purified by silica gel column (20% ethyl acetate in petroleum ether) to give product as white solid 0.62 g (49.2%). mp: 75.3° C.-78.9° C.

$^1$H NMR (300 MHz, DMSO-$d_6$) δ (ppm): 0.26-0.34 (m, 4H), 0.63-0.64 (m, 2H), 0.99-1.0 (m, 2H), 1.21-1.26 (m, 18H), 1.39 (m, 4H), 2.11 (s, 2H), 11.95 (bs, 2H exchangeable-COOH). $^{13}$C NMR (75 MHz, DMSO-$d_6$) δ (ppm): 12.00, 15.07, 17.48, 23.28, 26.51, 27.72, 29.50, 29.72, 33.83, 36.51, 173.77 and 176.65. MS: 337 (M−H)

Example 31

Synthesis of 2,15-Dicyclopropyl-hexadecanedioic acid diamide

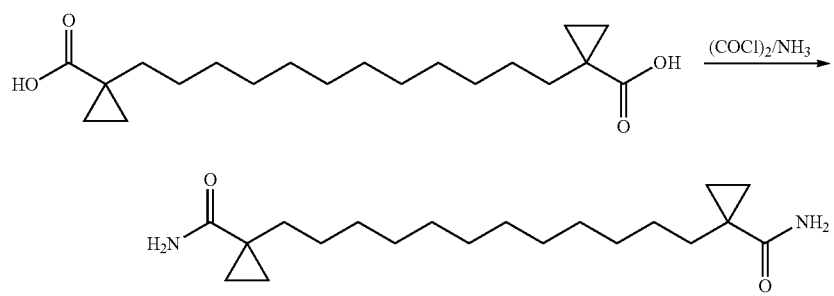 [SMILES: O=C(O)C1(CCCCCCCCCCCCC2(C(=O)O)CC2)CC1 ; NC(=O)C1(CCCCCCCCCCCCC2(C(N)=O)CC2)CC1]

To a solution of product of Example 1 (2.0 g, 5.9 mmol) in dichloromethane (DCM) (20 mL) was added oxalyl chloride (1.98 mL, 23.6 mmol) and catalytic amount of DMF (0.02 mL) at ice temperature. The ice bath was removed and reaction mixture stirred at room temperature over a period of 1 h. The crude product obtained upon evaporation of the solvent was diluted with DCM (10 mL), cooled to ice bath temperature and added ammoniated DCM (100 mL) drop wise fashion. Then reaction mixture was slowly allowed to reach room temperature and stirred for 2 h. The resulting reaction mass was filtered, washed with water (2×50 mL), DCM (2×30 mL) and dried under suction to give product as off-white solid 1.5 g (75%). mp: 157.0-157.9° C.

$^1$H NMR (300 MHz, DMSO-$d_6$) δ (ppm): 0.45-0.48 (m, 4H), 0.86-0.89 (m, 4H), 1.22-1.31 (bs, 20H), 1.43-1.46 (m, 4H), 6.78 (bs, 2H, $D_2O$ exchangeable 1H), 6.96 (bs, 2H, $D_2O$ exchangeable $^1$H). $^{13}$C NMR (75 MHz, DMSO-$d_6$) δ (ppm): 13.77, 24.70, 27.79, 29.52, 29.63, 34.36 and 175.92. MS: 337 (M+H)

Example 32

Synthesis of 1,1'-dodecane-1,12-diyldicyclopropane carbonitrile

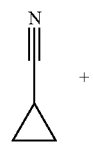

pane carbonitrile (122.7 g, 1.82 mol) added drop wise over a period 1 h and stirred for 1 h. To the reaction mixture was added drop wise 1,12-dibromododecane (150.0 g, 0.45 mol) in dry THF (150 mL) and continued stirring at −78° C. for 2 h. The reaction mixture was slowly allowed to reach room temperature and continued stirring over a period of 16 h. The resulting reaction mixture was quenched with saturated $NH_4Cl$ (3.0 L) at 0° C. and the reaction mixture was extracted with ethyl acetate (1 L×3). The organic phases were combined, dried over anhydrous $Na_2SO_4$ and volatiles were evaporated under reduced pressure to yield a pale yellow liquid which was purified through silica gel (230-400) column (5% ethyl acetate in petroleum ether) to give product as off-white solid. The off-white solid washed with petroleum ether to obtain product as white solid 112 g (81.5%). mp: 45.0° C.-46.9° C.

$^1$H NMR (300 MHz, DMSO-$d_6$) δ (ppm): 0.82-0.85 (m, 4H), 1.11-1.15 (m, 4H), 1.24 (bs, 16H), 1.38-1.42 (m, 8H). $^{13}$C NMR (75 MHz, DMSO-$d_6$) δ (ppm): 9.75, 13.62, 27.81, 28.84, 29.34, 29.41, 29.44, 34.49, and 124.00. MS: 301 (M+H)

Example 33

Preparation of (2,15-dicyclopropyl-hexadecanedioic acid monomethyl ester

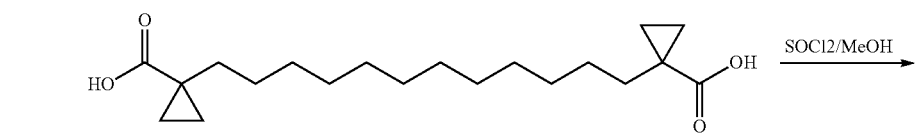

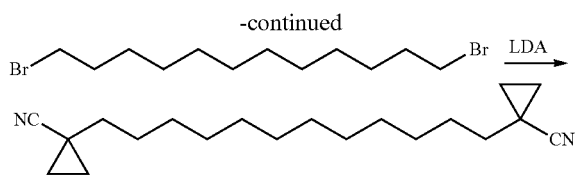

A solution of n-butyl lithium in hexane (1.8M, 1.06 L, 1.92 mol) was added drop wise to a solution of freshly distilled diisopropylamine (280.8 mL, 1.82 mol) in dry THF (1.5 L) at −60° C. under nitrogen atmosphere. The reaction mixture was slowly warmed to −20° C. and stirred for 30 min. The reaction mixture was re-cooled to −78° C., DMPU (29.3 g, 0.22 mol) was added drop wise and stirred for 15 min. Then cyclopro- To a suspension of product of Example 1 (15.0 g, 44.3 mmol) in methanol (150 mL) was added thionyl chloride (3.2 mL, 44.3 mmol) drop wise at ice temperature. Ice bath was removed and reaction mixture stirred at ambient temperature over a period of 48 h. Filtered the reaction mixture to remove unreacted starting material (9 g) and residue obtained upon evaporation of the filtrate was purified by column chromatography (10% ethyl acetate in petroleum ether) to give product as a white solid 1.5 g (9.6%). mp: 59.4° C.-60.5° C.

$^1$H NMR (300 MHz, DMSO-$d_6$) δ (ppm): 0.63-0.72 (m, 4H), 1.00-1.04 (m, 4H), 1.22 (bs, 16H), 1.40-1.46 (m, 8H), 3.55 (s, 3H), 11.98 (s, 1H, —COOH, $D_2O$ exchangeable $^1$H). $^{13}$C NMR (75 MHz, DMSO-$d_6$) δ (ppm): 15.60, 16.45, 23.34, 23.52, 27.55, 27.66, 29.56, 29.62, 29.81, 33.58, 33.97, 51.65, 176.01 and 182.31. MS: 351 (M−H)

Example 34

Preparation of 1-[12-(1-cyclopropylcarbamoyl-cyclopropyl)-dodecyl]-cyclopropane-carboxylic acid methyl ester

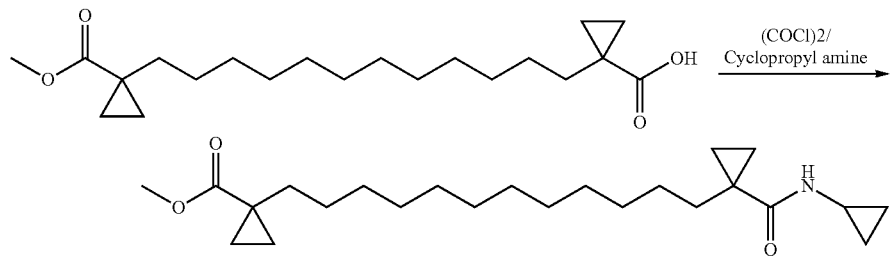

To a solution of product of Example 33 (0.91 g, 2.58 mmol) in dichloromethane (9.1 mL) was added oxalyl chloride (0.4 mL, 5.1 mmol) and catalytic amount of DMF (0.015 mL) at ice temperature. The ice bath was removed and reaction mixture stirred at room temperature over a period of 1 h. The crude product obtained upon evaporation of the solvent was diluted with DCM (10 mL), cooled to ice bath temperature added triethyl amine (1.0 mL, 7.75 mmol), and cyclopropyl amine (1.04 g, 2.5 mmol) added in a drop wise fashion. Then reaction mixture was slowly allowed to reach room temperature and stirred for 16 h. The resulting reaction mass was diluted with ethyl acetate (250 mL), washed with water (50 mL) and dried over sodium sulphate. The residue obtained upon evaporation of the volatiles was purified by silica gel (230-400) column (25% ethyl acetate in petroleum ether) to give product as an off-white solid 0.79 g (79%). mp: 50.6° C.-53.0° C.

$^1$H NMR (300 MHz, DMSO-$d_6$) δ (ppm): 0.37-0.49 (m, 4H), 0.55-0.58 (m, 2H), 0.71-0.72 (m, 2H), 0.84-0.85 (m, 2H), 1.03-1.05 (m, 2H), 1.22 (bs, 20H), 1.36-1.46 (m, 4H), 2.54-2.59 (m, 1H), 3.56 (s, 3H), 7.42 (bs, 1H, —CONH—, $D_2O$ exchangeable $^1$H). $^{13}$C NMR (75 MHz, DMSO-$d_6$) δ (ppm): 6.61, 11.78, 14.00, 15.41, 22.82, 23.47, 24.53, 25.22, 27.26, 27.38, 27.57, 29.43, 29.48, 29.52, 29.73, 33.91, 34.55, 36.08, 51.49, 175.45 and 175.79. MS: 392 (M+H)

Example 35

Preparation of 1-[12-(1-Cyclopropylcarbamoyl-cyclopropyl)-dodecyl]-cyclopropane carboxylic acid

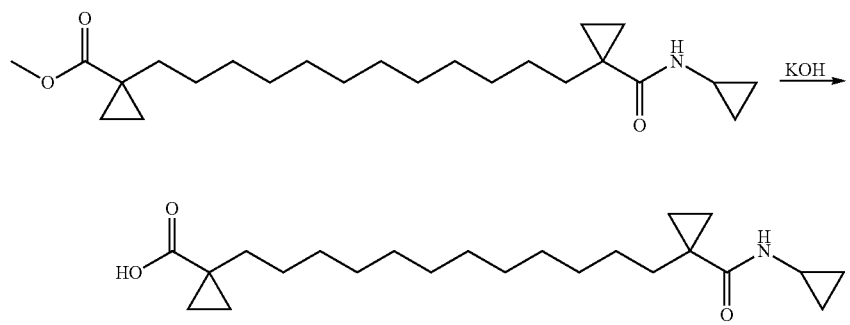

To a solution of product of Example 34 (0.7 g, 1.9 mmol) in methanol (7 mL) was added KOH (0.36 g, 6.4 mmol) in water (2.1 mL) and the reaction mixture was stirred at 60° C. over a period of 16 h. The crude product obtained upon evaporation of the solvent was diluted with water (5.0 mL), acidified to pH=2 (1.5N HCl), extracted with ethyl acetate (100 mL×2). The organic layer was dried over sodium sulphate and concentrated. The residue obtained upon evaporation of the volatiles was purified by silica gel (230-400) column (50% ethyl acetate in petroleum ether) to give product as white solid 0.51 g (76%). mp: 95.3° C.-97.7° C.

$^1$H NMR (300 MHz, DMSO-$d_6$) δ (ppm): 0.37-0.45 (m, 4H), 0.52-0.57 (m, 2H), 0.63-0.66 (m, 2H), 0.83-0.86 (m, 2H), 0.98-1.01 (m, 2H), 1.22 (bs, 18H), 1.40-1.46 (m, 6H), 2.51-2.59 (m, 1H), 7.42 (s, 1H, —CONH—, $D_2O$ exchangeable 1H), 11.99 (s, 1H, —COOH, $D_2O$ exchangeable $^1$H). $^{13}$C NMR (75 MHz, DMSO-$d_6$) δ (ppm): 6.68, 14.10, 16.21, 22.92, 23.29, 24.54, 27.37, 27.49, 29.42, 29.48, 29.51, 29.70, 29.75, 33.60, 34.56, 175.76 and 181.51. MS: 376 (M−H)

Example 36

Preparation of 1-[12-(1-Methanesulfonylaminocarbonyl-cyclopropyl)-dodecyl]-cyclopropanecarboxylic acid methyl ester

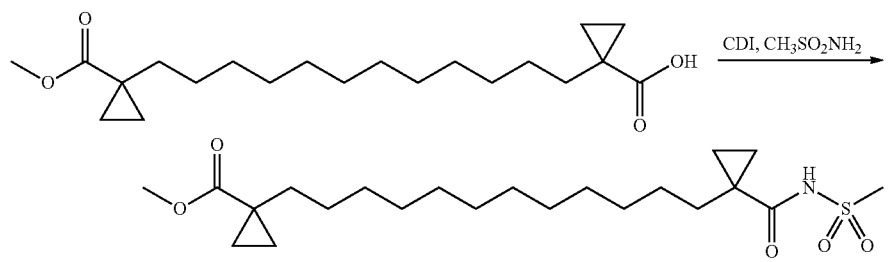

To a solution of product of Example 33 (1.6 g, 4.5 mmol) in THF (16 mL, 10V) was added CDI (1.84 g, 8.1 mmol) and DMAP (0.06 g, 0.4 mmol) at room temperature. The reaction mixture stirred at room temperature over a period of 16 h. To the resultant reaction mixture was added DBU (227 g, 14.9 mmol), methane sulfonamide (1.08 g, 11.3 mmol) and the resulting reaction mixture was refluxed at 100° C. over a period of 5 h. The reaction mixture was quenched with saturated NH$_4$Cl (20 mL), diluted with ethyl acetate (200 mL), separated organic layer, washed with water (50 mL), brine (50 mL), dried over sodium sulphate and evaporated under reduced pressure. The residue obtained upon evaporation of the volatiles was purified by silica gel (230-400) column (25% ethyl acetate in petroleum ether) to give product as white solid 1.2 g (63%). mp: 53.5° C.-54.5° C.

$^1$H NMR (300 MHz, DMSO-d$_6$) δ (ppm): 0.63-0.73 (m, 4H), 1.02-1.08 (m, 4H), 1.23 (bs, 20H), 1.31-1.52 (m, 4H), 3.20 (s, 3H), 3.57 (s, 3H), 11.17 (s, 1H, —CONH—, D$_2$O exchangeable $^1$H). $^{13}$C NMR (75 MHz, DMSO-d$_6$) δ (ppm): 15.44, 15.62, 23.49, 25.78, 27.41, 27.56, 29.39, 29.52, 29.72, 33.52, 33.89, 41.45, 51.54, 173.74 and 175.88. MS: 428.0 (M−H)

Example 37

1-[12-(1-Methanesulfonylaminocarbonyl-cyclopropyl)-dodecyl]-cyclopropanecarboxylic acid To a solution product of Example 36 (0.85 g, 1.97 mmol) in methanol (8.5 mL) was added KOH (0.39 g, 7.1 mmol) in water (2.1 mL) and the reaction mixture was stirred at 60° C. over a period of 16 h. The crude product obtained upon evaporation of the solvent was diluted with water (5.0 mL), acidified to pH=2 (1.5N HCl), extracted with ethyl acetate (100 mL×2). The organic layer was dried over sodium sulphate and concentrated. The residue obtained upon evaporation of the volatiles was purified by silica gel (230-400) column (25% ethyl acetate in petroleum ether) to give product as white solid 0.55 g (67%). mp: 97.5° C.-99.4° C.

$^1$H NMR (300 MHz, DMSO-d$_6$) δ (ppm): 0.61-0.62 (m, 4H), 0.95-0.96 (m, 4H), 1.02 (bs, 18H), 1.18-1.35 (m, 4H), 1.48 (m, 2H), 3.30 (s, 3H), 11.12 (s, 1H, —CONH—, D$_2$O exchangeable $^1$H), 11.95 (s, 1H, —COOH—, D$_2$O exchangeable $^1$H). $^{13}$C NMR (75 MHz, DMSO-d$_6$) δ (ppm): 15.75, 16.33, 23.28, 25.77, 27.44, 29.48, 29.73, 33.51, 41.53, 173.78 and 181.77. MS: 414 (M−H)

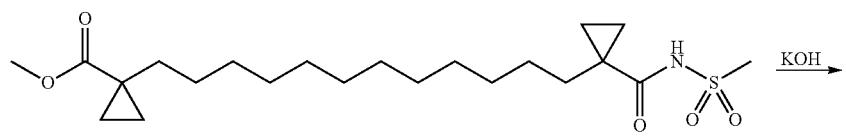

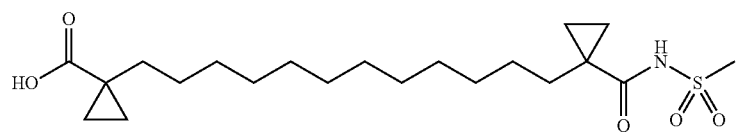

Example 38

Preparation of 1-[12-(1-Difluoromethyl-cyclopropyl)-dodecyl]-cyclopropanecarboxylic acid ethyl ester

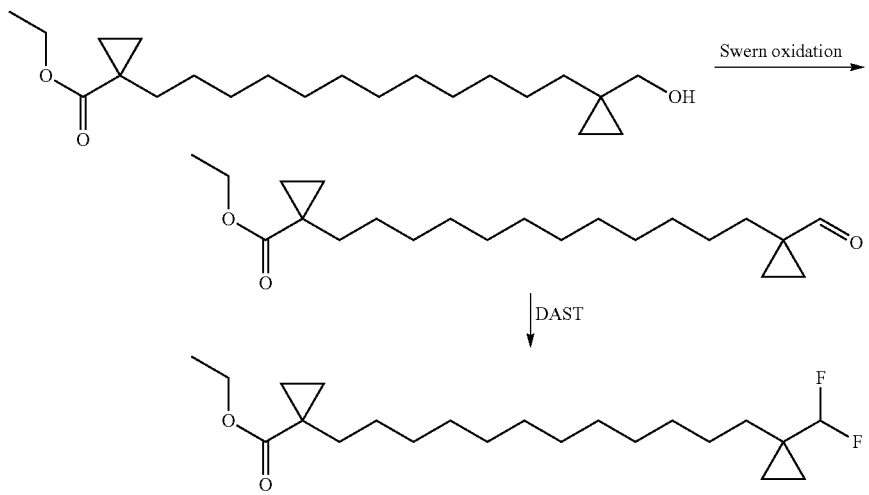

Step 1: A solution of dichloromethane (3 mL) and oxalyl chloride (0.36 mL, 4.3 mmol) in a 50 mL flask was cooled in a dry ice-acetone bath (−78° C.). A solution of dimethyl sulfoxide (0.62 mL, 8.9 mmol) dissolved in dichloromethane (2 mL) was added to the stirred oxalyl chloride solution at −70° C. The reaction mixture was stirred for 5 minutes, and a solution of product of Step 1, Example 13 (0.7 g, 1.9 mmol) in dichloromethane (2 mL) was added drop wise over a period of 5 minutes. Stirring was continued for an additional 45 min at −70° C. and triethylamine (2.7 mL, 19.8 mol) was added. The reaction mixture was stirred for 5 min and then allowed to warm to room temperature. After 1 hour, water (100 mL) was added and the aqueous layer was extracted with additional dichloromethane (200 mL). The organic layer was combined, washed with brine (200 mL) and dried over anhydrous sodium sulphate. The crude product obtained upon evaporation of the solvent was purified by silica gel column (2.0% ethyl acetate in petroleum ether) to give product as a yellow liquid 0.6 g (87%). The aldehyde seems unstable on storage and was used in next step quickly.

Step 2: To a solution of product of Step 1 (0.6 g, 1.71 mmol) in dry THF (6.0 mL) was added diethylamino-sulfur trifluoride (1.31 mL, 8.5 mmol) drop wise at room temperature and the reaction mixture was stirred at same temperature over a period of 16 h. The resulting reaction mass was cooled to ice both temperature and quenched with water (20 mL) and extracted with ethyl acetate (200 mL). the organic layer was washed with 5% sodium bicarbonate (100 mL), brine (100 mL) and dried over sodium sulphate. The crude product obtained upon evaporation of the solvent was purified by silica gel column (2.0% ethyl acetate in petroleum ether) to give product as a yellow oil 0.5 g (79%).

$^1$H NMR (300 MHz, DMSO-d$_6$) δ (ppm): 0.48-0.49 (m, 2H), 0.62-0.64 (m, 2H), 0.68-0.71 (m, 2H), 1.01-1.04 (m, 2H), 1.50 (t, J=7.2 Hz, 3H), 1.23 (bs, 16H), 1-35-1.48 (bs, 8H), 4.02 (q, J=7.2 Hz, 3H), 5.66 (t, J=56.7 Hz, 1H).

Example 39

Synthesis of 1-[12-(1-Difluoromethyl-cyclopropyl)-dodecyl]-cyclopropanecarboxylic acid

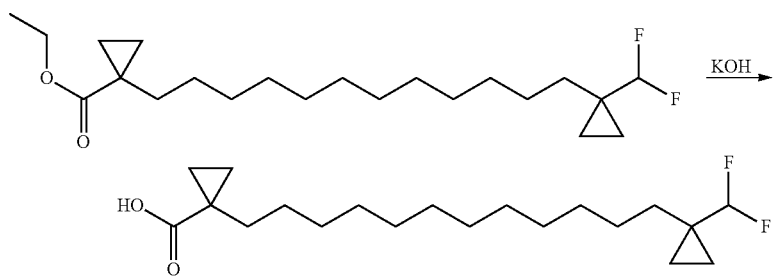

$^1$H NMR (300 MHz, DMSO-d$_6$) δ (ppm): 0.68-0.71 (m, 2H), 0.94-0.99 (m, 2H), 1.01-1.04 (m, 2H), 1.11-1.13 (m, 2H), 1.14-1.17 (m, 3H), 1.23 (bs, 18H), 1.31-1.46 (m, 6H), 4.02 (q, J=7.2 Hz, 3H), 8.56 (s, 1H).

To a solution of potassium hydroxide (0.63 g, 11.2 mol) in 90% ethanol (5 mL) was added product of Example 38 (0.5 g, 1.3 mmol) at 40° C. and the reaction mass was stirred at 40° C. over a period of 16 h. The crude product obtained upon evaporation of the solvent was diluted with water (5 mL), acidified to pH=2 (1N HCl) and extracted with ethyl acetate (100 mL×3). The crude product obtained upon evaporation of the solvent was purified by silica gel column (5% ethyl acetate in petroleum ether) to give product as white solid 0.32 g (69.5%). mp: 54.0° C.-54.8° C.

$^1$H NMR (300 MHz, DMSO-$d_6$) δ (ppm): 0.48-0.49 (m, 2H), 0.64-0.65 (m, 4H), 1.00-1.02 (m, 2H), 1.23 (bs, 16H), 1.40 (bs, 8H), 5.67 (t, J=56.7 Hz, 1H), 11.97 (bs, 2H exchangeable-COOH). $^{13}$C NMR (75 MHz, DMSO-$d_6$) δ (ppm): 7.88, 7.94, 8.00, 15.01, 21.89, 22, 20, 22.52, 23.29, 26.62, 27.69, 29.36, 29.45, 29.70, 29.82, 30.99, 33.83, 116.87, 116.90, 120.03, 120.06, 123.18, 123.21, and 176.58. MS: 343 (M−H)

Example 40

Preparation of 1,1'-dodecane-1,12-diylbis[N-(2-hydroxyethyl)cyclopropanecarboxamide]

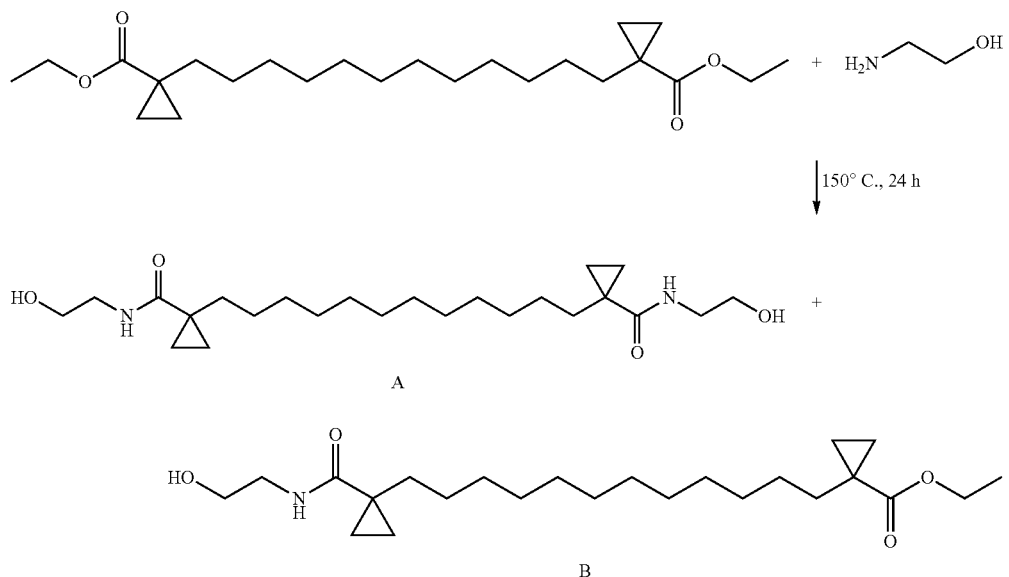

To the product of Example 10 (2.0 g, 5.0 mmol) in a round bottomed flask, ethanolamine (10 mL) was added at room temperature. The reaction mixture was heated at 150° C. over a period of 18 h. The resulting reaction mixture was diluted with ethyl acetate (100 mL), washed with water (2×50 mL) and dried over sodium sulphate. The crude product obtained upon evaporation of the volatiles was purified through silica gel (230-400) column (50% ethyl acetate in petroleum ether) to obtain pure compound A as white solid (0.5 g, 23%) and pure compound B as pale yellow solid (0.75 g, 36%). Compound A: mp: 112.5° C.-113.5° C. 1H NMR (300 MHz, DMSO-d6) δ (ppm): 0.46-0.48 (m, 4H), 0.86-0.89 (m, 4H), 1.22-1.28 (bs, 20H), 1.45-1.48 (m, 4H), 3.07-3.13 (m, 4H), 3.32-3.38 (m, 4H), 4.60 (t, J=5.7 Hz, 2H exchangeable-OH), 7.37 (t, J=5.7 Hz, 2H). $^{13}$C NMR (75 MHz, DMSO-d6) δ (ppm): 13.51, 24.98, 27.62, 29.48, 29.60, 34.23, 42.35, 60.46 and 173.63. MS: 425 (M+H)

Example 41

Preparation of 1-{1-[1-(2-Hydroxy-ethylcarbamoyl)-cyclopropyl]-dodecyl}-cyclopropane carboxylic acid ethyl ester

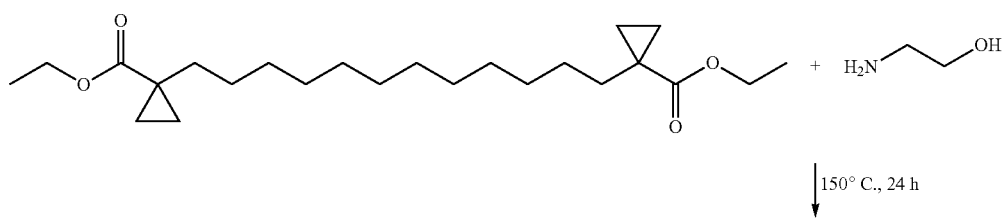

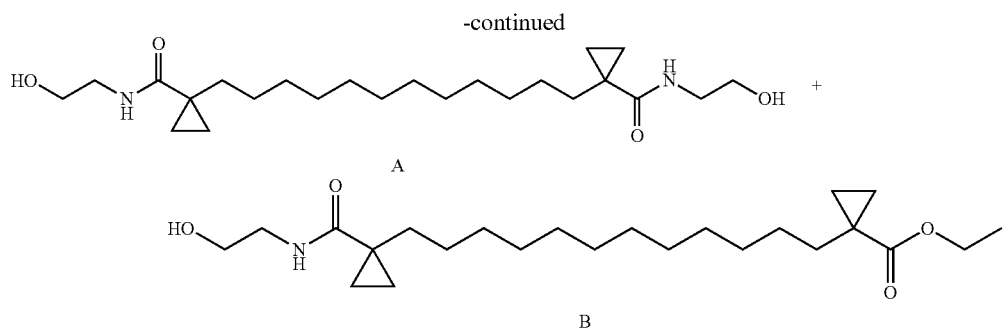

The target compound (B) was prepared as described in Example 40.

mp: 42.2° C.-44.3° C. $^1$H NMR (300 MHz, CDCl$_3$) δ (ppm): 0.60-0.63 (m, 2H), 0.65-0.68 (m, 2H), 1.19-1.94 (m, 4H), 1.21-1.24 (m, 3H), 1.27 (bs, 16H), 1.43-1.57 (m, 8H), 2.06 (bs, 1H, exchangeable-OH), 3.43-3.48 (m, 2H), 3.72-3.76 (m, 2H), 4.11 (q, J=7.2 Hz, 2H), 6.21 (bs, 2H). $^{13}$C NMR (75 MHz, CDCl3) δ (ppm): 14.15, 14.30, 15.36, 23.53, 24.61, 27.43, 27.57, 29.48, 29.54, 29.73, 29.78, 33.90, 34.47, 42.73, 60.21, 62.44, 175.44 and 173.63. MS: 410 (M+H)

Example 42

Synthesis of 1-{12-[1-(2-hydroxy-ethylcarbamoyl)-cyclopropyl]-dodecyl}-cyclopropane carboxylic acid

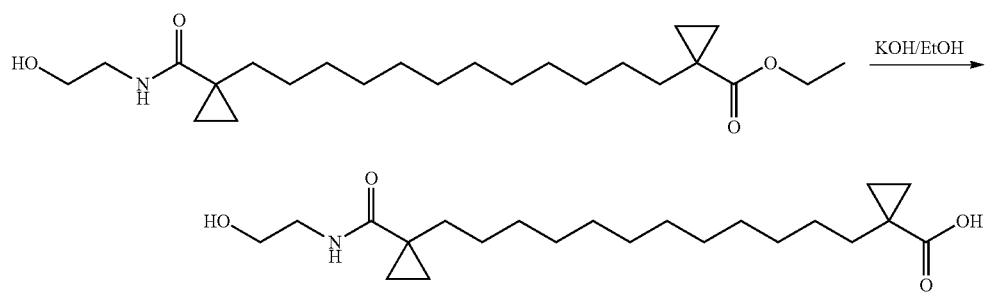 [SMILES: CCOC(=O)C1(CCCCCCCCCCCCC2(C(=O)NCCO)CC2)CC1 ; O=C(O)C1(CCCCCCCCCCCCC2(C(=O)NCCO)CC2)CC1]

To a solution of potassium hydroxide (0.63 g, 11.2 mol) in 90% ethanol (5 mL) was added product B of Example 40 (0.5 g, 1.3 mmol) at 40° C. and the reaction mass was stirred at 40° C. over a period of 2 h. The crude product obtained upon evaporation of the solvent was diluted with water (10 mL), acidified to pH=2 (1.5 N HCl). The white precipitate obtained upon acidification was filtered, washed with petroleum ether to obtain the product as white solid (300 mg, 65.2%). mp: 81.1° C.-83.8° C.

$^1$H NMR (300 MHz, DMSO-d$_6$) δ (ppm): 0.46 (bs, 2H), 0.64-0.65 (m, 2H), 0.86-0.87 (m, 2H), 0.99-1.00 (m, 2H), 1.22 (bs, 18H), 1.40-1.48 (m, 8H), 3.07-3.13 (m, 2H), 3.33-3.36 (m, 2H), 4.61 (t, J=5.1 Hz, 1H exchangeable-OH), 7.39 (bs, 1H, exchangeable-CONH), 11.99 (s, 1H, exchangeable-COOH). $^{13}$C NMR (75 MHz, DMSO-d$_6$) δ (ppm): 13.52, 15.02, 23.30, 24.97, 27.62, 27.69, 29.47, 29.60, 29.69, 33.82, 34.22, 42.34, 60.45, 173.62 and 176.58. MS: 382 (M+H)

Example 43

AMPK activation assay—The assay protocol used for screening compounds is described below:

Reagents:
PathScan Phospho-AMPK (Thr172) Sandwich ELISA Antibody Pair (Cell Signaling Cat. No. 7955)
DuoSet IC Human/Mouse/Rat Total AMPK1 (R&D Systems, Cat. #DYC3197-5)
Lysis Buffer (Cell Signaling Technology, Cat. No. 9803) diluted to 1× in distilled water containing 1 mM PMSF.
3,3',5,5'-Tetramethylbenzidine (TMB) Substrate (Sigma Cat No. T8665)

Day 1: HepG2 cells were seeded at a density of 50,000 cells per well in a 24-well plate in DMEM Low glucose (5 mM) (Sigma) containing 10% FCS (Invitrogen) with 1 nM insulin and incubated for 6 hours at 37° C. After 6 hrs of incubation, the cells were rinsed with starvation media (DMEM Low Glucose without FCS) and 0.5 mL of starvation media was added and incubated overnight at 37° C.

Day 2: Stock concentrations of the compounds (along with standard) were prepared in 100% DMSO and were diluted to the desired concentrations in serum-free DMEM Low glucose media. The medium was aspirated from the wells and 0.5 mL of the medium containing the compounds were added to the appropriate wells and the plate was incubated for 6 hours at 37° C. The media was aspirated and the cells were rinsed twice with cold PBS. 250 μL of 1× lysis buffer was added to all the wells and incubated for 15 minutes on ice. The samples were centrifuged at 2000 g for 5 minutes and the supernatant was collected. Protein concentration in the lysate was quantified by using the BCA assay (Pierce Biotech).

Protocol for Phospho-AMPK ELISA
Coating Procedure:
Day 1: The capture antibody was diluted and coated on a 96-well plate (100 μL per well). The plate was sealed and incubated overnight at 4° C.

Day 2: Each well was aspirated and washed 4× with wash buffer. The plates were then blocked by adding 150 μL of Block buffer to each well. The plate was then incubated at 37° C. for 2 hours. Each plate was washed 4 times with wash buffer and 100 μL of the lysate was transferred to an ELISA plate, covered, and incubated at 37° C. for 2 hours. The contents were discarded and the plate was washed 4 times with wash buffer. After each wash, the residual solution was removed by striking the plate on fresh towels. 100 μL of the detection antibody was then added to each well and the plate was incubated for 1 hour at 37° C. The plate was then washed with wash buffer as earlier and 100 μL of horse radish peroxidase-linked secondary antibody was added to each well and the plate was then incubated for 30 minutes at 37° C. The wash procedure was repeated and 100 μL of substrate solution was added to all the wells and incubated for a further 10 minutes at 37° C. 100 μL of Stop solution was added and the absorbance was read at 450 nm in a micro plate reader.

Protocol for Total AMPK ELISA

Coating Procedure:

Day 1: The capture antibody was diluted to a working concentration of 4 μg/mL in PBS. A 96-well microplate (Maxisorp) was coated with 100 μL per well of the diluted Capture antibody. The plate was sealed and incubated overnight at 4° C.

Day 2: Each well was aspirated and washed 3 times with wash buffer. The plates were then blocked by adding 300 μL of Block buffer to each well. The plate was then incubated at room temperature for 2 hours. Each plate was washed 3 times with wash buffer and 100 μL of the lysate was transferred to the ELISA plate, covered, and incubated at room temperature for 2 hours. The contents were discarded and the plate was washed 3 times with wash buffer. After each wash, the residual solution was removed by striking the plate on fresh towels. 100 μL of the detection antibody was then added to each well and the plate was incubated for 2 hours at room temperature. The plate was then washed with wash buffer as earlier and 100 μL of horse radish peroxidase-linked secondary antibody was added to each well and the plate was incubated for 20 minutes at room temperature. The wash procedure was repeated and 100 μL of substrate solution was added to all the wells and incubated for a further 20 minutes at room temperature. 50 μL of Stop solution was added and the absorbance was read at 450 nm in a microplate reader.

Data Analysis—Data analysis was performed and was expressed in Relative absorbance per mg protein and the ratio of phosphorylated AMPK to total AMPK levels was calculated.

Compounds that showed an increase of ≥40% at <60 μm concentration in AMPK activation assay and/or showed a reduction in triglycerides as a consequence of inhibition of fatty acid synthesis are considered active.

In vivo Efficacy: The in vivo efficacy of compounds of general Formula I can be evaluated in diabetes and dyslipidemia using animals models known in literature. Db/db mouse model is the most commonly used diabetic dyslipidemia model. These animals have high plasma glucose, insulin and triglycerides and exhibit severe insulin resistance (ref—Young A A, Gedulin B R, Bhaysar S, Bodkin N, Jodka C, Hansen B, Denaro M. Diabetes. 1999 May; 48(5):1026-34; Yasuda N, Inoue T, Nagakura T, Yamazaki K, Kira K, Saeki T, Tanaka I. J Pharmacol Exp Ther. 2004 August; 310 (2): 614-9.

Example 44

In Vivo Efficacy of Representative Compounds in Diabetic Mice

The model described below can be used to evaluate potential of representative compounds of generic Formula I to treat diabetes and dyslipidemia.

Male obese diabetic C57BLKS db/db mice (6 weeks old) were procured from the Jackson Laboratory (Bar Harbor, Me.) and were maintained on LabDiet 5K52 ad libitum with access to water. Animals were kept in a temperature-controlled room on a 12:12-h light-dark cycle. Experiments were performed on 6-9 week old mice.

Blood samples were collected after a 6 h fast on day 0 (baseline) and at the end week 1 and week 2 (day 7 and day 14) for analysis of glucose, triglycerides, total cholesterol, insulin and free fatty acid levels. Body weight and feed intake was measured twice weekly. Before initiation of the treatment, the animals were randomized based on plasma glucose levels into treatment groups (n=8 per group). The animals were administered the test compounds in 0.5% carboxymethylcellulose in water at the mentioned doses for two weeks by oral gavage. The control animals received the vehicle (0.5% carboxymethylcellulose in water) alone. Compound administration was continued till day 16.

Measurement of Plasma Parameters

Plasma glucose (PG) and triglycerides (TG) were measured spectrophotometrically in a microplate reader using reagent kits (Labkit, Merck) according to the manufacturer's instructions. Plasma insulin was measured by ELISA using a Rat/Mouse kit from Millipore (Cat. No. EZRMI-13K).

Data Analysis

The percentage reduction was calculated according to the following formula $$1 - \frac{\text{Final day treated value/Day 0 treated value}}{\text{Final day control value/Day 0 Control value}} \times 100$$

Statistical analysis was carried out by one way ANOVA followed by Dunnett's test using GraphPad Prism.

Determination of Homeostatic model assessment of insulin resistance (HOMA)—The HOMA index for insulin resistance was calculated using the formula—

$$I0 \times G0/405$$

Where I0 is the fasting insulin (μU/ml), G0 is the fasting glucose in mg/dL. A factor of 6.945 was used for the conversion of insulin pmol/L to μIU/L).

The table below summarizes the effect on plasma glucose, triglycerides, and insulin resistance after 1-2 weeks of treatment with representative compounds of Formula I. Example numbers denote the products of examples given above. The data presented in the table is representative and should not be read as limiting the invention to the specific examples listed in the Table.

| Example | Dose (mg/kg) | Plasma glucose (% change compared to vehicle) | Plasma Triglycerides (% change compared to vehicle) | Insulin resistance HOMA index (% change compared to vehicle) |
|---|---|---|---|---|
| 4 | 50 | | −51 | −54 |
| 1 | 10 | −52 | | −65 |
| 12 | 20 | −55 | −28 | −89 |
| 15 | 15 | −56 | −35 | −92 |
| 10 | 15 | −51 | −23 | |
| 35 | 15 | −30 | | |
| 37 | 15 | −59 | | |

Although exemplary embodiments of the invention have been described using specific terms, devices, and methods, such description is for illustrative purposes only. The words used are words of description rather than of limitation. It is to be understood that changes and variations may be made by those of ordinary skill in the art without departing from the spirit or scope of the present invention, which is set forth in the following claims. In addition, it should be understood that aspects of the various embodiments may be exchanged in whole or in part.

We claim:
1. A composition comprising at least one compound according to Formula I:

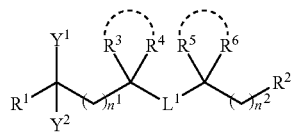

Formula I its stereoisomers and/or pharmaceutically acceptable salts, wherein:
  $R^1$ is selected from a group consisting of hydroxy, alkoxy, amine, alkyl, haloalkyl, $NHSO_2R$, or NHCOR wherein R is selected from alkyl or cycloalkyl, NHR' wherein R' is alkyl or cycloalkyl optionally substituted by hydroxy or alkoxy;
  $n^1$ and $n^2$ are independently selected from 0, 1, and 2;
  at least one of $R^3$ and $R^4$ and/or $R^5$ and $R^6$ form a cyclic ring of 3-8 carbon atoms optionally containing alkyl groups, hetero atoms, or functional groups such as O, N, $SO_2$;
  $R^3$ and $R^4$ or $R^5$ and $R^6$, when they do not form a cyclic ring, are independently selected from hydrogen, alkyl, branched alkyl, and cycloalkyl;
  $L_1$ is a linear aliphatic chain optionally containing from 4 to 16 carbon atoms, optionally substituted one or more times by alkyl, branched alkyl, cycloalkyl, or aryl;
  $R^2$ is independently selected from hydrogen, alkoxy, hydroxy, alkyl, haloalkyl, cycloalkyl, heterocycloalkyl, heteroaryl, cyano, or $COR^7$, wherein $R^7$ is selected from hydroxy, alkyl, alkoxy, or amine, NHR', $NHSO_2R$, or NHCOR;
  $Y^1$ is oxygen or hydrogen;
  $Y^2$ is optional, and wherein when $Y^2$ is present, $Y^1$ and $Y^2$ are hydrogen and when $Y^2$ is not present, $Y^1$ forms a carbonyl group.

2. A composition according to claim 1, wherein the compound is according to Formula II:

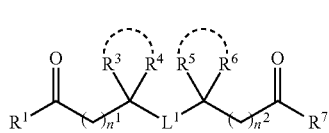

Formula II its stereoisomers and/or pharmaceutically acceptable, wherein:
  $R^1$ and $R^7$ are independently selected from a group consisting of hydroxy, alkoxy, alkyl, amine, NHR' wherein R' is alkyl or cycloalkyl optionally substituted by hydroxy or alkoxy, $NHSO_2R$ or NHCOR, wherein R is selected from alkyl or cycloalkyl;
  $n^1$ and $n^2$ are independently selected from 0, 1, and 2;
  at least one of $R^3$ and $R^4$ and/or $R^5$ and $R^6$ form a cyclic ring of 3-8 carbon atoms optionally containing alkyl groups, hetero atoms, or functional groups such as O, N, $SO_2$;
  $R^3$ and $R^4$ or $R^5$ and $R^6$, when they do not form a cyclic ring, are independently selected from hydrogen, alkyl, branched alkyl, and cycloalkyl;
  $L^1$ is independently a linear aliphatic chain optionally containing from 6 to 16 carbon-atoms and $L^1$ may optionally be substituted one or more times by alkyl, branched alkyl, cycloalkyl, or aryl.

3. A composition according to claim 1, wherein the compound is according to Formula III:

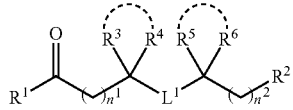

Formula III its stereoisomers and/or pharmaceutically acceptable salts for the treatment of diabetes and diabetes-associated dyslipidemia, wherein:
  $R^1$ is selected from a group consisting of hydroxy, alkoxy, amine, alkyl, haloalkyl, NHR' wherein R' is alkyl or cycloalkyl optionally substituted by hydroxy or alkoxy, $NHSO_2R$ or NHCOR, wherein R is selected from alkyl or cycloalkyl;
  $n^1$ and $n^2$ are independently selected from 0, 1, and 2;
  at least one of $R^3$ and $R^4$ and/or $R^5$ and $R^6$ form a cyclic ring of 3-8 carbon atoms optionally containing alkyl groups, hetero atoms, or functional groups such as O, N, $SO_2$;
  $R^3$ and $R^4$ or $R^5$ and $R^6$, when they do not form a cyclic ring, are independently selected from hydrogen, alkyl, branched alkyl, and cycloalkyl; and
  $L^1$ is a linear aliphatic chain optionally containing from 4 to 16 carbon-atoms and $L^1$ may optionally be substituted one or more times by alkyl, branched alkyl, cycloalkyl, or aryl. $R^2$ is independently selected from hydrogen, alkoxy, hydroxy, alkyl, haloalkyl, cycloalkyl, heterocycloalkyl, heteroaryl, cyano or $COR^7$; wherein $R^7$ is selected from a group consisting of hydroxy, alkyl, alkoxy, amine, NHR', or $NHSO_2R$.

4. The composition according to claim 1, wherein the compound is selected from one or more of:
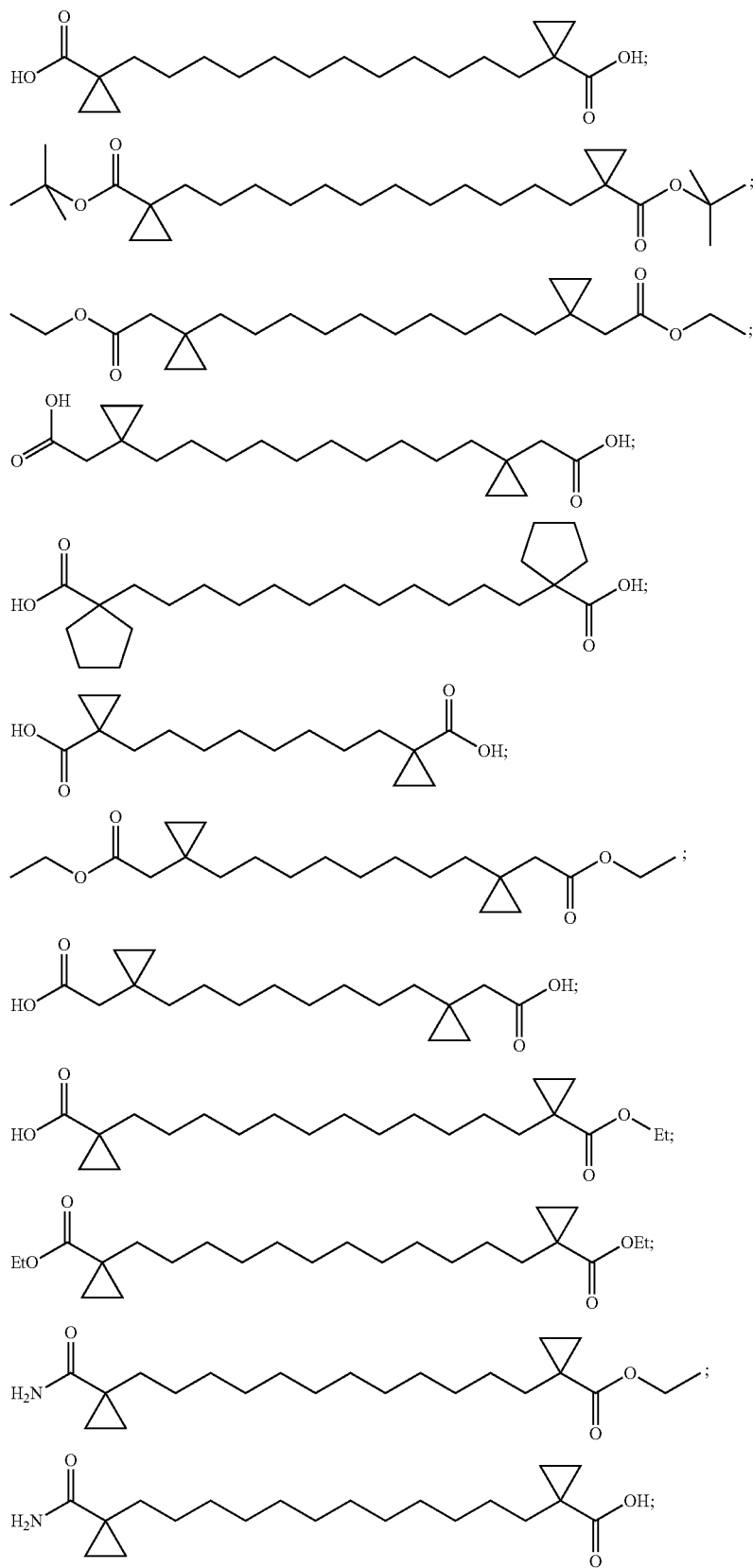

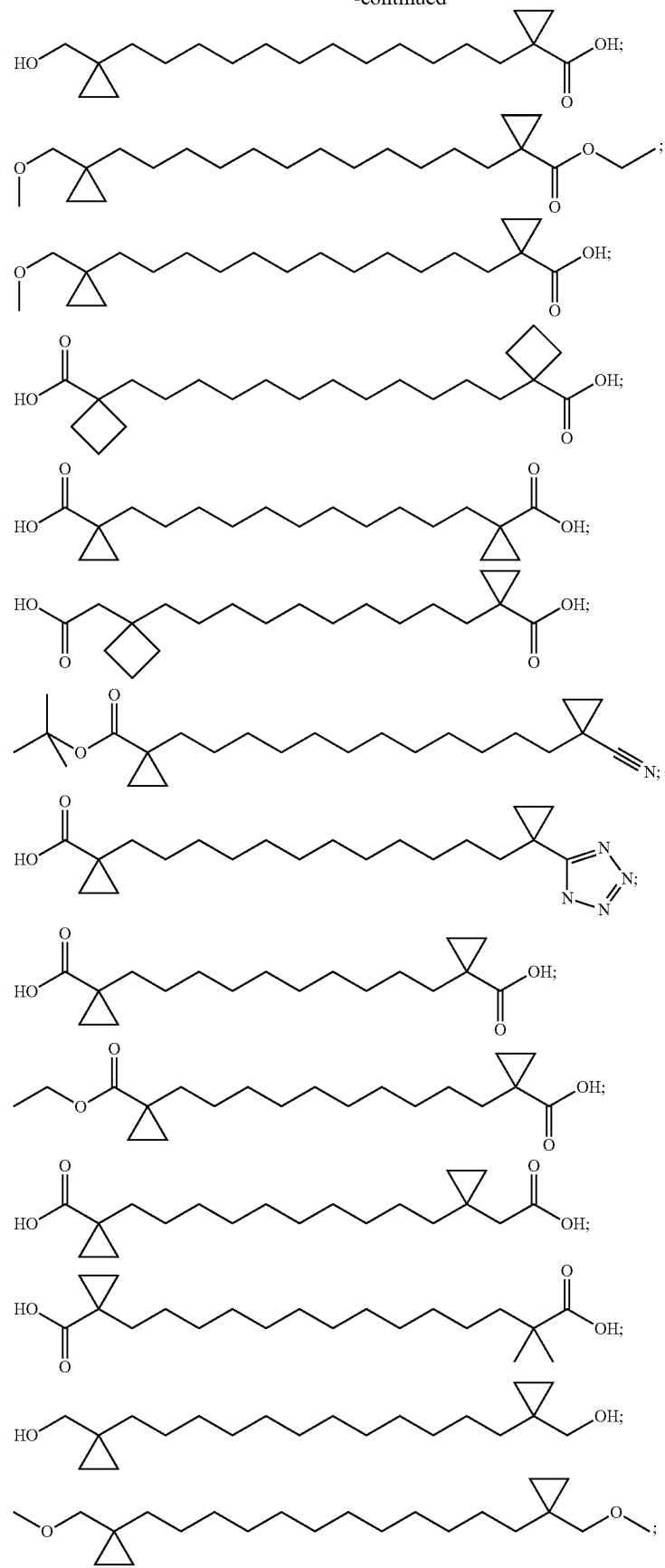

-continued
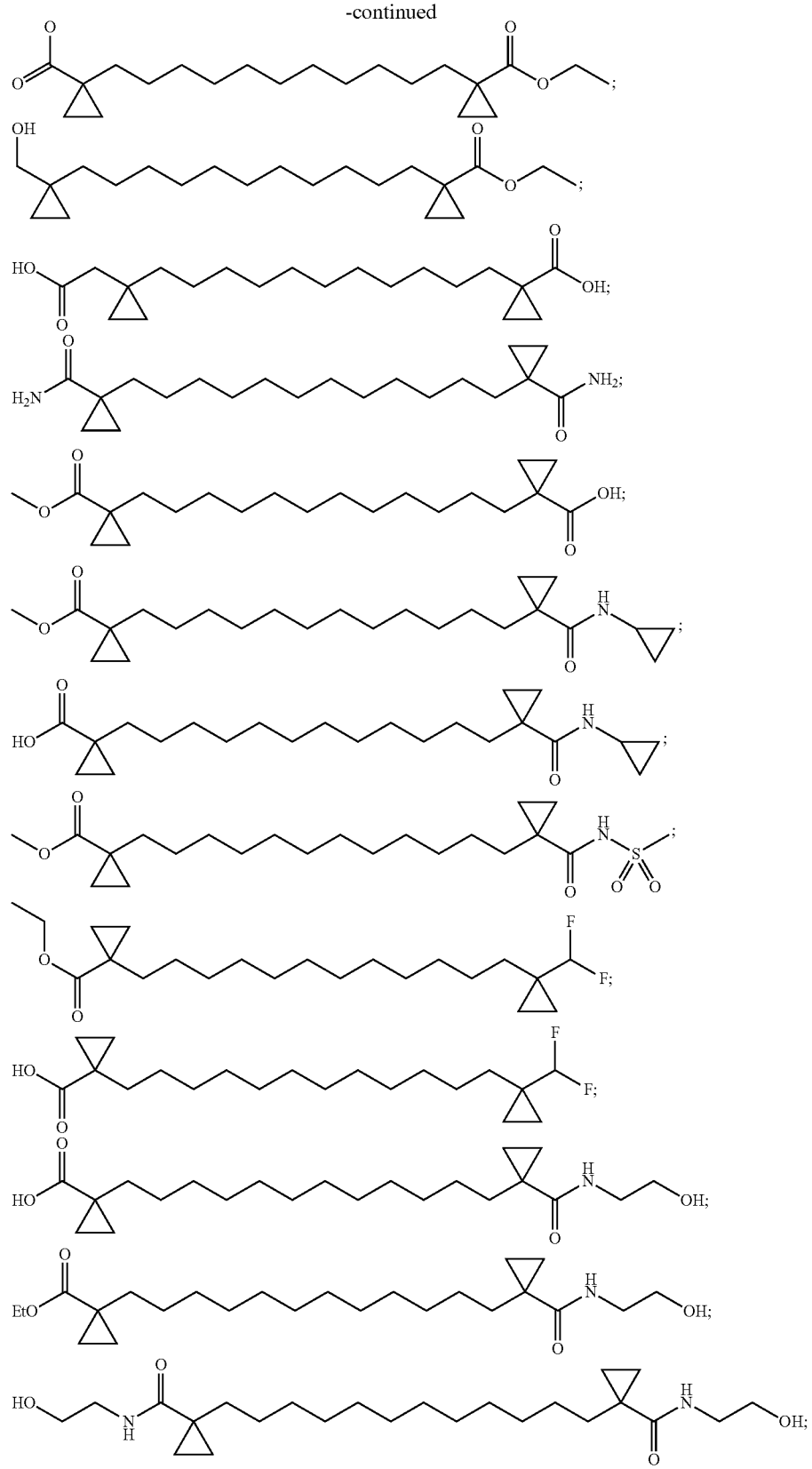
their stereoisomers, pharmaceutically acceptable salts, tautomers, and mixtures thereof.

5. A pharmaceutical composition comprising a pharmaceutically acceptable carrier and at least one compound according to claim 1.

6. A pharmaceutical composition comprising a pharmaceutically acceptable carrier and at least one compound according to claim 2.

7. A pharmaceutical composition comprising a pharmaceutically acceptable carrier and at least one compound according to claim 3.

8. A pharmaceutical composition comprising a pharmaceutically acceptable carrier and at least one compound according to claim 4.

9. A method for the treatment of insulin resistance, diabetes, and/or cardiovascular disease in a subject, the method comprising administering to the subject at least one compound according to Formula I:

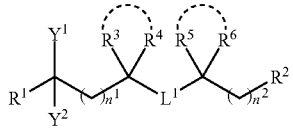

Formula I its stereoisomers and/or pharmaceutically acceptable salts, wherein:
- $R^1$ is selected from a group consisting of hydroxy, alkoxy, amine, alkyl, haloalkyl, $NHSO_2R$, or NHCOR wherein R is selected from alkyl or cycloalkyl, NHR' wherein R' is alkyl or cycloalkyl optionally substituted by hydroxy or alkoxy;
- $n^1$ and $n^2$ are independently selected from 0, 1, and 2;
- at least one of $R^3$ and $R^4$ and/or $R^5$ and $R^6$ form a cyclic ring of 3-8 carbon atoms optionally containing alkyl groups, hetero atoms, or functional groups such as O, N, $SO_2$;
- $R^3$ and $R^4$ or $R^5$ and $R^6$, when they do not form a cyclic ring, are independently selected from hydrogen, alkyl, branched alkyl, and cycloalkyl;
- $L_1$ is a linear aliphatic chain optionally containing from 4 to 16 carbon atoms, optionally substituted one or more times by alkyl, branched alkyl, cycloalkyl, or aryl;
- $R^2$ is independently selected from hydrogen, alkoxy, hydroxy, alkyl, haloalkyl, cycloalkyl, heterocycloalkyl, heteroaryl, cyano, or $COR^7$, wherein $R^7$ is selected from hydroxy, alkyl, alkoxy, or amine, NHR', $NHSO_2R$, or NHCOR;
- $Y^1$ is oxygen or hydrogen;
- $Y^2$ is optional, and wherein when $Y^2$ is present, $Y^1$ and $Y^2$ are hydrogen and when $Y^2$ is not present, $Y^1$ is a carbonyl group.

10. The method according to claim 9, wherein the method comprises administering to the subject a compound according to Formula II:

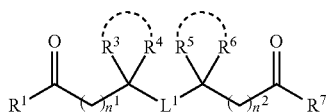

Formula II its stereoisomers and/or pharmaceutically acceptable, wherein:
- $R^1$ and $R^7$ are independently selected from a group consisting of hydroxy, alkoxy, alkyl, amine, NHR' wherein R' is alkyl or cycloalkyl optionally substituted by hydroxy or alkoxy, $NHSO_2R$ or NHCOR, wherein R is selected from alkyl or cycloalkyl;
- $n^1$ and $n^2$ are independently selected from 0, 1, and 2;
- at least one of $R^3$ and $R^4$ and/or $R^5$ and $R^6$ form a cyclic ring of 3-8 carbon atoms optionally containing alkyl groups, hetero atoms, or functional groups such as O, N, $SO_2$;
- $R^3$ and $R^4$ or $R^5$ and $R^6$, when they do not form a cyclic ring, are independently selected from hydrogen, alkyl, branched alkyl, and cycloalkyl;
- $L^1$ is independently a linear aliphatic chain optionally containing from 6 to 16 carbon-atoms and $L^1$ may optionally be substituted one or more times by alkyl, branched alkyl, cycloalkyl, or aryl.

11. The method according to claim 9, wherein the method comprises administering to the subject a compound according to Formula III:

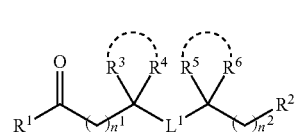

Formula III its stereoisomers and/or pharmaceutically acceptable salts for the treatment of diabetes and diabetes-associated dyslipidemia, wherein:
- $R^1$ is selected from a group consisting of hydroxy, alkoxy, amine, alkyl, haloalkyl, NHR' wherein R' is alkyl or cycloalkyl optionally substituted by hydroxy or alkoxy, $NHSO_2R$ or NHCOR, wherein R is selected from alkyl or cycloalkyl;
- $n^1$ and $n^2$ are independently selected from 0, 1, and 2;
- at least one of $R^3$ and $R^4$ and/or $R^5$ and $R^6$ form a cyclic ring of 3-8 carbon atoms optionally containing alkyl groups, hetero atoms, or functional groups such as O, N, $SO_2$;
- $R^3$ and $R^4$ or $R^5$ and $R^6$, when they do not form a cyclic ring, are independently selected from hydrogen, alkyl, branched alkyl, and cycloalkyl; and
- $L^1$ is a linear aliphatic chain optionally containing from 4 to 16 carbon-atoms and $L^1$ may optionally be substituted one or more times by alkyl, branched alkyl, cycloalkyl, or aryl. $R^2$ is independently selected from hydrogen, alkoxy, hydroxy, alkyl, haloalkyl, cycloalkyl, heterocycloalkyl, heteroaryl, cyano or $COR^7$; wherein $R^7$ is selected from a group consisting of hydroxy, alkyl, alkoxy, amine, NHR', or $NHSO_2R$.

12. The method according to claim 9, wherein the method comprises administering to the subject a compound selected from one or more of:
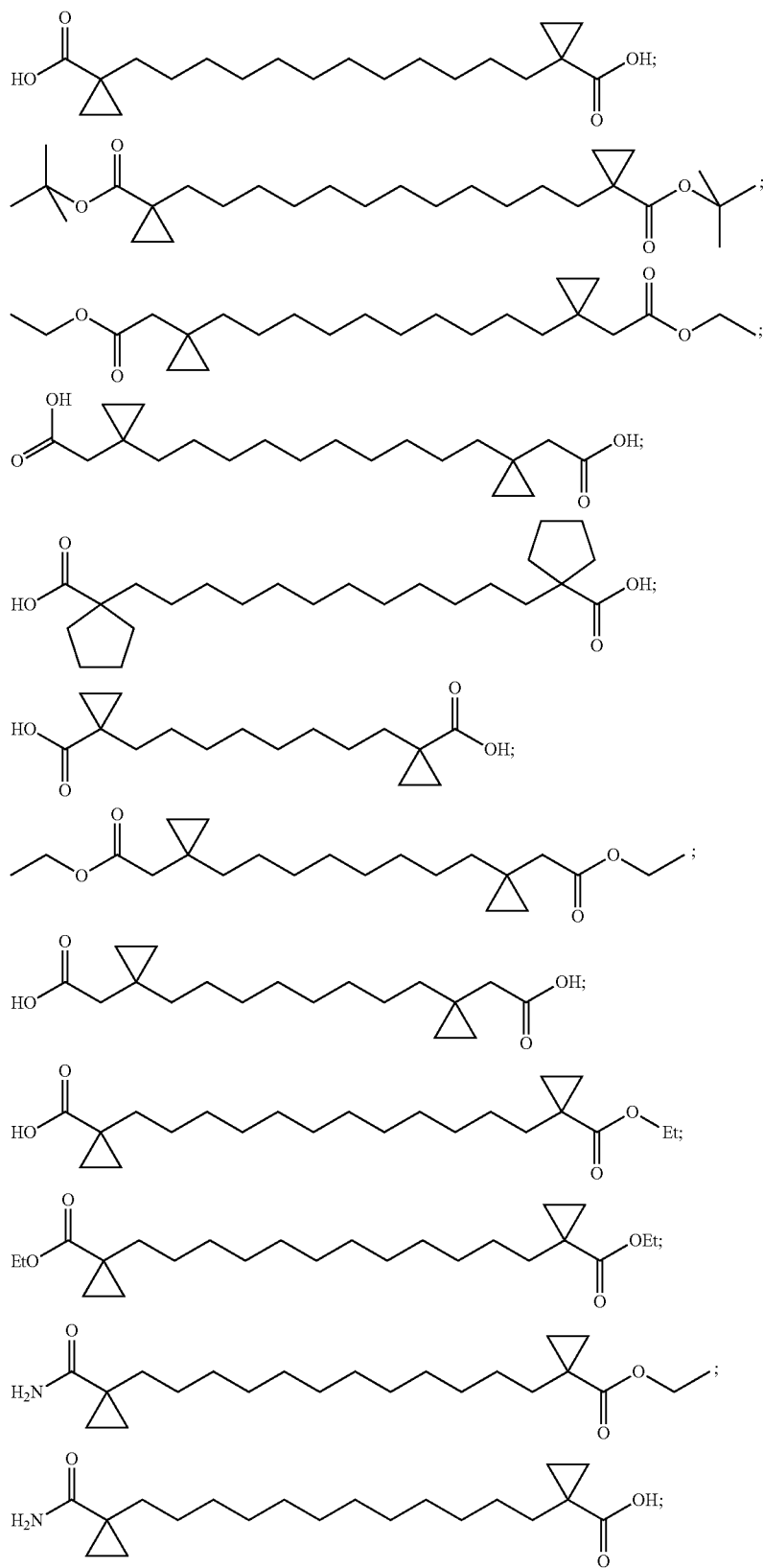

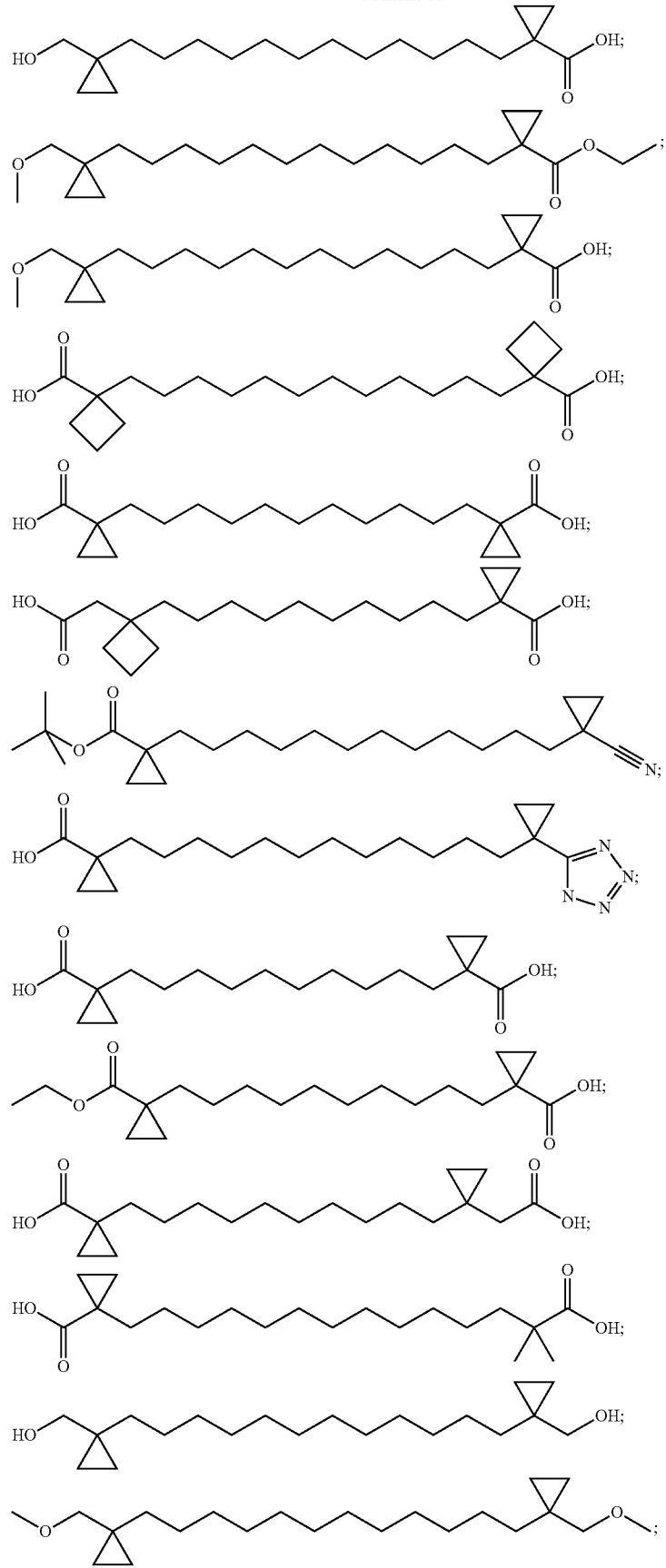

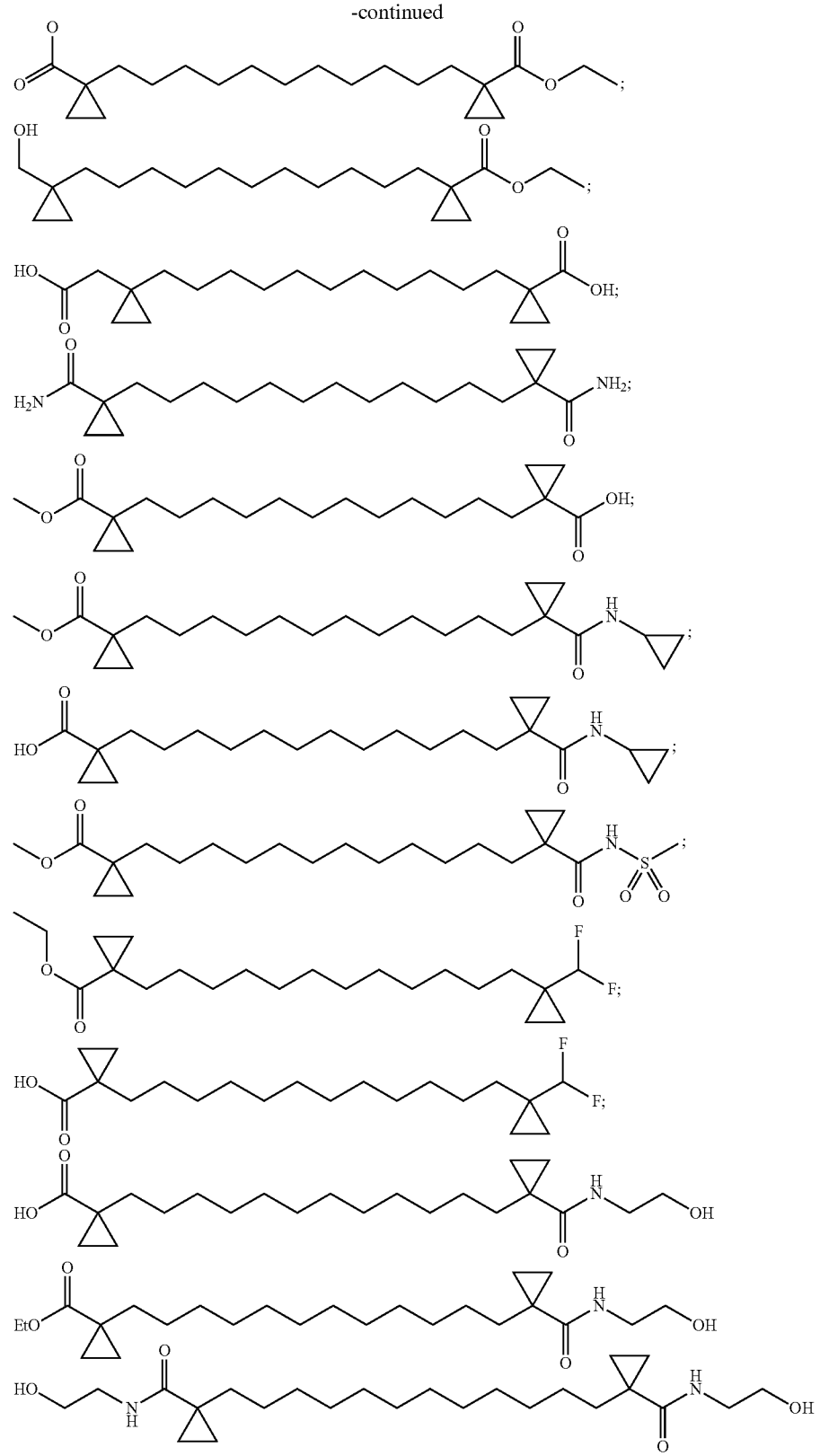
their stereoisomers, pharmaceutically acceptable salts, tautomers, and mixtures thereof.
* * * * *